US010276800B2

(12) United States Patent
Hayashi et al.

(10) Patent No.: US 10,276,800 B2
(45) Date of Patent: Apr. 30, 2019

(54) ORGANIC ELECTROLUMINESCENCE DEVICE HAVING AT LEAST AN A NODE, A HOLE INJECTION LAYER, A FIRST HOLE TRANSPORT LAYER. A SECOND HOLE TRANSPORT LAYER A LUMINOUS LAYER, AN ELECTRON TRANSPORT LAYER, AND A CATHODE

(71) Applicant: HODOGAYA CHEMICAL CO., LTD., Tokyo (JP)

(72) Inventors: Shuichi Hayashi, Tokyo (JP); Daizo Kanda, Tokyo (JP); Kazunori Togashi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/522,471

(22) PCT Filed: Nov. 12, 2015

(86) PCT No.: PCT/JP2015/081821
§ 371 (c)(1),
(2) Date: Apr. 27, 2017

(87) PCT Pub. No.: WO2016/076384
PCT Pub. Date: May 19, 2016

(65) Prior Publication Data
US 2017/0317291 A1 Nov. 2, 2017

(30) Foreign Application Priority Data
Nov. 14, 2014 (JP) ................................. 2014-231515

(51) Int. Cl.
*H01L 51/00* (2006.01)
*C07B 59/00* (2006.01)
(Continued)

(52) U.S. Cl.
CPC .......... *H01L 51/0059* (2013.01); *C07B 59/00* (2013.01); *C07B 59/001* (2013.01);
(Continued)

(58) Field of Classification Search
CPC ........................... H01L 51/0059; C07B 59/00
(Continued)

(56) References Cited

U.S. PATENT DOCUMENTS 5,639,914 A 6/1997 Tomiyama et al.
5,707,747 A 1/1998 Tomiyama
(Continued)

FOREIGN PATENT DOCUMENTS

JP 7-126615 5/1995
JP 8-48656 2/1996
(Continued)

OTHER PUBLICATIONS

Yongming Yin et al., "High-efficiency and low-efficiency-roll-off single-layer white organic light-emitting devices with a bipolar transport host"; Applied Physics Letters, vol. 101; Aug. 9, 2012; pp. 063306-1-063306-4.
(Continued)

*Primary Examiner* — Caleb E Henry
(74) *Attorney, Agent, or Firm* — Greenblum & Bernstein, P.L.C.

(57) ABSTRACT

The present invention provides an organic EL device having at least an anode, a hole injection layer, a first hole transport layer, a second hole transport layer, a luminous layer, an electron transport layer, and a cathode in order of description. The second hole transport layer includes an arylamine compound having a specific structure, and the electron transport layer includes a pyrimidine derivative having a
(Continued)

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE specific structure. The organic EL device of the present invention has a high efficiency, a low driving voltage, and a longer life.

9 Claims, 96 Drawing Sheets

(51) Int. Cl.
    *C07C 211/58*     (2006.01)
    *C07D 307/91*     (2006.01)
    *C09K 11/06*     (2006.01)
    *C07C 211/54*     (2006.01)
    *H01L 51/50*     (2006.01)
    *C07C 211/61*     (2006.01)

(52) U.S. Cl.
    CPC .......... *C07C 211/54* (2013.01); *C07C 211/58* (2013.01); *C07C 211/61* (2013.01); *C07D 307/91* (2013.01); *C09K 11/06* (2013.01); *H01L 51/006* (2013.01); *H01L 51/0052* (2013.01); *H01L 51/0061* (2013.01); *H01L 51/0067* (2013.01); *H01L 51/0072* (2013.01); *H01L 51/0077* (2013.01); *H01L 51/5064* (2013.01); *C07B 2200/05* (2013.01); *C07C 2603/18* (2017.05); *C09K 2211/1007* (2013.01); *C09K 2211/1011* (2013.01); *C09K 2211/1014* (2013.01); *C09K 2211/1018* (2013.01); *C09K 2211/1029* (2013.01); *H01L 51/0054* (2013.01); *H01L 51/0073* (2013.01); *H01L 51/5012* (2013.01); *H01L 51/5016* (2013.01); *H01L 51/5056* (2013.01); *H01L 51/5072* (2013.01)

(58) Field of Classification Search
    USPC .......................................................... 257/40
    See application file for complete search history.

(56) References Cited

U.S. PATENT DOCUMENTS

| | | | |
|---|---|---|---|
| 5,792,557 A | 8/1998 | Nakaya et al. | |
| 6,344,283 B1 | 2/2002 | Inoue et al. | |
| 6,878,469 B2 | 4/2005 | Yoon et al. | |
| 7,357,992 B2 | 4/2008 | Kato et al. | |
| 7,402,701 B2 | 7/2008 | Kato et al. | |
| 7,759,030 B2 | 7/2010 | Abe et al. | |
| 7,799,492 B2 | 9/2010 | Abe et al. | |
| 8,021,764 B2 | 9/2011 | Hwang et al. | |
| 8,021,765 B2 | 9/2011 | Hwang et al. | |
| 8,188,315 B2 | 5/2012 | Hwang et al. | |
| 8,394,510 B2 | 3/2013 | Mizuki et al. | |
| 8,748,014 B2 | 6/2014 | Yokoyama et al. | |
| 8,895,159 B2 | 11/2014 | Mizuki et al. | |
| 8,974,922 B2 | 3/2015 | Hwang et al. | |
| 9,478,754 B2 | 10/2016 | Hwang et al. | |
| 2002/0102434 A1 | 8/2002 | Inoue et al. | |
| 2004/0110030 A1 | 6/2004 | Inoue et al. | |
| 2005/0260451 A1 | 11/2005 | Kijima | |
| 2009/0091244 A1 | 4/2009 | Negishi et al. | |
| 2011/0073852 A1* | 3/2011 | Yokoyama | C07D 471/04 257/40 |
| 2012/0119197 A1 | 5/2012 | Nishimura et al. | |
| 2014/0034924 A1* | 2/2014 | Kawata | H01L 51/0072 257/40 |
| 2014/0183495 A1* | 7/2014 | Lee | H01L 51/0052 257/40 |
| 2015/0380657 A1 | 12/2015 | Yokoyama et al. | |
| 2016/0126464 A1 | 5/2016 | Yokoyama et al. | |
| 2017/0005273 A1 | 1/2017 | Hwang et al. | |

FOREIGN PATENT DOCUMENTS

| | | |
|---|---|---|
| JP | 3194657 | 6/2001 |
| JP | 2005-108804 | 4/2005 |
| JP | 2005-339823 | 12/2005 |
| JP | 2006-151979 | 6/2006 |
| JP | 2007-191465 | 8/2007 |
| JP | 2011-9758 | 1/2011 |
| JP | 4943840 | 5/2012 |
| WO | 03/060956 | 7/2003 |
| WO | 2008/062636 | 5/2008 |
| WO | 2011/059000 | 5/2011 |
| WO | 2014/129201 | 8/2014 |
| WO | 2014/199567 | 12/2014 |
| WO | 2015/190400 | 12/2015 |

OTHER PUBLICATIONS

International Search Report issued in WIPO Patent Application No. PCT/JP2015/081821, dated Feb. 2, 2016.
Supplementary European Search Report issued with respect to Application No. 15858344.3, dated Jun. 6, 2018.

\* cited by examiner

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE (1-5)

(1-6)

(1-7)

(1-8)

(1-9)

(1-10)

(1-11)

(1-12)

(1-18)

(1-19)

(1-20)

(1-21)

(1-22)

(1-23)

(1-24)

(1-25)

(1-26)

(1-27)

(1-28)

(1-29)

(1-30)

(1-31)

(1-32)

(1-33)

(1-34)

(1-35)

(1-36)

(2-1)

(2-2)

(2-3)

(2-4)

(2-5)

(2-6)

(2-7)

(2-8)

(2-9)

(2-10)

(2-11)

(2-12)

(2-13)

(2-14)

(2-15)

(2-16)

(2-17)

(2-18)

(2-19)

(2-20)

(2-21)

(2-22)

(2-23)

(2-24)

(2-25)

(2-26)

(2-27)

(2-28)

(2-29)

(2-30)

(2-31)

(2-32)

(2-33)

(2-34)

(2-35)

(2-36)

(2-37)

(2-38)

(2-39)

(2-40)

(2-41)

(2-42)

(2-43)

(2-44)

(2-45)

(2-46)

(2-47)

(2-48)

(2-49)

(2-50)

(2-51)

(2-52)

(2-53)

(2-54)

(2-55)

(2-56)

(2-57)

(2-62)

(2-63)

(2-64)

(2-65)

(2-66)

(2-67)

(2-68)

(2-69)

(2-70)

(2-71)

(2-72)

(2-73)

(2-74)

(2-75)

(2-76)

(2-77)

(2-78)

(2-79)

(2-80)

(2-81)

(2-82)

(2-83)

(2-84)

(2-85)

(2-86)

(2-87)

(2-88)

(2-89)

(2-90)

(2-91)

(2-92)

(2-93)

(2-94)

(2-95)

(2-96)

(2-97)

(2-98)

(2-99)

(2-100)

(2-101)

(2-102)

(2-103)

(2-104)

(2-105)

(2-106)

(2-107)

(2-108)

(2-109)

(2-110)

(2-111)

(2-112)

(2-113)

(2-114)

(2-115)

(2-116)

(2-117)

(2-118)

(2-119)

(2-120)

(2-121)

(2-122)

(2-123)

(2-124)

(2-125)

(2-126)

(2-127)

(2-128)

(2-129)

(2-130)

(2-131)

(2-132)

(2-133)

(2-134)

(2-135)

(2-136)

(2-137)

(2-138)

(2-139)

(2-140)

(2-141)

(2-142)

(2-143)

(2-144)

(2-145)

(2-146)

(2-147)

(2-148)

(2-149)

(2-150)

(2-151)

(2-152)

(2-153)

(2-154)

(2-155)

(2-156)

(2-157)

(2-158)

(2-159)

(2-160)

(2-161)

(2-162)

(2-163)

(2-164)

(2-165)

(2-166)

(2-167)

(2-168)

(2-169)

(2-170)

(2-171)

(2-172)

(2-173)

(2-174)

(2-175)

(2-176)

(2-177)

(2-178)

(2-179)

(2-180)

(2-185)

(2-186)

(2-187)

(2-188)

(2-189)

(2-190)

(2-191)

(2-192)

(2-193)

(2-194)

(2-195)

(2-196)

(2-197)

(2-198)

(2-199)

(2-200)

(2-201)

(2-202)

(2-203)

(2-204)

(2-205)

(2-206)

(2-207)

(2-208)

(2-209)

(2-210)

(2-211)

(2-212)

(2-213)

(2-214)

(2-215)

(2-216)

(2-217)

(2-218)

(2-219)

(2-220)

(2-221)

(2-222)

(2-223)

(2−224)

(2−225)

(2−226)

(2−227)

(2-232)

(2-233)

(2-234)

(2-235)

(2-236)

(2-237)

(2-238)

(2-239)

(2-240)

(2-241)

(2-242)

(2-243)

(2-244)

(2-245)

(2-246)

(2-247)

(2-248)

(2-249)

(2-250)

(2-251)

(2-252)

(2-253)

(2-254)

(2-255)

(2-256)

(2-257)

(2-258)

(2-259)

(2-260)

(2-261)

(2-262)

(2-263)

(2-264)

(4-1)

(4-2)

(4-3)

(4-4)

(4-5)

(4-6)

(4-7)

(4-8)

(4-9)

(4-10)

(4-11)

(4-12)

(4-13)

(4-14)

(4-15)

(4-16)

(4-17)

(4'-1)

(4'-2)

(5-1)

(5-2)

(5-3)

(5-4)

(5-5)

(5-6)

(5-7)

(5-8)

(5-9)

(5-10)

(5-11)

(5-12)

(5-13)

(5-14)

(5-15)

(5-16)

(5-17)

(5-18)

(5-19)

(5-20)

(5-21)

(5-22)

(5-23)

(5'-1)

(5'-2)

ORGANIC ELECTROLUMINESCENCE DEVICE HAVING AT LEAST AN A NODE, A HOLE INJECTION LAYER, A FIRST HOLE TRANSPORT LAYER. A SECOND HOLE TRANSPORT LAYER A LUMINOUS LAYER, AN ELECTRON TRANSPORT LAYER, AND A CATHODE

TECHNICAL FIELD

The present invention relates to an organic electroluminescence device, and more particularly to an organic electroluminescence device (abbreviated below as "organic EL device") using a specific arylamine compound and a specific pyrimidine derivative.

BACKGROUND ART

An organic EL device is a light-emitting device, and is brighter, better in visibility, and capable of clearer display than a liquid crystal device. Hence, active researches have been conducted on organic EL devices.

In 1987, C. W. Tang et al. of Eastman Kodak Company developed a laminated structure device sharing various roles for light emission among different materials, thereby imparting practical applicability to organic EL devices. The developed organic EL device is configured by laminating a layer of a fluorescent body capable of transporting electrons, and a layer of an organic substance capable of transporting holes. As a result of injecting positive charges and negative charges into the layer of the fluorescent body to perform light emission, it is possible to obtain a high luminance of 1000 cd/m$^2$ or higher at a voltage of 10 V or less (see PTL 1 and PTL 2).

Many improvements have been heretofore made to put the organic EL devices to practical use. For example, it is generally well known that high efficiency and durability can be achieved by further segmenting the roles to be played by respective layers of the laminated structure and providing an anode, a hole injection layer, a hole transport layer, a luminous layer, an electron transport layer, an electron injection layer, and a cathode on a substrate.

For further increase in the luminous efficiency, it has been attempted to utilize triplet excitons, and the utilization of phosphorescent luminous compounds has been investigated. Furthermore, devices utilizing light emission by thermally activated delayed fluorescence (TADF) have been developed. In 2011, Adachi et al. from Kyushu University have realized an external quantum efficiency of 5.3% with a device using a thermally activated delayed fluorescence material.

The luminous layer can also be prepared by doping a charge transporting compound, generally called a host material, with a fluorescent compound, a phosphorescent luminous compound, or a material radiating delayed fluorescence. The selection of the organic material in the organic EL device greatly affects the characteristics of the device, such as efficiency and durability.

With the organic EL device, the charges injected from both electrodes recombine in the luminous layer, thereby producing light emission, and how efficiently the charges of the holes and the electrons are passed on to the luminous layer is of importance, and a device that exhibits excellent carrier balance is required. Further, by enhancing hole injection property or increasing electron blocking property, that is, property to block electrons injected from the cathode, the probability of holes and electrons recombining is increased. Moreover, excitons generated in the luminous layer are confined. By so doing, it is possible to obtain a high luminous efficiency. Therefore, the role of the hole transport material is important, and a demand has been created for a hole transport material having high hole injection property, high hole mobility, high electron blocking property, and high durability to electrons.

From the viewpoint of device life, heat resistance and amorphousness of the materials are also important. A material with a low heat resistance is thermally decomposed even at a low temperature by heat produced during device driving, and the material deteriorates. In a material with low amorphousness, crystallization of a thin film occurs even in a short time, and the device deteriorates. Thus, high heat resistance and satisfactory amorphousness are required of the materials to be used.

N,N'-diphenyl-N,N'-di($\alpha$-naphthyl)benzidine (NPD) and various aromatic amine derivatives are known as hole transport materials which have been heretofore used in organic EL devices (see PTL 1 and PTL 2). NPD has satisfactory hole transport capacity, but the glass transition temperature (Tg), which is an indicator of heat resistance, is as low as 96° C. and device characteristics degrade due to crystallization under high-temperature conditions.

Further, among the aromatic amine derivatives disclosed in PTL 1 and 2, there are also compounds with an excellent hole mobility of 10$^{-3}$ cm$^2$/Vs or higher, but since electron blocking property is insufficient, some of electrons pass through the luminous layer, and no increase in luminous efficiency can be expected. Thus, materials with better electron blocking property, higher stability in a thin film, and high heat resistance are needed to increase further the efficiency.

Moreover, an aromatic amine derivative with high durability has also been reported in PTL 3. However, the aromatic amine derivative disclosed in PTL 3 is used as a charge transport material for an electrophotographic photosensitive body and there is no example of application to an organic EL device.

Arylamine compounds having a substituted carbazole structure have been suggested as compounds with improved properties such as heat resistance and hole injection property (see PTL 4 and PTL 5). Although heat resistance, luminous efficiency, and the like of devices using these compounds for a hole injection layer or hole transport layer have been improved, the results are still insufficient and further decrease in a driving voltage and increase in luminous efficiency are needed.

Thus, it is expected to increase the yield in device production and to improve device characteristics of organic EL devices, for example, to realize devices in which holes and electrons can recombine with a high efficiency and which have a high luminous efficiency, a low driving voltage, and a long life by combining materials with excellent hole injection-transport performance, electron injection-transport performance, stability of a thin film, durability or the like.

CITATION LIST

Patent Literature

PTL 1: Japanese Patent Application Publication No. H8-048656
PTL 2: Japanese Patent No. 3194657
PTL 3: Japanese Patent No. 4943840
PTL 4: Japanese Patent Application Publication No. 2006-151979
PTL 5: WO 2008/62636
PTL 6: WO 2011/059000
PTL 7: WO 2003/060956

PTL 8: Japanese Patent Application Publication No. H7-126615

PTL 9: Japanese Patent Application Publication No. 2005-108804

SUMMARY OF INVENTION

Technical Problem

It is an object of the present invention to provide an organic EL device which has (1) a high luminous efficiency and a high power efficiency, (2) a low emission start voltage, (3) a low practical driving voltage, and (4) a particularly long life by combining materials for an organic EL device with excellent hole injection-transport performance and electron injection-transport performance, electron blocking capacity, and stability in a thin-film state, durability or the like so as to demonstrate effectively the properties of each material.

Solution to Problem

The inventors of the present invention noted that arylamine-based materials have excellent hole injection-transport capacity and stability of a thin film and durability. The inventors also noted that pyrimidine derivatives have excellent electron injection-transport capacity and stability of a thin film and durability.

The inventors of the present invention found that holes can be efficiently injected and transported to a luminous layer when a hole transport layer has a two-layer configuration and an arylamine compound having a specific structure is selected as a material of the hole transport layer (second hole transport layer) adjacent to a luminous layer. Furthermore, it was found that electrons can be efficiently injected and transported to a luminous layer when a pyrimidine derivative having a specific structure is selected as a material of the electron transport layer.

The combination of such arylamine compound and pyrimidine derivative was further combined with various materials to examine combinations of materials having refined carrier balance, and the characteristic of the devices were intensively evaluated. As a result, the inventors have accomplished the present invention.

According to the present invention, there is provided an organic electroluminescence device having at least an anode, a hole injection layer, a first hole transport layer, a second hole transport layer, a luminous layer, an electron transport layer, and a cathode in order of description, wherein the second hole transport layer includes an arylamine compound represented by the following general formula (1), and the electron transport layer includes a pyrimidine derivative represented by the following general formula (2).

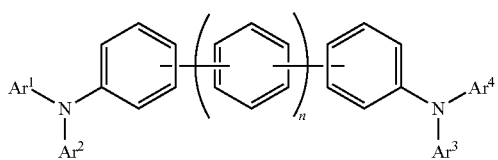

(1)

In this formula, $Ar^1$ to $Ar^4$ each represent an aromatic hydrocarbon group, an aromatic heterocyclic group, or a condensed polycyclic aromatic group and n represents an integer of 2 to 4.

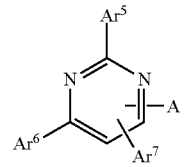

(2)

In this formula, $Ar^5$ represents an aromatic hydrocarbon group, an aromatic heterocyclic group, or a condensed polycyclic aromatic group, $Ar^6$ and $Ar^7$ each represent a hydrogen atom, an aromatic hydrocarbon group, an aromatic heterocyclic group, or a condensed polycyclic aromatic group, $Ar^6$ and $Ar^7$ may not each be a hydrogen atom at the same time and A represents a monovalent group represented by the following structural formula (3).

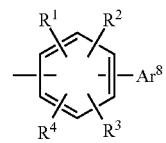

(3)

In this formula, $Ar^8$ represents an aromatic heterocyclic group, $R^1$ to $R^4$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group, and $R^1$ to $R^4$ may be bonded to $Ar^8$ via a single bond, a substituted or unsubstituted methylene group, an oxygen atom, or a sulfur atom to form a ring.

In the organic electroluminescence device (organic EL device) of the present invention, it is preferred that:

(1) the first hole transport layer include a triarylamine compound having 3 to 6 triarylamine structures in a molecule, the triarylamine structures being linked to each other via a single bond or a divalent group having no heteroatom;

(2) the triarylamine compound having 3 to 6 triarylamine structures be a triarylamine compound which has 4 triarylamine structures in a molecule and is represented by the following general formula (4):

(4)

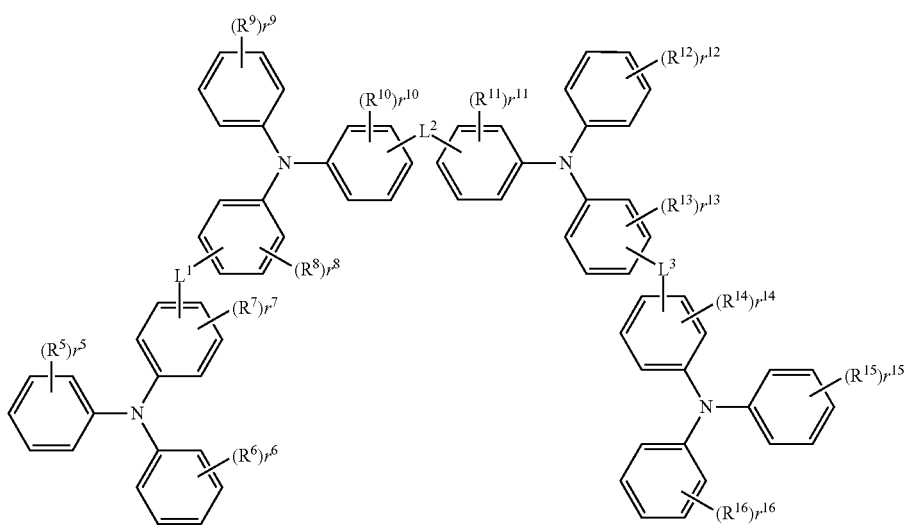

Wherein $r^5$, $r^6$, $r^9$, $r^{12}$, $r^{15}$, and $r^{16}$ each represent an integer of 0 to 5;

$r^7$, $r^8$, $r^{10}$, $r^{11}$, $r^{13}$, and $r^{14}$ each represent an integer of 0 to 4;

$R^5$ to $R^{16}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group; when a plurality of these groups is bonded to the same benzene ring, the plurality of bonded groups may be bonded to each other via a single bond, a substituted or unsubstituted methylene group, an oxygen atom, or a sulfur atom to form a ring; and $L^1$ to $L^3$ each represent a single bond or a divalent group represented by any of the following structural formulas (B) to (G):

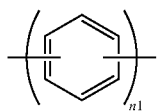
(B)

wherein
n1 represents an integer of 1 to 3,

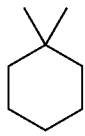
(C)

-continued

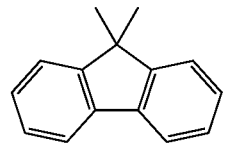
(D)

—CH$_2$— (E)

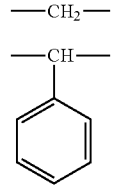
(F)

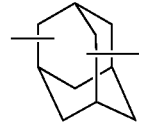
(G)

(3) the first hole transport layer include a triarylamine compound having 2 triarylamine structures in a molecule, the triarylamine structures being linked to each other via a single bond or a divalent group having no heteroatom;

(4) the triarylamine compound having 2 triarylamine structures be represented by the following general formula (5):

(5)

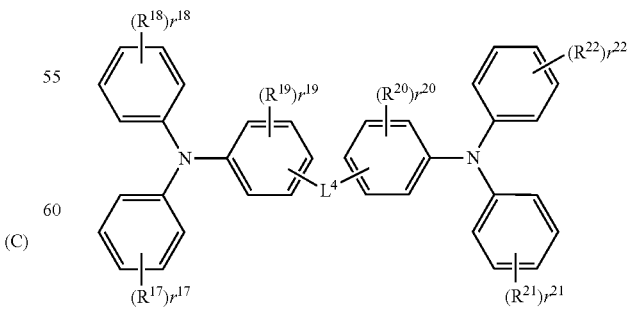

wherein
$r^{17}$, $r^{18}$, $r^{21}$, and $r^{22}$ each represent an integer of 0 to 5;
$r^{19}$ and $r^{20}$ each represent an integer of 0 to 4;

$R^{17}$ to $R^{22}$ each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group; when a plurality of these groups is bonded to the same benzene ring, the plurality of bonded groups may be bonded to each other via a single bond, a substituted or unsubstituted methylene group, an oxygen atom, or a sulfur atom to form a ring;

$L^4$ represents a single bond or a divalent group represented by any of the following structural formulas (C) to (G);

(5) the pyrimidine derivative included in the electron transport layer be represented by the following general formula (2a):

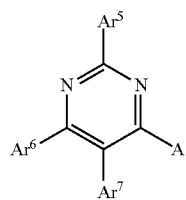

(2a)

Wherein, $Ar^5$ to $Ar^7$ and A are as defined in the general formula (2);

(6) the pyrimidine derivative included in the electron transport layer be represented by the following general formula (2b):

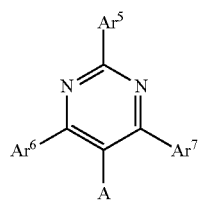

(2b)

Wherein, $Ar^5$ to $Ar^7$ and A are as defined in the general formula (2);

(7) In the general formula (2), A is a monovalent group indicated by the following structural formula (3a):

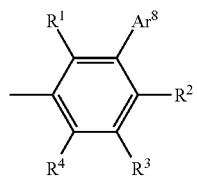

(3a)

Wherein, $Ar^8$ and $R^1$ to $R^4$ are as defined in the structural formula (3);

(8) the luminous layer include a blue luminous dopant;
(9) the blue luminous dopant is a pyrene derivative;
(10) the luminous layer include an anthracene derivative; and
(11) the luminous layer include the anthracene derivative as a host material.

Advantageous Effects of Invention

In the present invention, in order to enable effective injection and transport of holes and electrons, a hole transport layer was provided with a two-layer configuration, and an arylamine compound having a specific structure and a pyrimidine derivative having a specific structure were combined with consideration for carrier balance. As a result, it was possible to realize an organic EL device in which holes and electrons could be injected and transported in the luminous layer with satisfactory efficiency and which had a high efficiency, a low driving voltage, and a long life.

Furthermore, a triarylamine compound having a specific structure was combined as the material of the first hole transport layer with the abovementioned combination of materials, that is, a combination of materials with further refined carrier balance was selected. As a result, it was possible to realize an organic EL device in which holes could be injected and transported in the luminous layer with more satisfactory efficiency and which had a high efficiency, a low driving voltage, and a longer life. Thus, with the present invention, it is possible to provide an organic EL device which not only has a luminous efficiency higher and a driving voltage lower than those of the conventional organic EL devices, but also particularly excels in durability.

DESCRIPTION OF EMBODIMENTS

Figure 1:
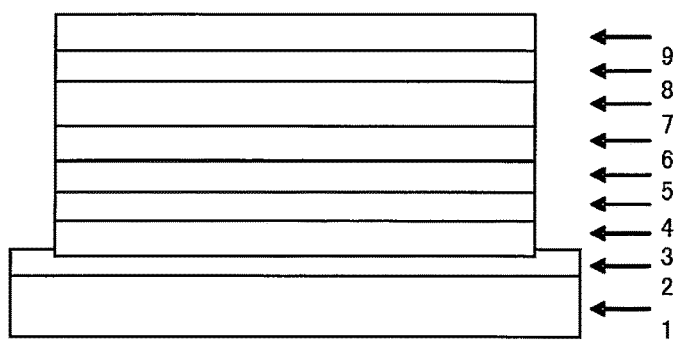
FIG. 1 is a view showing the configuration of the organic EL devices of Device Examples 1 to 6 and Comparative Device Examples 1 to 4.
Figure 2:
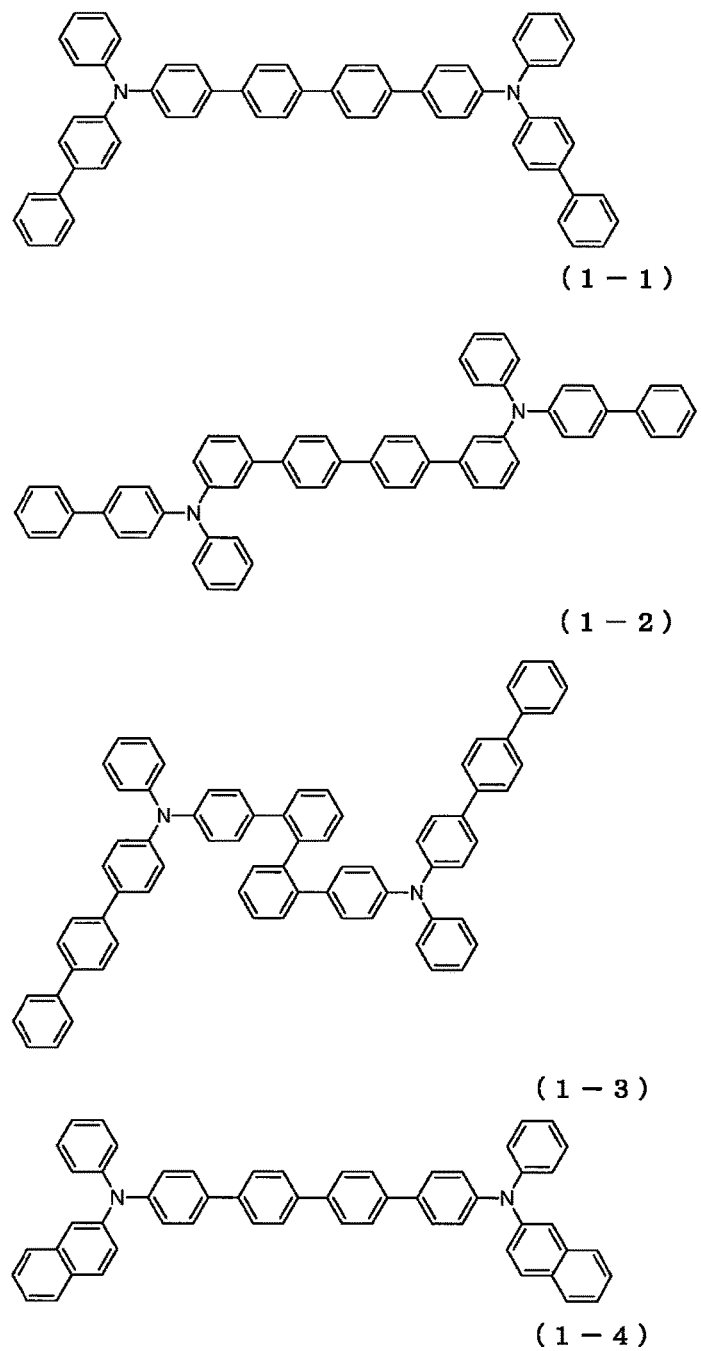
FIG. 2 is a view showing the structural formulas of Compounds (1-1) to (1-4) in the arylamine compound of a general formula (1).
Figure 3:
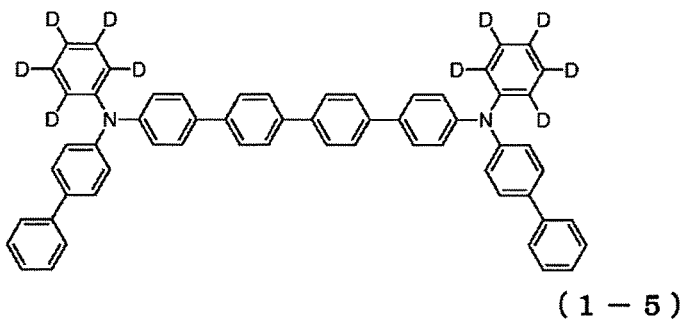
FIG. 3 is a view showing the structural formulas of Compounds (1-5) to (1-8) in the arylamine compound of the general formula (1).
Figure 3:
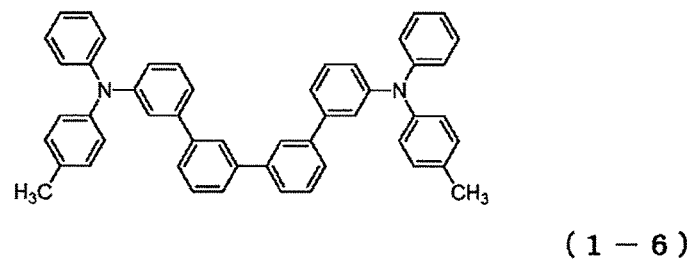
Figure 3:
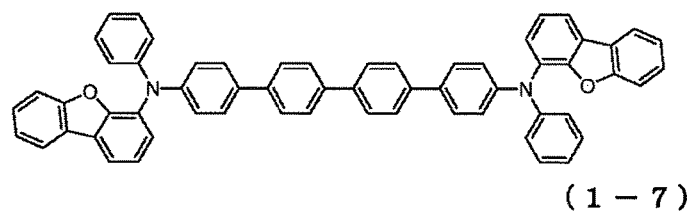
Figure 3:
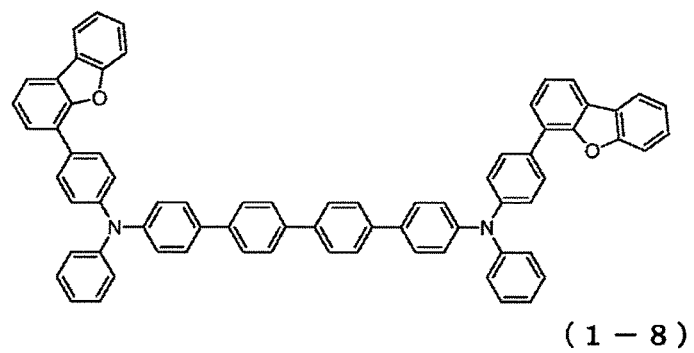
Figure 4:
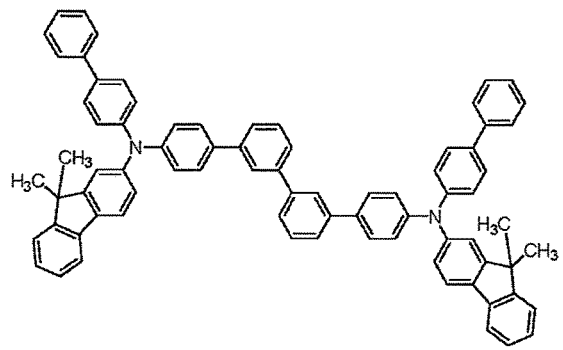
FIG. 4 is a view showing the structural formulas of Compounds (1-9) to (1-12) in the arylamine compound of the general formula (1).
Figure 4:
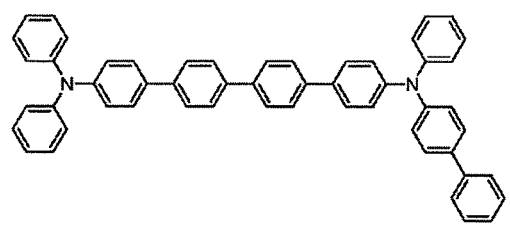
Figure 4:
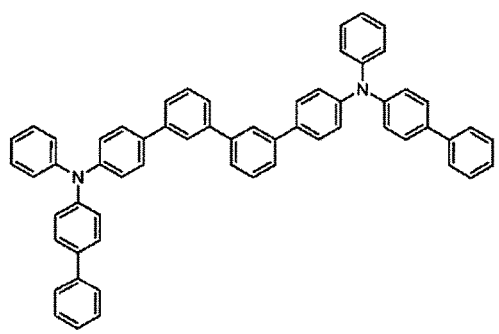
Figure 4:
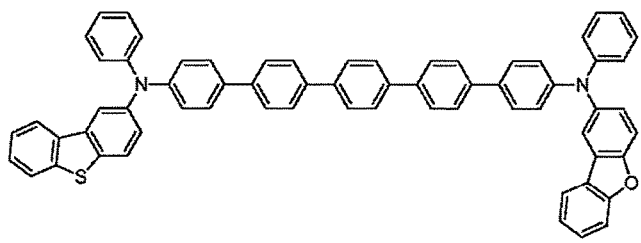
Figure 5:
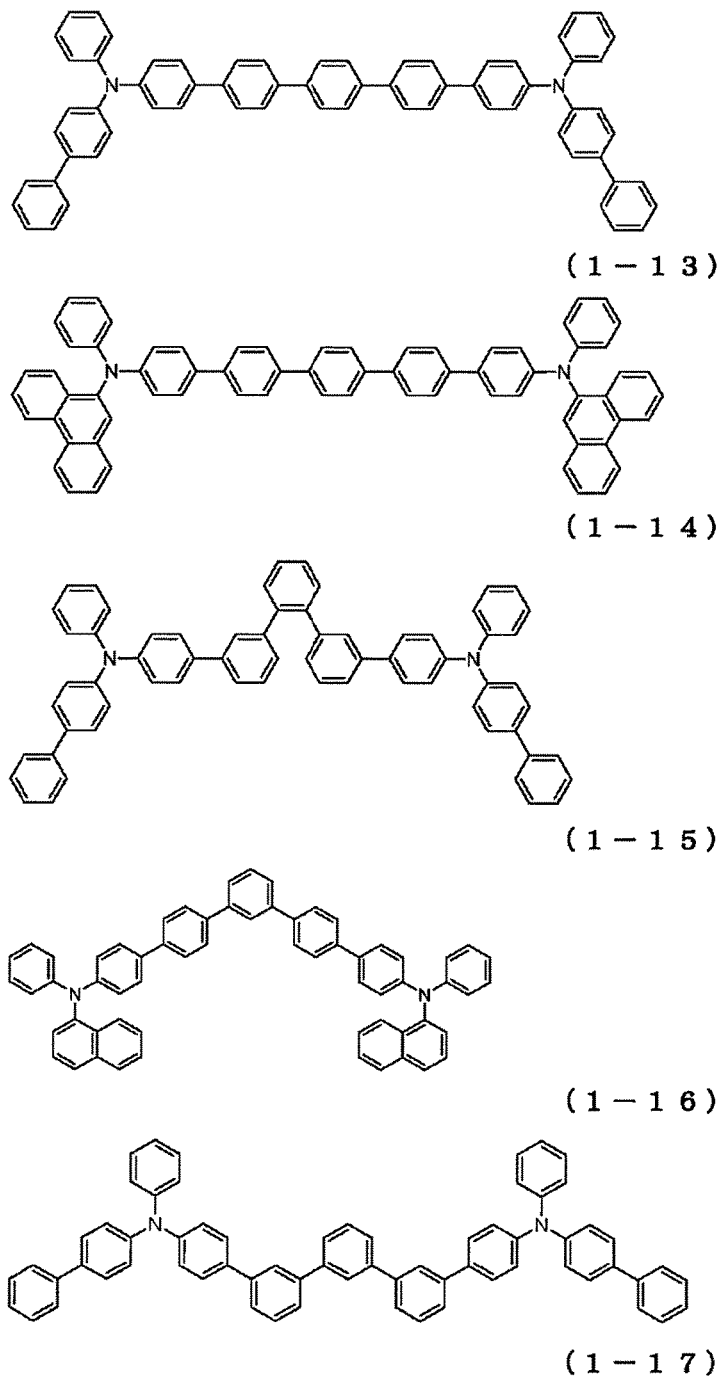
FIG. 5 is a view showing the structural formulas of Compounds (1-13) to (1-17) in the arylamine compound of the general formula (1).
Figure 6:
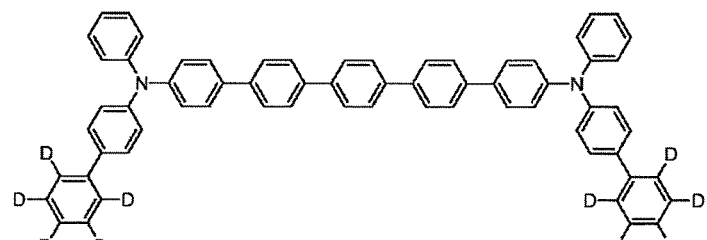
FIG. 6 is a view showing the structural formulas of Compounds (1-18) to (1-21) in the arylamine compound of the general formula (1).
Figure 6:
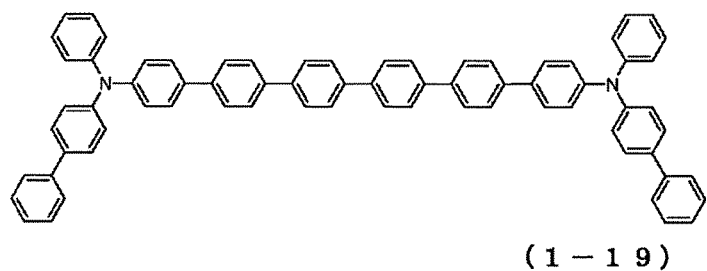
Figure 6:
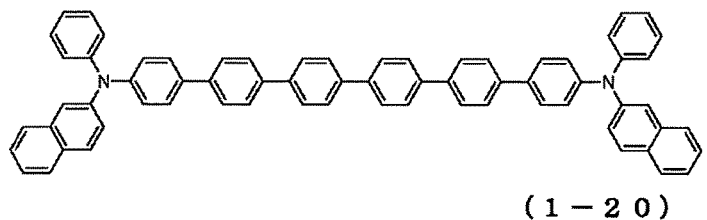
Figure 6:
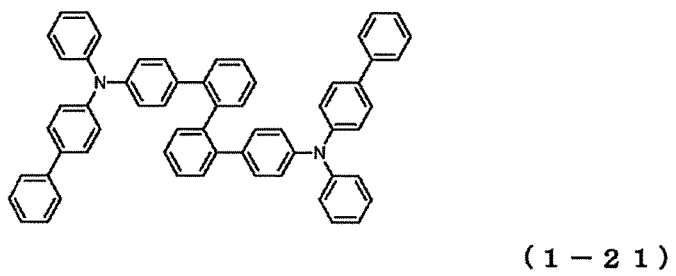
Figure 7:
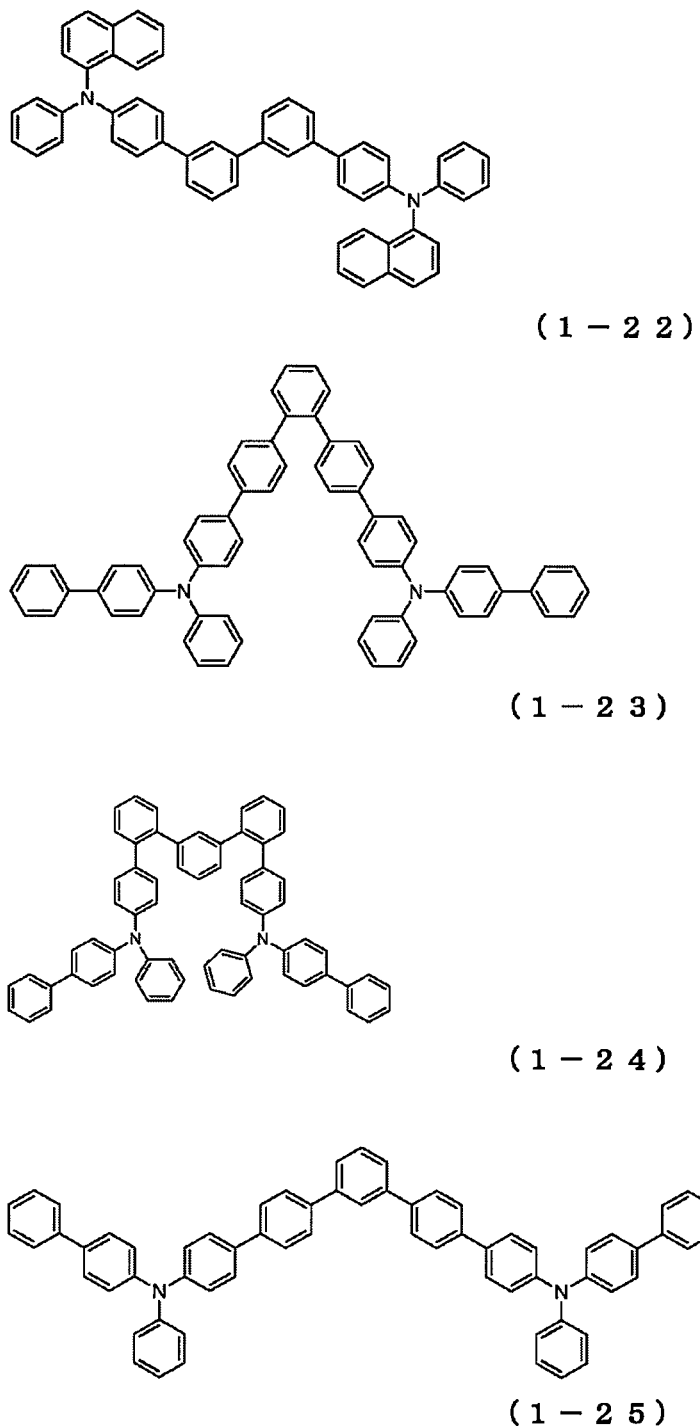
FIG. 7 is a view showing the structural formulas of Compounds (1-22) to (1-25) in the arylamine compound of the general formula (1).
Figure 8:
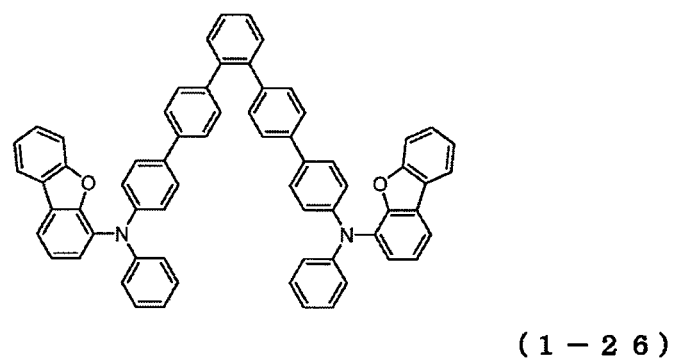
FIG. 8 is a view showing the structural formulas of Compounds (1-26) to (1-29) in the arylamine compound of the general formula (1).
Figure 8:
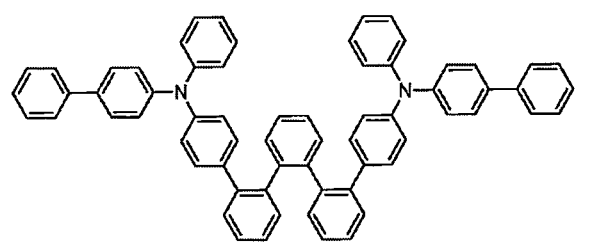
Figure 8:
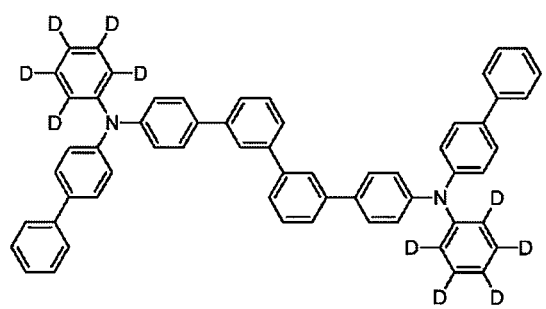
Figure 8:
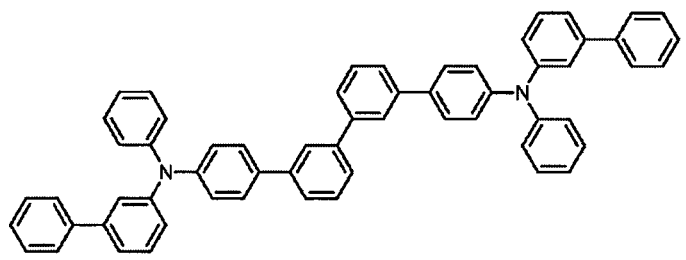
Figure 9:
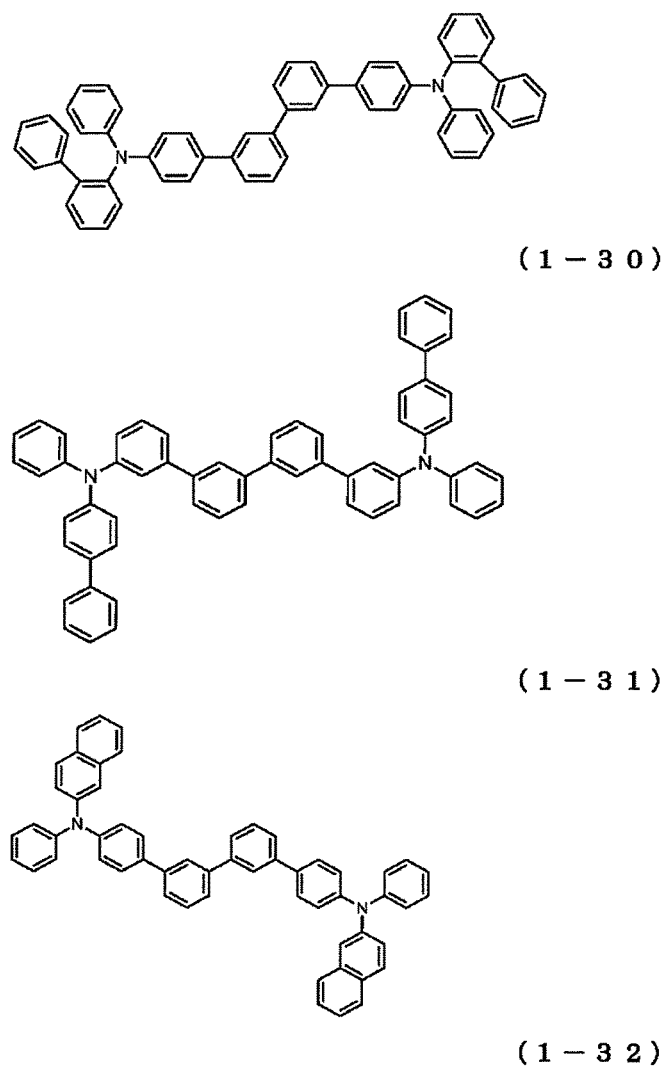
FIG. 9 is a view showing the structural formulas of Compounds (1-30) to (1-32) in the arylamine compound of the general formula (1).
Figure 10:
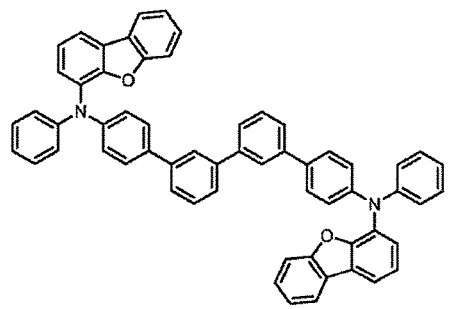
FIG. 10 is a view showing the structural formulas of Compounds (1-33) to (1-36) in the arylamine compound of the general formula (1).
Figure 10:
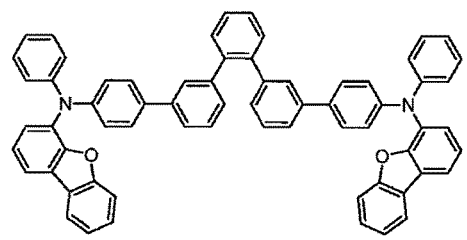
Figure 10:
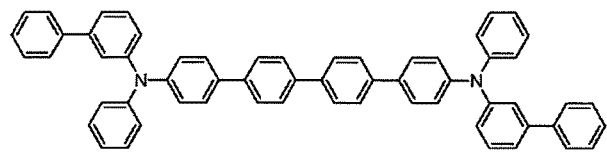
Figure 10:
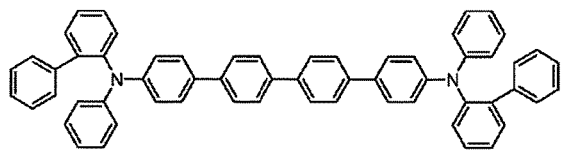
Figure 11:
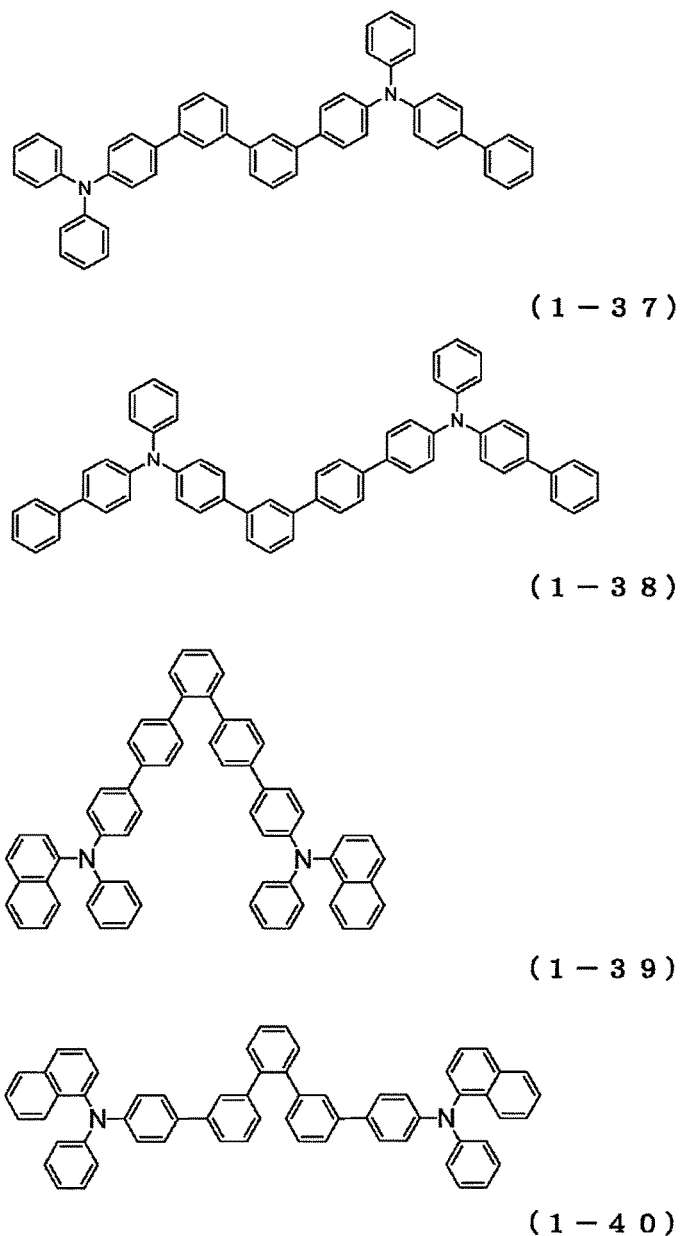
FIG. 11 is a view showing the structural formulas of Compounds (1-37) to (1-40) in the arylamine compound of the general formula (1).
Figure 12:
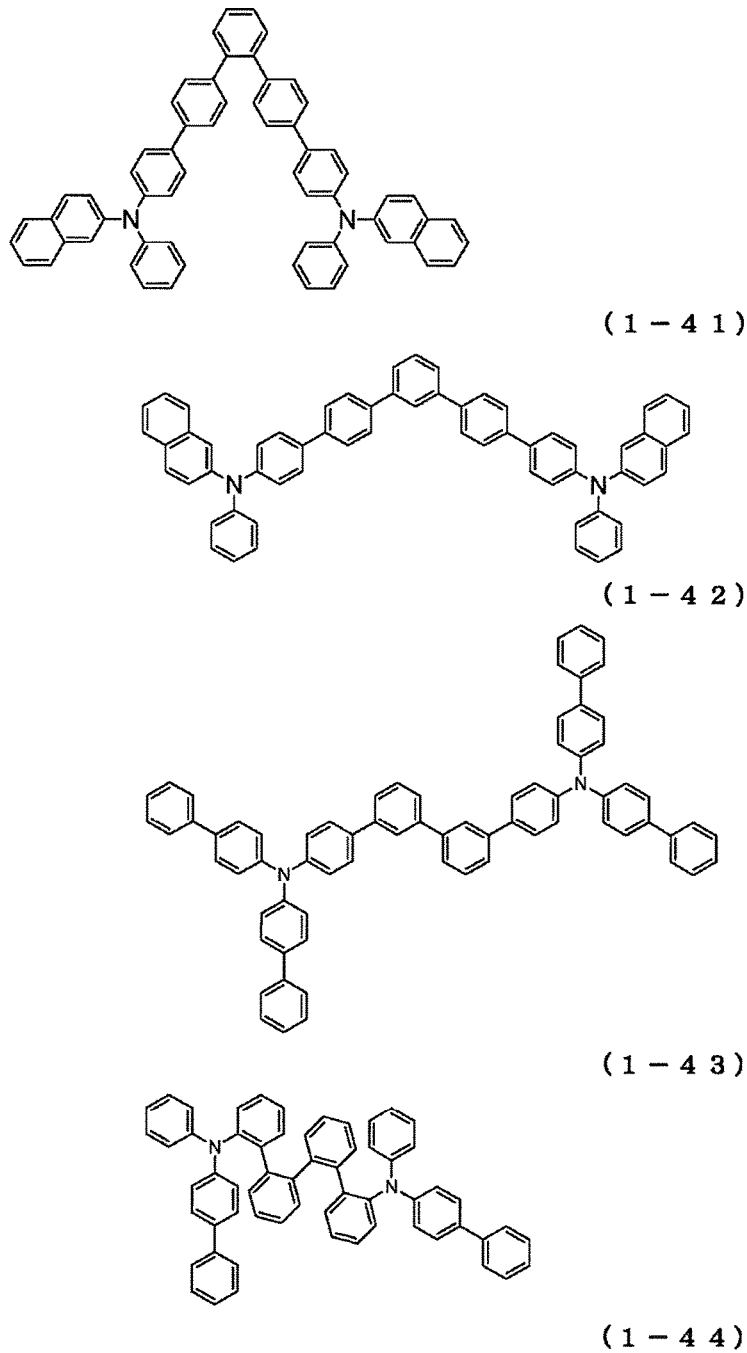
FIG. 12 is a view showing the structural formulas of Compounds (1-41) to (1-44) in the arylamine compound of the general formula (1).

The organic EL device of the present invention has a basic structure in which at least an anode, a hole injection layer, a first hole transport layer, a second hole transport layer, a luminous layer, an electron transport layer, and a cathode are formed, in order of description, on a transparent substrate such as a glass substrate or a plastic substrate (for example, a polyethylene terephthalate substrate). The layered structure can be in various forms, provided that it has such a basic structure. For example, an electron blocking layer can be provided between the second hole transport layer and the luminous layer, a hole blocking layer can be provided between the luminous layer and the electron transport layer, or an electron injection layer can be provided between the electron transport layer and the cathode. Further, some of the organic layers can be omitted or combined together. For example, a configuration can be used in which the electron injection layer and the electron transport layer are combined together. FIG. 1 illustrates a layered structure used in the below-described Device Examples. In this example, an anode 2, a hole injection layer 3, a first hole transport layer 4, a second hole transport layer 5, a luminous layer 6, an electron transport layer 7, an electron injection layer 8, and a cathode 9 are formed, in the order of description, on a transparent substrate 1.

The important feature of the organic EL device of the present invention is that among the abovementioned layers, the second hole transport layer 5 includes the arylamine compound represented by a general formula (1) and the electron transport layer 7 includes the pyrimidine derivative represented by a general formula (2). The arylamine compound represented by the general formula (1) and the pyrimidine derivative represented by the general formula (2) will be described hereinbelow.

The arylamine compound represented by the general formula (1);

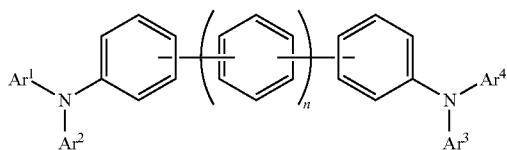

(1)

As will also be understood from the below-described Examples, such an arylamine compound has a high glass transition temperature Tg (for example, 100° C. or higher), and therefore is stable in a thin-film state and excellent in heat resistance. Further, it has a high work function as compared with the work function (about 5.4 eV) of a general hole transport material. Therefore, such an arylamine compound excels in hole transport property and has high hole mobility and a satisfactory hole injection characteristic. Furthermore, such an arylamine compound excels in electron blocking property.

In the general formula (1), n represents an integer of 2 to 4. From the viewpoint of hole transport capacity, an integer of 2 or 3 is preferred.

$Ar^1$ to $Ar^4$ each represent an aromatic hydrocarbon group, an aromatic heterocyclic group, or a condensed polycyclic aromatic group.

Specific examples of the aromatic hydrocarbon group, aromatic heterocyclic group, or condensed polycyclic aromatic group represented by $Ar^1$ to $Ar^4$ include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group, etc. It is preferred that $Ar^1$ to $Ar^4$ be present independently from each other, but $Ar^1$ and $Ar^2$ or $Ar^3$ and $Ar^4$ may be bonded to each other via a single bond, a substituted or unsubstituted methylene group, an oxygen atom, or a sulfur atom to form a ring.

The preferred aromatic heterocyclic group represented by $Ar^1$ to $Ar^4$ include a sulfur-containing aromatic heterocyclic group, for example, a thienyl group, a benzothienyl group, a benzothiazolyl group, and a dibenzothienyl group; an oxygen-containing aromatic heterocyclic group, for example, a furyl group, a pyrrolyl group, a benzofuranyl group, a benzoxazolyl group, and a dibenzofuranyl group; or an N-substituted carbazolyl group having a substituent selected from the exemplified aromatic hydrocarbon groups and condensed polycyclic aromatic groups.

The aromatic hydrocarbon group, aromatic heterocyclic group, or condensed polycyclic aromatic group may have a substituent. Specific examples of the substituents include the following groups, in addition to a deuterium atom, a cyano group, and a nitro group.

a halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group;

an aromatic heterocyclic group, for example, a pyridyl group, a furyl group, a thienyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group;

an arylvinyl group, for example, a styryl group and a naphthylvinyl group; and an acyl group, for example, an acetyl group and a benzoyl group;

Further, the alkyl groups having 1 to 6 carbon atoms and alkyloxy groups having 1 to 6 carbon atoms may be straight-chain or branched. The above substituents may further have the substituents exemplified hereinabove. Further, the above substituents may be present individually, or may be bonded to each other via a single bond, a substituted or unsubstituted methylene group, an oxygen atom, or a sulfur atom to form a ring.

The arylamine compounds represented by the general formula (1) can be synthesized by a publicly known method such as the Suzuki coupling.

The produced arylamine compound is purified by, for example, column chromatography purification, adsorption purification with silica gel, activated carbon, activated clay, and the like, or recrystallization or crystallization with a solvent, and finally purified by sublimation purification, or the like. Identification of the compounds can be performed by NMR analysis.

The glass transition temperature (Tg) and work function can be measured as physical property values. The glass transition temperature (Tg) is an indicator of stability in a thin-film state. The glass transition temperature (Tg) can be determined with a high-sensitivity differential scanning calorimeter (DSC3100S, manufactured by Bruker AXS K.K.) by using a powder.

The work function is an indicator of hole transport property. The work function can be determined with an ionization potential measuring device (PYS-202, manufactured by Sumitomo Heavy Industries, Ltd.) by producing a 100 nm thin film on an ITO substrate.

As the $Ar^1$ to $Ar^4$, aromatic hydrocarbon groups, oxygen-containing aromatic heterocyclic group, or condensed polycyclic aromatic groups is preferred, and a phenyl group, a biphenylyl group, a terphenylyl group, a naphthyl group, a phenanthrenyl group, a fluorenyl group, or a dibenzofuranyl group are more preferred.

It is preferred that $Ar^1$ and $Ar^2$ be different groups or that $Ar^3$ and $Ar^4$ be different groups, and it is more preferred that $Ar^1$ and $Ar^2$ be different groups and $Ar^3$ and $Ar^4$ be different groups.

From the viewpoint of the stability of the thin film which affects the device life, it is preferred that the bonding mode of the phenylene groups in the general formula (1) be a mixture of 1,2-bonds or 1,3-bonds with 1,4-bonds, rather than only 1,4-bonds. Examples of arylamine derivatives in which 4 (n is 2), 5 (n is 3), or 6 (n is 4) phenylene groups are linked with each other and the link of the phenylene groups is not linear are presented below.

1,1':3',1":3",1'''-quaterphenyldiamine
1,1':3',1":2",1''':3''',1''''-kinkphenyldiamine
1,1':3',1":3",1''':3''',1''''-kinkphenyldiamine
1,1':2',1":2",1'''-quaterphenyldiamine
1,1':3',1":4",1'''-quaterphenyldiamine
1,1':4',1":2",1''':4''',1''''-kinkphenyldiamine
1,1':2',1":3",1''':2''',1''''-kinkphenyldiamine
1,1':4',1":3",1''':4''',1''''-kinkphenyldiamine
1,1':2',1":2",1''':2''',1''''-kinkphenyldiamine Specific examples of preferred compounds among the arylamine compounds represented by the general formula (1) are shown in FIGS. 2 to 12, but the arylamine compounds represented by the general formula (1) are not limited to these compounds. D in the structural formula represents deuterium.

The pyrimidine derivative represented by the general formula (2);

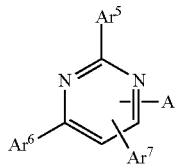

(2)

such a pyrimidine compound excels in electron injection capacity and transport capacity and is a compound preferred as a material for the electron transport layer.

In the general formula (2), $Ar^5$ represents an aromatic hydrocarbon group, an aromatic heterocyclic group, or a condensed polycyclic aromatic group, and $Ar^6$ and $Ar^7$ each represent a hydrogen atom, an aromatic hydrocarbon group, an aromatic heterocyclic group, or a condensed polycyclic aromatic group. $Ar^6$ and $Ar^7$ may not each be a hydrogen atom at the same time.

Specific examples of the aromatic hydrocarbon group, aromatic heterocyclic group, or condensed polycyclic aromatic group represented by $Ar^5$ to $Ar^7$ include a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a spirobifluorenyl group, a furyl group, a thienyl group, a benzofuranyl group, a benzothienyl group, a dibenzofuranyl group, and a dibenzothienyl group.

The aromatic hydrocarbon group, aromatic heterocyclic group, or condensed polycyclic aromatic group represented by $Ar^5$ to $Ar^7$ may have a substituent. Specific examples of the substituents include the following groups, in addition to a deuterium atom, a cyano group, and a nitro group.

a halogen atom, for example, a fluorine atom, a chlorine atom, a bromine atom, and an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, and an n-hexyl group;

an alkyloxy group having 1 to 6 carbon atoms, for example, a methyloxy group, an ethyloxy group, and a propyloxy group;

an alkenyl group, for example, a vinyl group and an allyl group;

an aryloxy group, for example, a phenyloxy group and a tolyloxy group;

an arylalkyloxy group, for example, a benzyloxy group and a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, and a spirobifluorenyl group;

an aromatic heterocyclic group, for example, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a carbolinyl group, an azaspirobifluorenyl group, and a diazaspirobifluorenyl group;

an arylvinyl group, for example, a styryl group and a naphthylvinyl group; and an acyl group, for example, an acetyl group and a benzoyl group;

Further, the alkyl groups having 1 to 6 carbon atoms and alkyloxy groups having 1 to 6 carbon atoms may be straight-chain or branched. The above substituents may further have the substituents exemplified hereinabove. Further, the above substituents may be present individually, or may be bonded to each other via a single bond, a substituted or unsubstituted methylene group, an oxygen atom, or a sulfur atom to form a ring, and these substituents and $Ar^5$, $Ar^6$, or $Ar^7$, to which the substituents are bonded, may be bonded to each other via an oxygen atom, a sulfur atom, or a substituted or unsubstituted methylene group, to form a ring.

In the general formula (2), A represents a mono valent group indicated by the following structural formula (3).

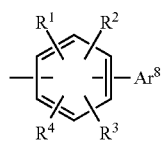

(3)

In the structural formula (3), $Ar^8$ represents an aromatic heterocyclic group. Specific examples of the aromatic heterocyclic group represented by $Ar^8$ include a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, an azaspirobifluorenyl group, and a diazaspirobifluorenyl group, etc.

The aromatic heterocyclic group represented by $Ar^8$ may have a substituent. The substituents can be exemplified by the same ones as those illustrated as the substituents optionally possessed by the aromatic hydrocarbon group, aromatic heterocyclic group, or condensed polycyclic aromatic group represented by $Ar^5$ to $Ar^7$ in the general formula (2). Modes which the substituents can adopt are also the same.

In the structural formula (3), the phenyl group and $Ar^8$ may be present independently from each other, or they may be bonded to each other via a substituted or unsubstituted methylene group to form a ring, as in an Exemplary Compound 2-248 or 2-249 exemplified hereinbelow.

$R^1$ to $R^4$ each represent a hydrogen atom, a deuterium atom, a fluorine atom, a chlorine atom, a cyano group, a trifluoromethyl group, an alkyl group having 1 to 6 carbon atoms, an aromatic hydrocarbon group, an aromatic heterocyclic group, or a condensed polycyclic aromatic group. $R^1$ to $R^4$ and the aforementioned $Ar^8$ may be present independently from each other, or they may be bonded to each other via a single bond, a substituted or unsubstituted methylene group, an oxygen atom, or a sulfur atom to form a ring.

The alkyl groups having 1 to 6 carbon atoms and represented by $R^1$ to $R^4$ may be straight-chain or branched and examples thereof include a methyl group, an ethyl group, an n-propyl group, an i-propyl group, an n-butyl group, a 2-methylpropyl group, a t-butyl group, an n-pentyl group, a 3-methylbutyl group, a tert-pentyl group, an n-hexyl group, an iso-hexyl group, a tert-hexyl group, etc.

Specific examples of the aromatic hydrocarbon group, aromatic heterocyclic group, or condensed polycyclic aromatic group represented by $R^1$ to $R^4$ include a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a spirobifluorenyl group, a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, a phenoxazinyl group, a phenothiazinyl group, a phenazinyl group, an azaspirobifluorenyl group, and a diazaspirobifluorenyl group, etc.

The aromatic hydrocarbon group, aromatic heterocyclic group, or condensed polycyclic aromatic group represented by $R^1$ to $R^4$ may have a substituent. The substituents can be exemplified by the same ones as those illustrated as the substituents optionally possessed by the aromatic hydrocarbon group, aromatic heterocyclic group, or condensed polycyclic aromatic group represented by $Ar^5$ to $Ar^7$ in the general formula (2). Modes which the substituents can adopt are also the same.

The preferred forms of the pyrimidine derivative represented by the general formula (2) are presented in 1) to 14) below.

1) This pyrimidine derivative is represented by the following general formula (2a).

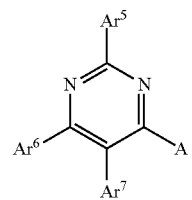

(2a)

In this formula, $Ar^5$ to $Ar^7$ and A are as defined in the general formula (2).

2) This pyrimidine derivative is represented by the following general formula (2b).

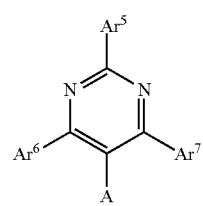

(2b)

In this formula, $Ar^5$ to $Ar^7$ and A are as defined in the general formula (2).

3) A is the monovalent group indicated by the following structural formula (3a). This form is preferred from the viewpoint of thin film stability.

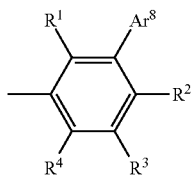

(3a)

In this formula, Ar$^8$ and R$^1$ to R$^4$ are as defined in the structural formula (3).

4) A is the monovalent group indicated by the following structural formula (3b).

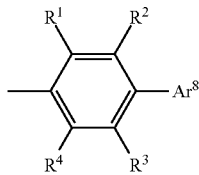

(3b)

In this formula, Ar$^8$ and R$^1$ to R$^4$ are as defined in the structural formula (3).

5) Ar$^5$ represents an aromatic hydrocarbon group or a condensed polycyclic aromatic group, Ar$^6$ and Ar$^7$ each represent a hydrogen atom, an aromatic hydrocarbon group or a condensed polycyclic aromatic group.

6) Ar$^6$ is a phenyl group having a substituent.

7) Ar$^6$ is a phenyl group having a substituent, and the substituent is a substituted or unsubstituted aromatic hydrocarbon group or a substituted or unsubstituted condensed polycyclic aromatic group.

8) Ar$^6$ is a phenyl group having a substituent, and the substituent is a substituted or unsubstituted aromatic hydrocarbon group.

9) Ar$^6$ is a phenyl group having a substituent, and the substituent is a substituted or unsubstituted condensed polycyclic aromatic group.

10) Ar$^7$ is a hydrogen atom.

11) Ar$^5$ is a phenyl group having a substituent.

12) Ar$^5$ is a phenyl group having a substituent, and the substituent is a substituted or unsubstituted condensed polycyclic aromatic group.

13) Ar$^5$ is a substituted or unsubstituted condensed polycyclic aromatic group.

14) Ar$^5$ is an unsubstituted phenyl group.

Ar$^5$ in the general formula (2) is preferably a phenyl group; a biphenylyl group; a naphthyl group; an anthracenyl group; an acenaphthenyl group; a phenanthrenyl group; a fluorenyl group; an indenyl group; a pyrenyl group; a perylenyl group; a fluoranthenyl group; a triphenylenyl group; a spirobifluorenyl group; an oxygen-containing aromatic heterocyclic group, for example, a furyl group, a benzofuranyl group, and a dibenzofuranyl group; or a sulfur-containing aromatic heterocyclic group, for example, a thienyl group, a benzothienyl group, and a dibenzothienyl group; and more preferably a phenyl group, a biphenylyl group, a naphthyl group, a phenanthrenyl group, a fluorenyl group, a pyrenyl group, a fluoranthenyl group, a triphenylenyl group, a spirobifluorenyl group, a dibenzofuranyl group, and a dibenzothienyl group. Here, it is preferred that the phenyl group have a substituted or unsubstituted condensed polycyclic aromatic group, or a phenyl group as a substituent, and it is more preferred that the phenyl group have a naphthyl group, a phenanthrenyl group, a pyrenyl group, a fluoranthenyl group, a triphenylenyl group, a spirobifluorenyl group, or a phenyl group as a substituent. Furthermore, it is also preferred that the substituent possessed by the phenyl group and the phenyl group be bonded via an oxygen atom or a sulfur atom to form a ring.

Ar$^6$ is preferably a phenyl group having a substituent; a substituted or unsubstituted spirobifluorenyl group; an oxygen-containing aromatic heterocyclic group, for example, a furyl group, a benzofuranyl group, and a dibenzofuranyl group; or a sulfur-containing aromatic heterocyclic group, for example, a thienyl group, a benzothienyl group, and a dibenzothienyl group.

The substituent possessed by the phenyl group in this case is preferably an aromatic hydrocarbon group, for example, a phenyl group, a biphenylyl group, and a terphenyl group; a condensed polycyclic aromatic group, for example, a naphthyl group, an acenaphthenyl group, a phenanthrenyl group, a fluorenyl group, an indenyl group, a pyrenyl group, a perylenyl group, a fluoranthenyl group, a triphenylenyl group, and a spirobifluorenyl group; an oxygen-containing aromatic heterocyclic group, for example, a furyl group, a benzofuranyl group, and a dibenzofuranyl group; or a sulfur-containing aromatic heterocyclic group, for example, a thienyl group, a benzothienyl group, and a dibenzothienyl group; and more preferably a phenyl group, a naphthyl group, a phenanthrenyl group, a fluorenyl group, a pyrenyl group, a fluoranthenyl group, a triphenylenyl group, a spirobifluorenyl group, a dibenzofuranyl group, and a dibenzothienyl group. Furthermore, it is also preferred that the substituent possessed by the phenyl group and the phenyl group be bonded via an oxygen atom or a sulfur atom to form a ring.

Ar$^7$ is preferably a hydrogen atom; a phenyl group having a substituent; a substituted or unsubstituted spirobifluorenyl group; an oxygen-containing aromatic heterocyclic group, for example, a furyl group, a benzofuranyl group, and a dibenzofuranyl group; or a sulfur-containing aromatic heterocyclic group, for example, a thienyl group, a benzothienyl group, and a dibenzothienyl group. The substituent possessed by the phenyl group in this case is preferably an aromatic hydrocarbon group, for example, a phenyl group, a biphenylyl group, and a terphenyl group; a condensed polycyclic aromatic group, for example, a naphthyl group, an acenaphthenyl group, a phenanthrenyl group, a fluorenyl group, an indenyl group, a pyrenyl group, a perylenyl group, a fluoranthenyl group, a triphenylenyl group, and a spirobifluorenyl group; an oxygen-containing aromatic heterocyclic group, for example, a furyl group, a benzofuranyl group, and a dibenzofuranyl group; or a sulfur-containing aromatic heterocyclic group, for example, a thienyl group, a benzothienyl group, and a dibenzothienyl group; and more preferably a phenyl group, a naphthyl group, a phenanthrenyl group, a fluorenyl group, a pyrenyl group, a fluoranthenyl group, a triphenylenyl group, a spirobifluorenyl group, a dibenzofuranyl group, and a dibenzothienyl group. Furthermore, it is also preferred that the substituent possessed by the phenyl group and the phenyl group be bonded via an oxygen atom or a sulfur atom to form a ring.

Ar$^8$ is preferably a nitrogen-containing aromatic heterocyclic group, for example, a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, an azafluorenyl group, a diazafluorenyl group, a naphthyridinyl group, a phenanthrolinyl group, an acridinyl group, a carbolinyl group, an azaspirobifluorenyl group, and a diazaspirobifluorenyl group, more preferably a triazinyl group, a pyridyl group, a pyrimidinyl group, a quinolyl group, an isoquinolyl group, an indolyl group, a quinoxalinyl group, an azafluorenyl group, a diazafluorenyl group, a benzimidazolyl group, a naphthyridinyl group, a phenanthrolinyl group, an acridinyl group, an azaspirobifluorenyl group, and a diazaspirobifluorenyl group, and particularly preferably a pyridyl group, a pyrimidinyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, and a diazaspirobifluorenyl group.

In the general formula (2), $Ar^5$ and $Ar^6$ may be the same, but from the viewpoint of thin film stability, it is preferred that they be different. The mode in which $Ar^5$ and $Ar^6$ are the same group includes a mode in which they have different substituents and also a mode in which the substituents are at different positions.

In the general formula (2), $Ar^6$ and $Ar^7$ may be the same group, but the increase in symmetry of the entire molecule can facilitate crystallization, therefore, from the standpoint of thin film stability, it is preferred that $Ar^6$ and $Ar^7$ be different groups. It is also preferred that one of $Ar^6$ and $Ar^7$ be a hydrogen atom.

Figure 13:
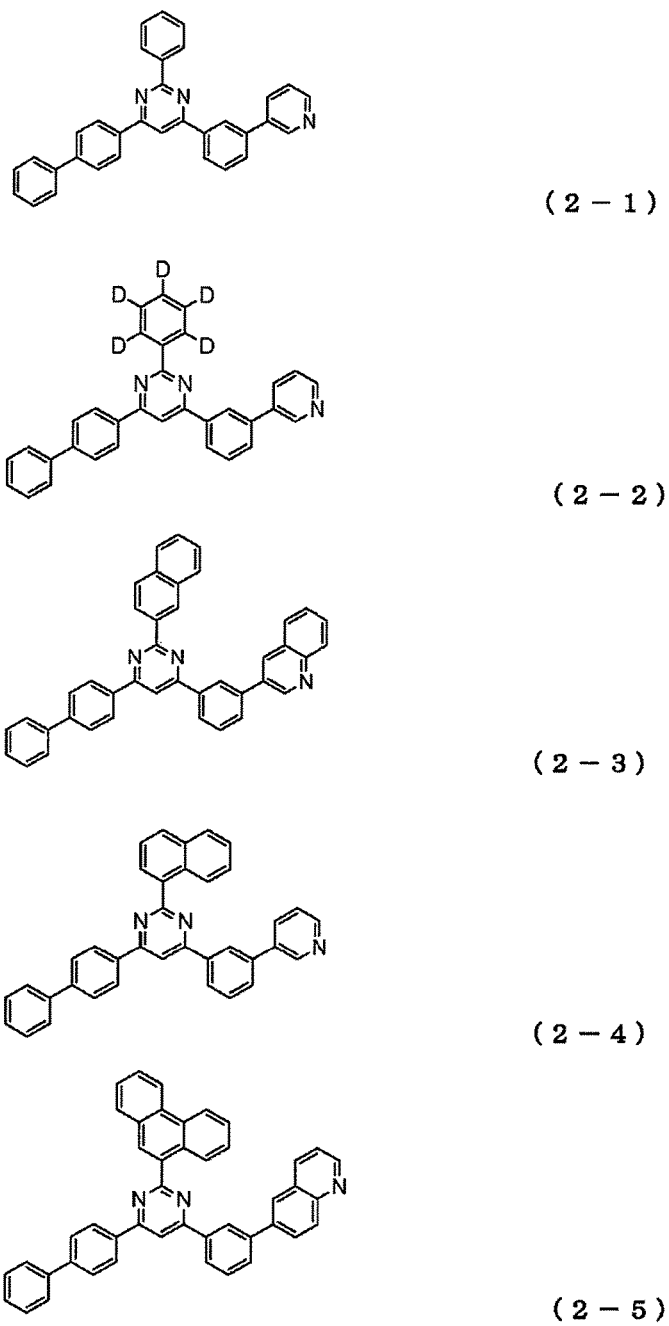
FIG. 13 is a view showing the structural formulas of Compounds (2-1) to (2-5) in the pyrimidine derivative of a general formula (2).
Figure 14:
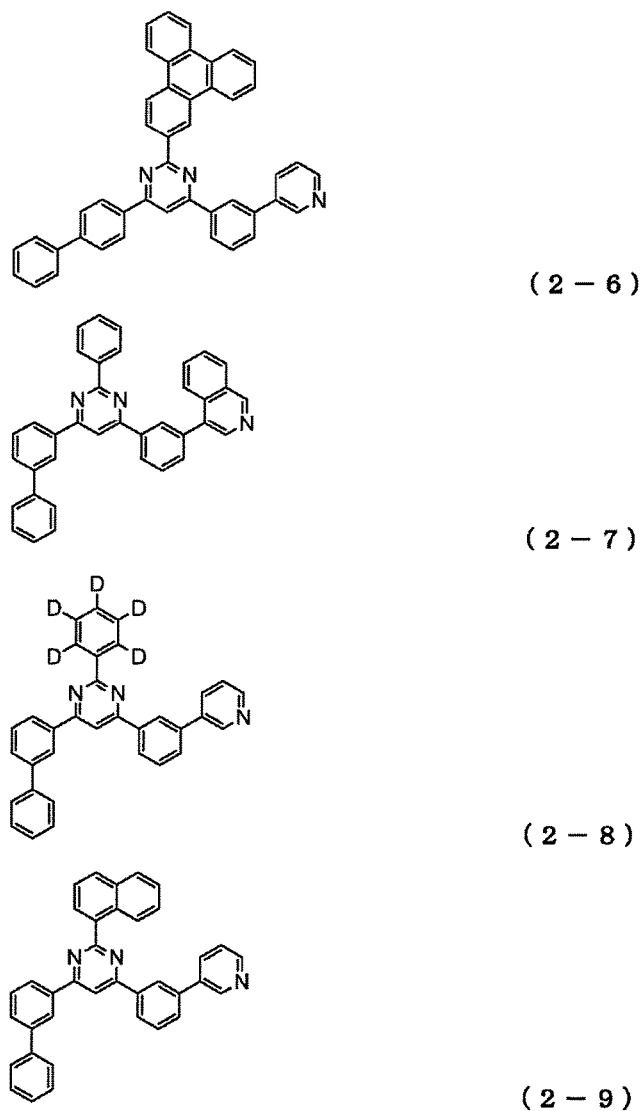
FIG. 14 is a view showing the structural formulas of Compounds (2-6) to (2-9) in the pyrimidine derivative of the general formula (2).
Figure 15:
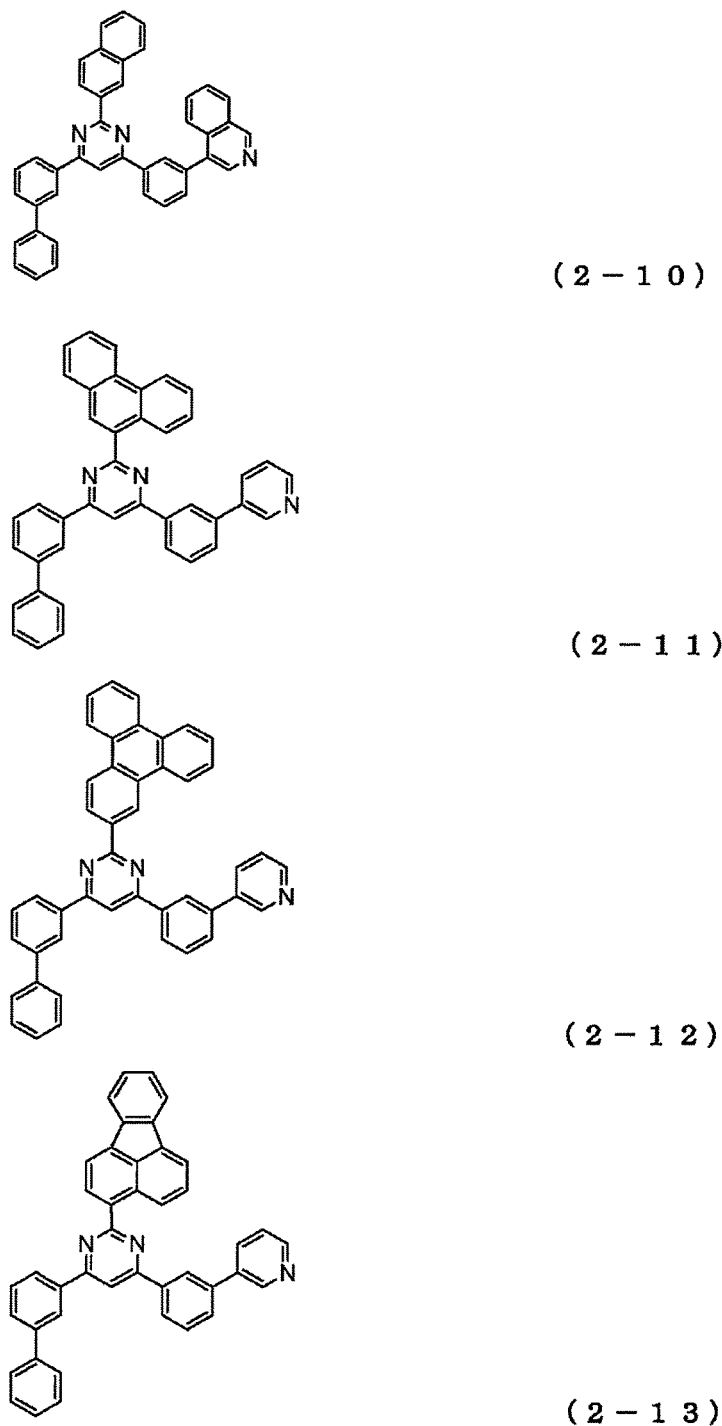
FIG. 15 is a view showing the structural formulas of Compounds (2-10) to (2-13) in the pyrimidine derivative of the general formula (2).
Figure 16:
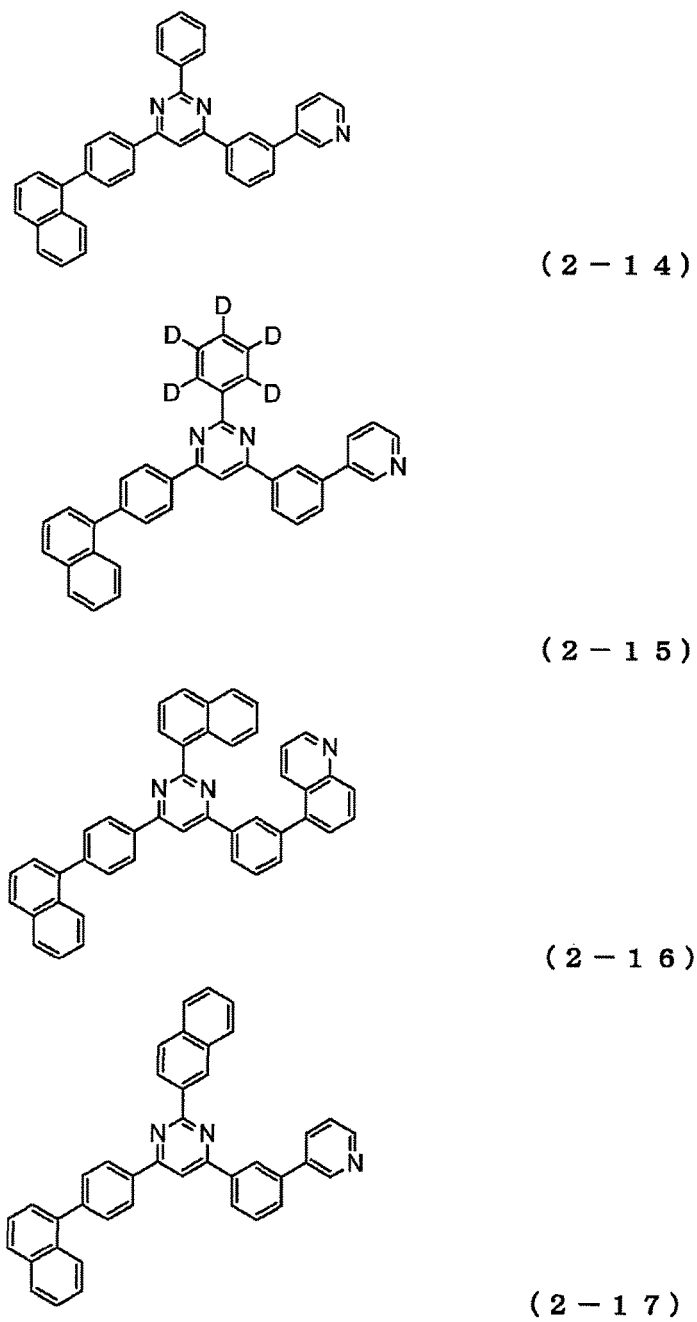
FIG. 16 is a view showing the structural formulas of Compounds (2-14) to (2-17) in the pyrimidine derivative of the general formula (2).
Figure 17:
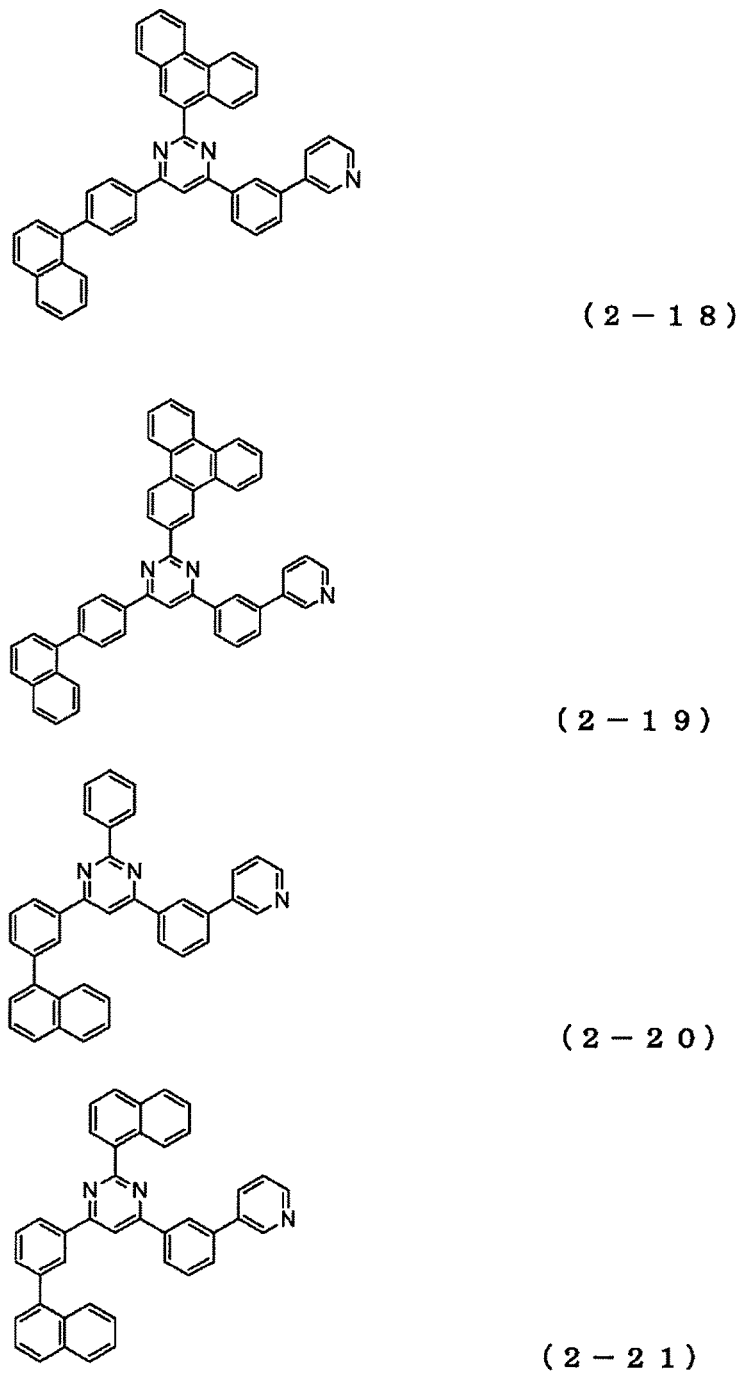
FIG. 17 is a view showing the structural formulas of Compounds (2-18) to (2-21) in the pyrimidine derivative of the general formula (2).
Figure 18:
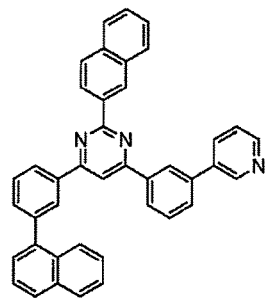
FIG. 18 is a view showing the structural formulas of Compounds (2-22) to (2-25) in the pyrimidine derivative of the general formula (2).
Figure 18:
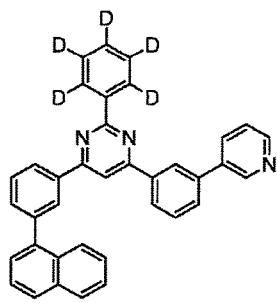
Figure 18:
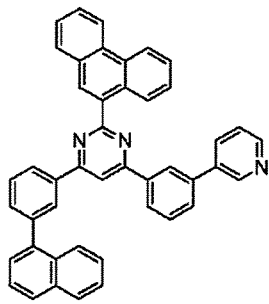
Figure 18:
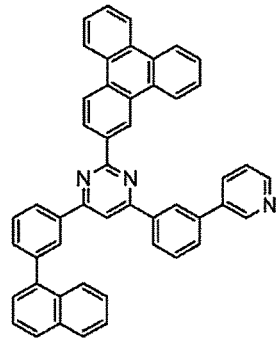
Figure 19:
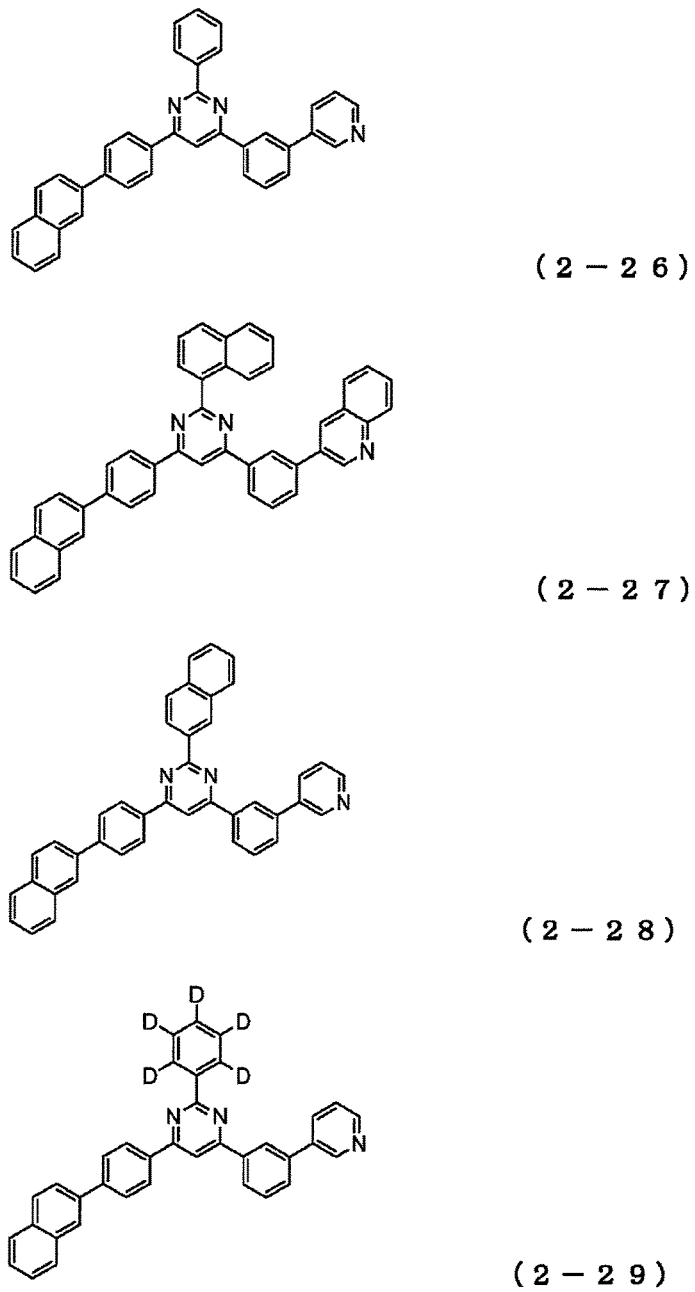
FIG. 19 is a view showing the structural formulas of Compounds (2-26) to (2-29) in the pyrimidine derivative of the general formula (2).
Figure 20:
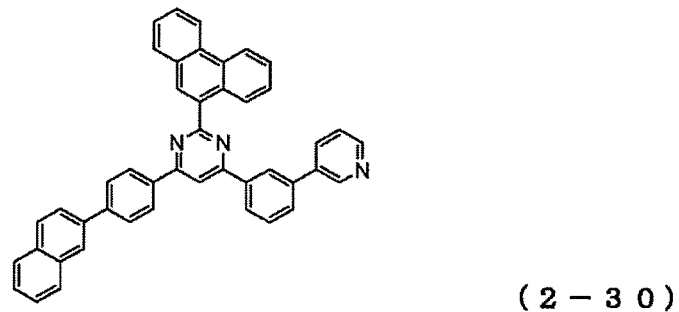
FIG. 20 is a view showing the structural formulas of Compounds (2-30) to (2-33) in the pyrimidine derivative of the general formula (2).
Figure 20:
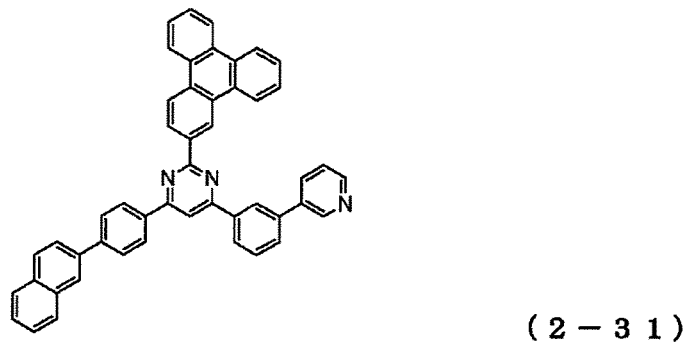
Figure 20:
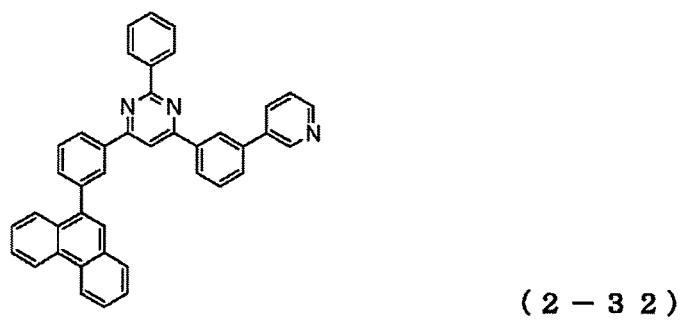
Figure 20:
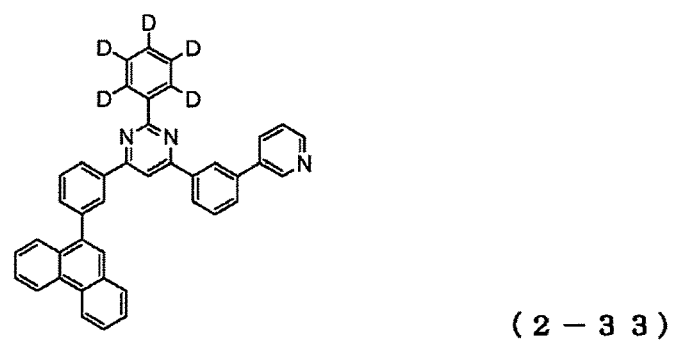
Figure 21:
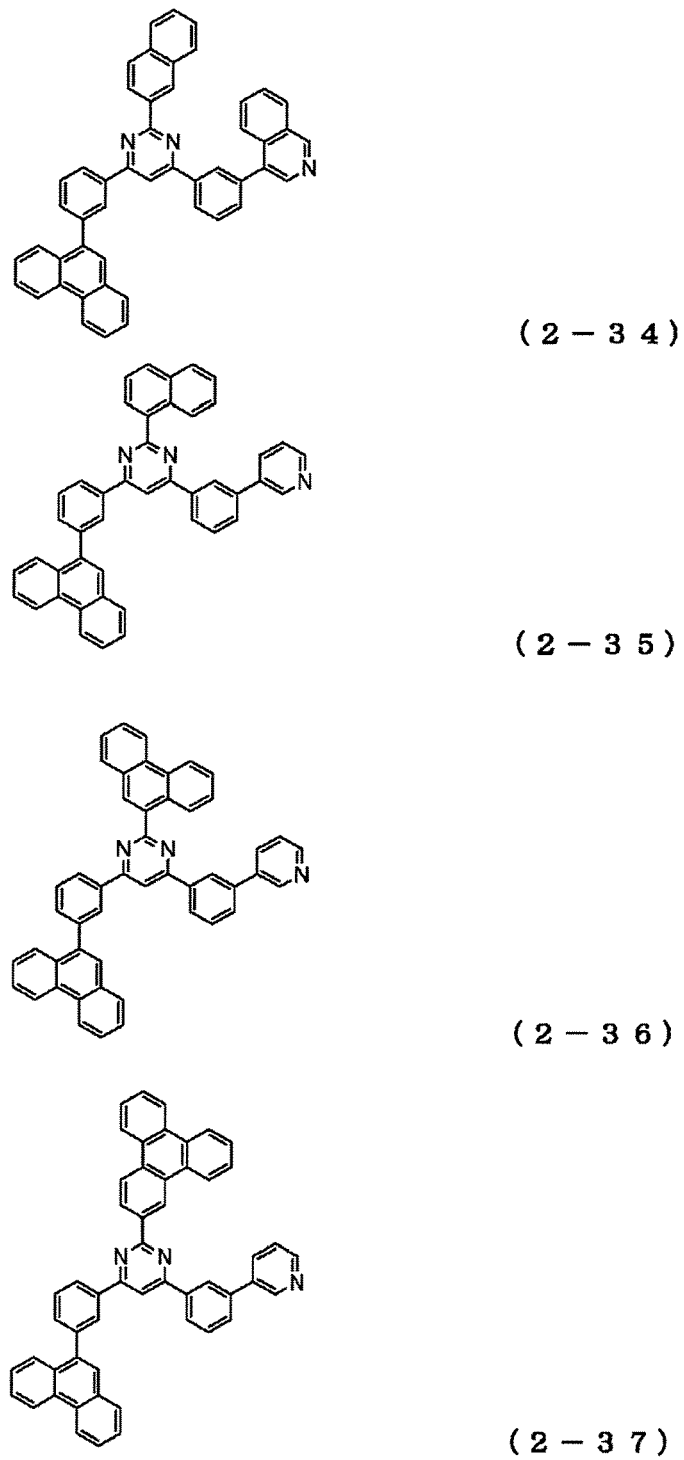
FIG. 21 is a view showing the structural formulas of Compounds (2-34) to (2-37) in the pyrimidine derivative of the general formula (2).
Figure 22:
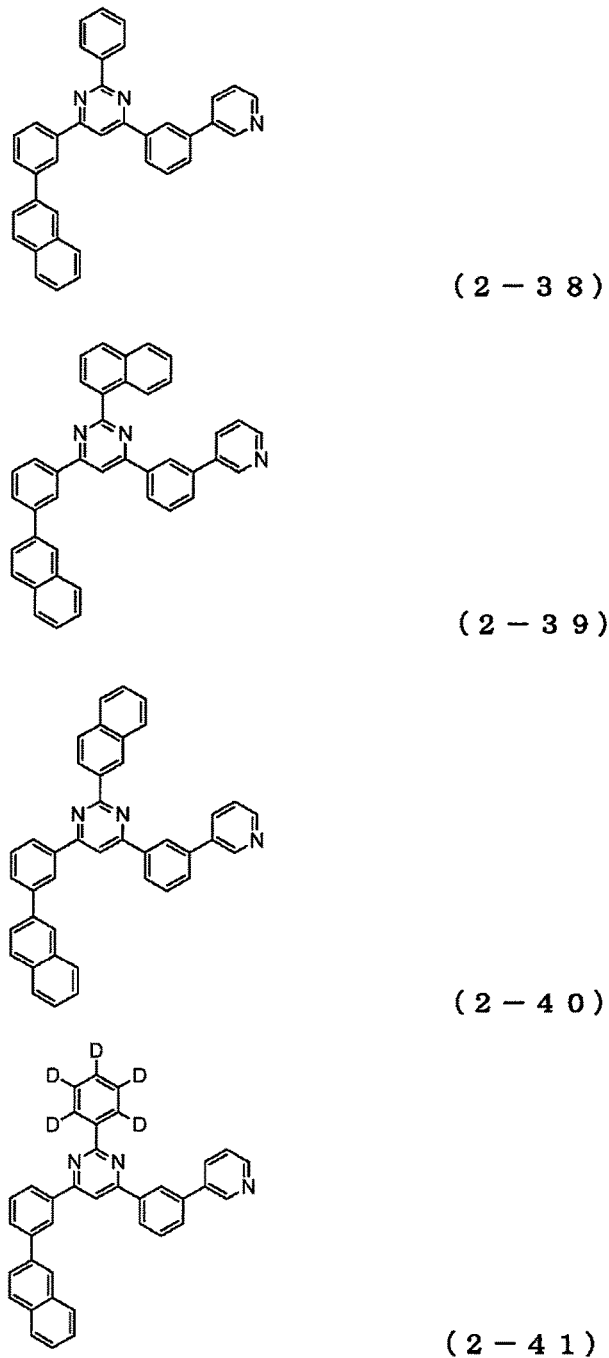
FIG. 22 is a view showing the structural formulas of Compounds (2-38) to (2-41) in the pyrimidine derivative of the general formula (2).
Figure 23:
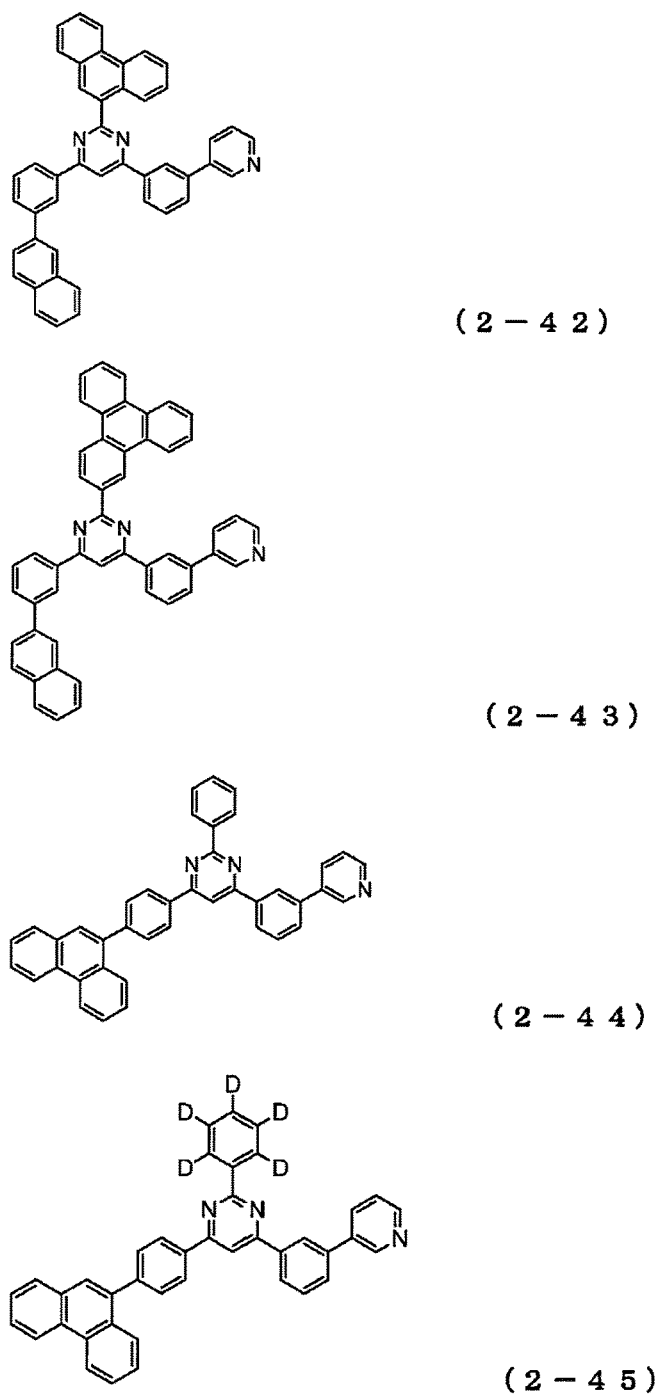
FIG. 23 is a view showing the structural formulas of Compounds (2-42) to (2-45) in the pyrimidine derivative of the general formula (2).
Figure 24:
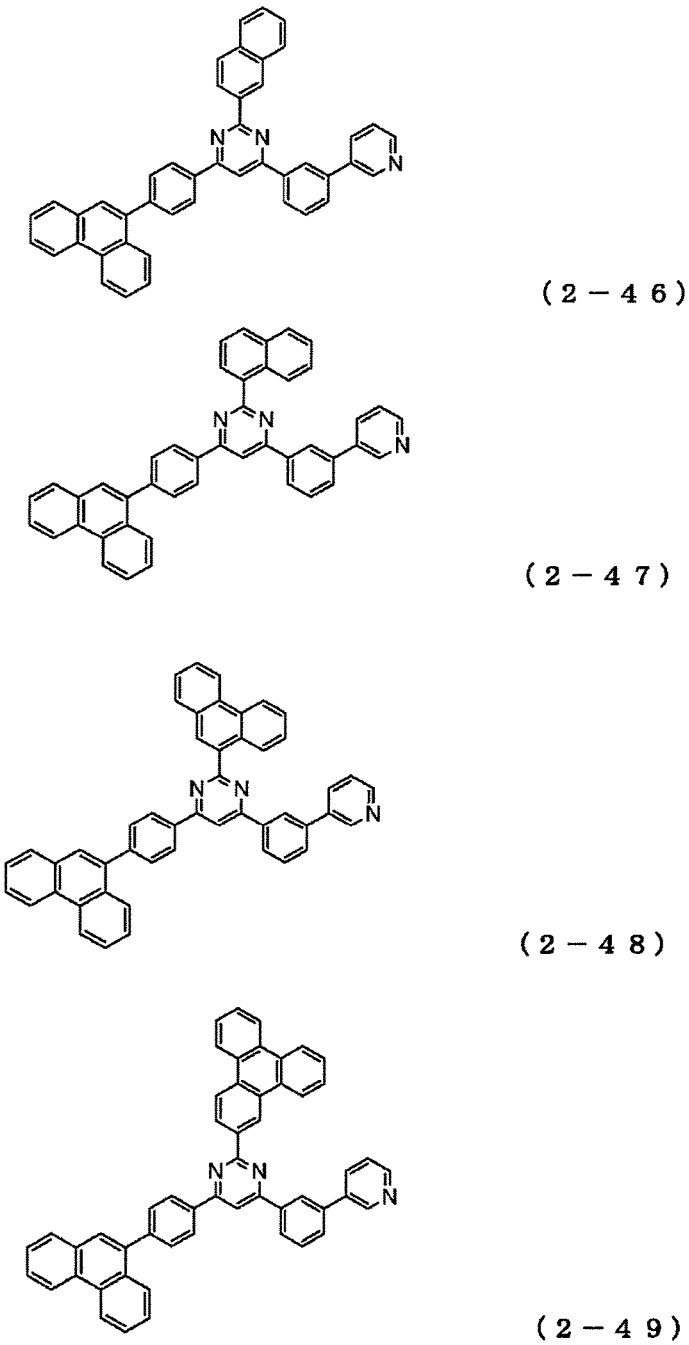
FIG. 24 is a view showing the structural formulas of Compounds (2-46) to (2-49) in the pyrimidine derivative of the general formula (2).
Figure 25:
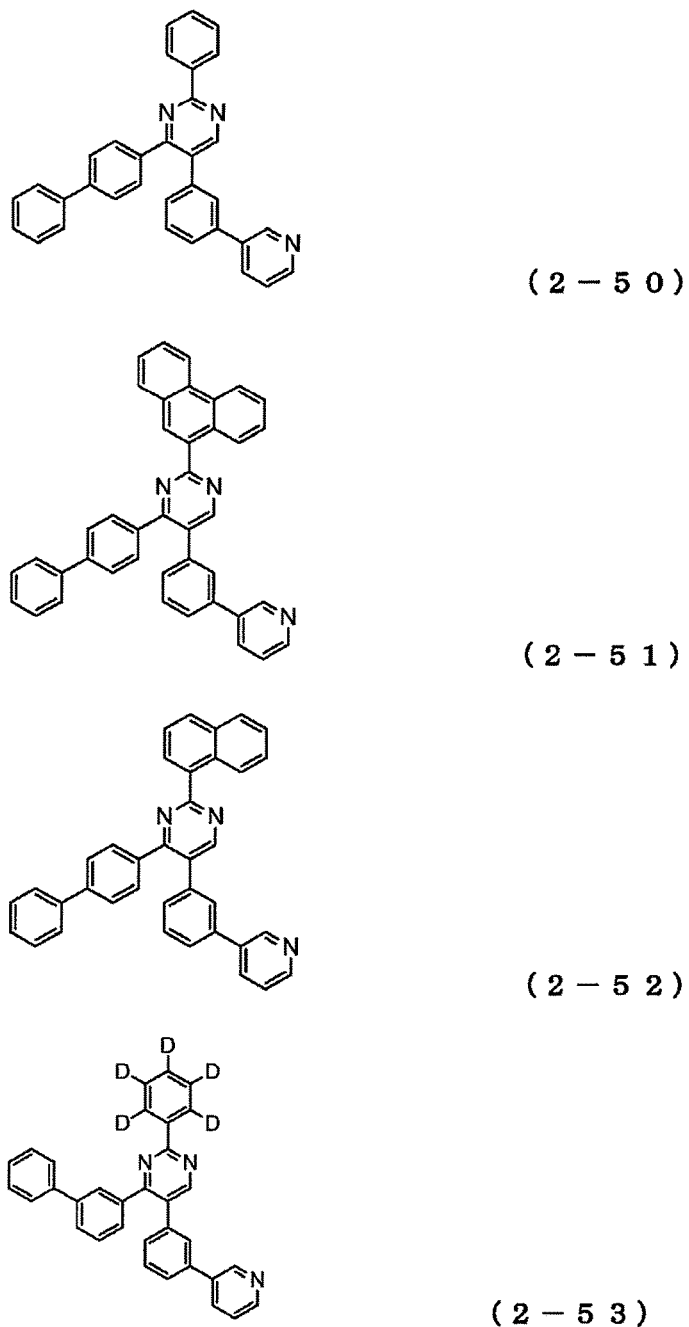
FIG. 25 is a view showing the structural formulas of Compounds (2-50) to (2-53) in the pyrimidine derivative of the general formula (2).
Figure 26:
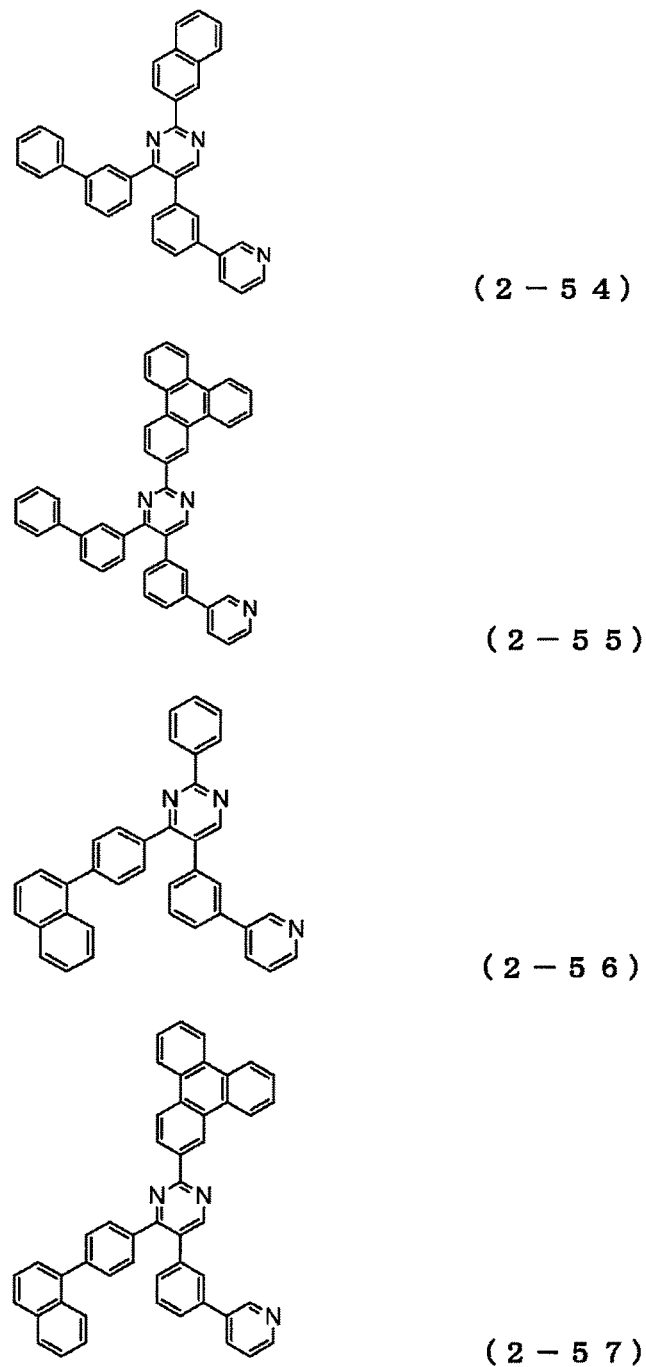
FIG. 26 is a view showing the structural formulas of Compounds (2-54) to (2-57) in the pyrimidine derivative of the general formula (2).
Figure 27:
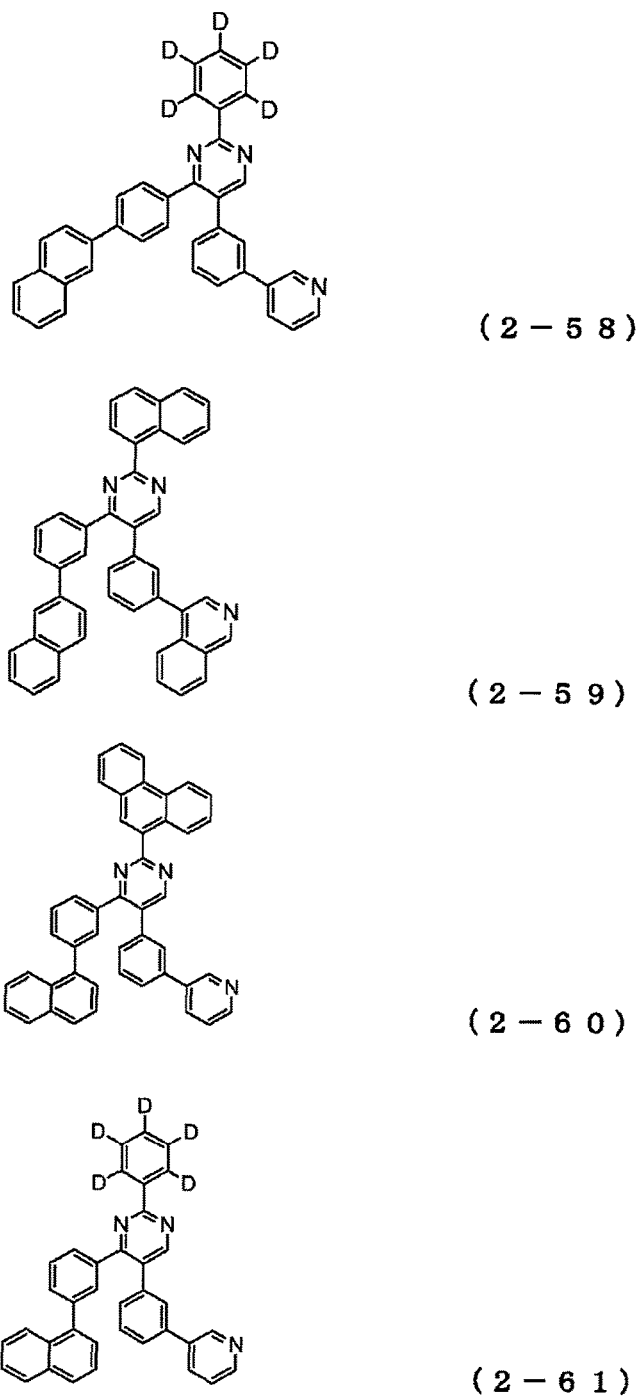
FIG. 27 is a view showing the structural formulas of Compounds (2-58) to (2-61) in the pyrimidine derivative of the general formula (2).
Figure 28:
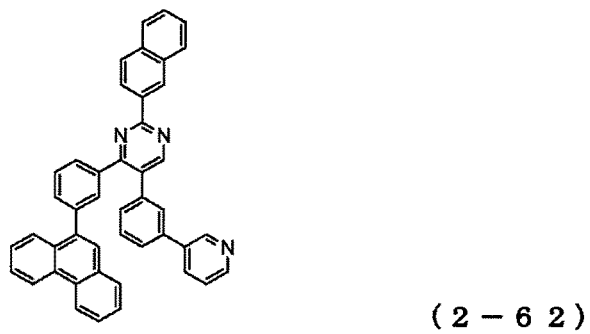
FIG. 28 is a view showing the structural formulas of Compounds (2-62) to (2-65) in the pyrimidine derivative of the general formula (2).
Figure 28:
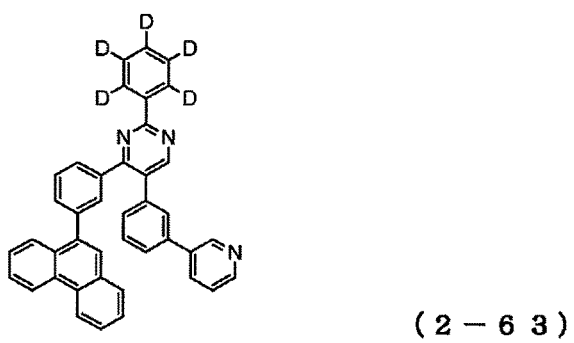
Figure 28:
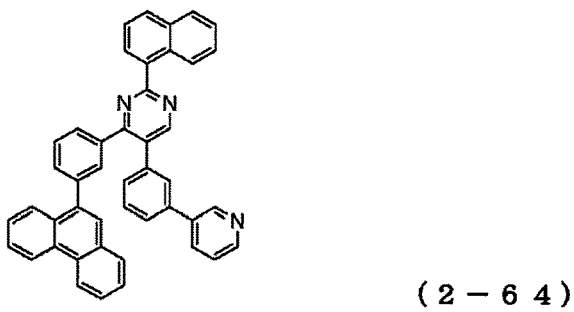
Figure 28:
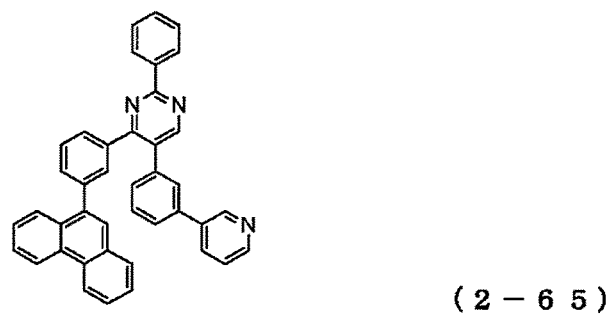
Figure 29:
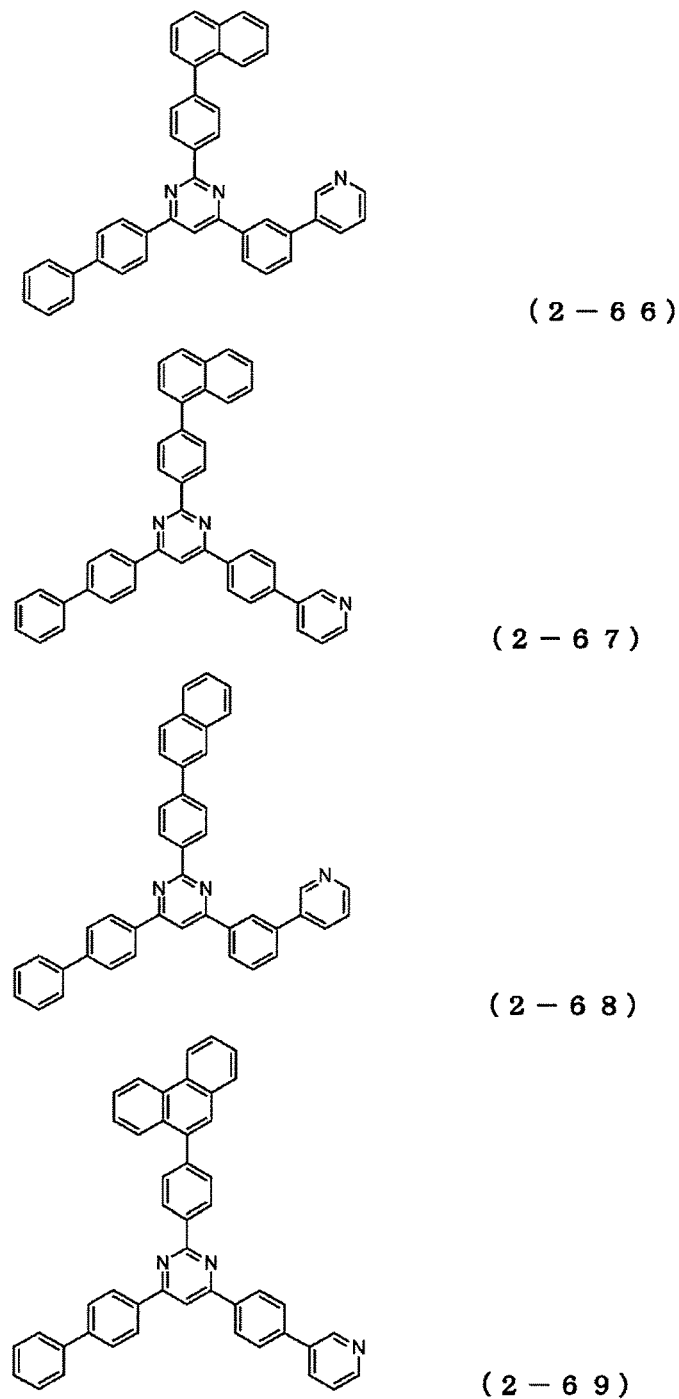
FIG. 29 is a view showing the structural formulas of Compounds (2-66) to (2-69) in the pyrimidine derivative of the general formula (2).
Figure 30:
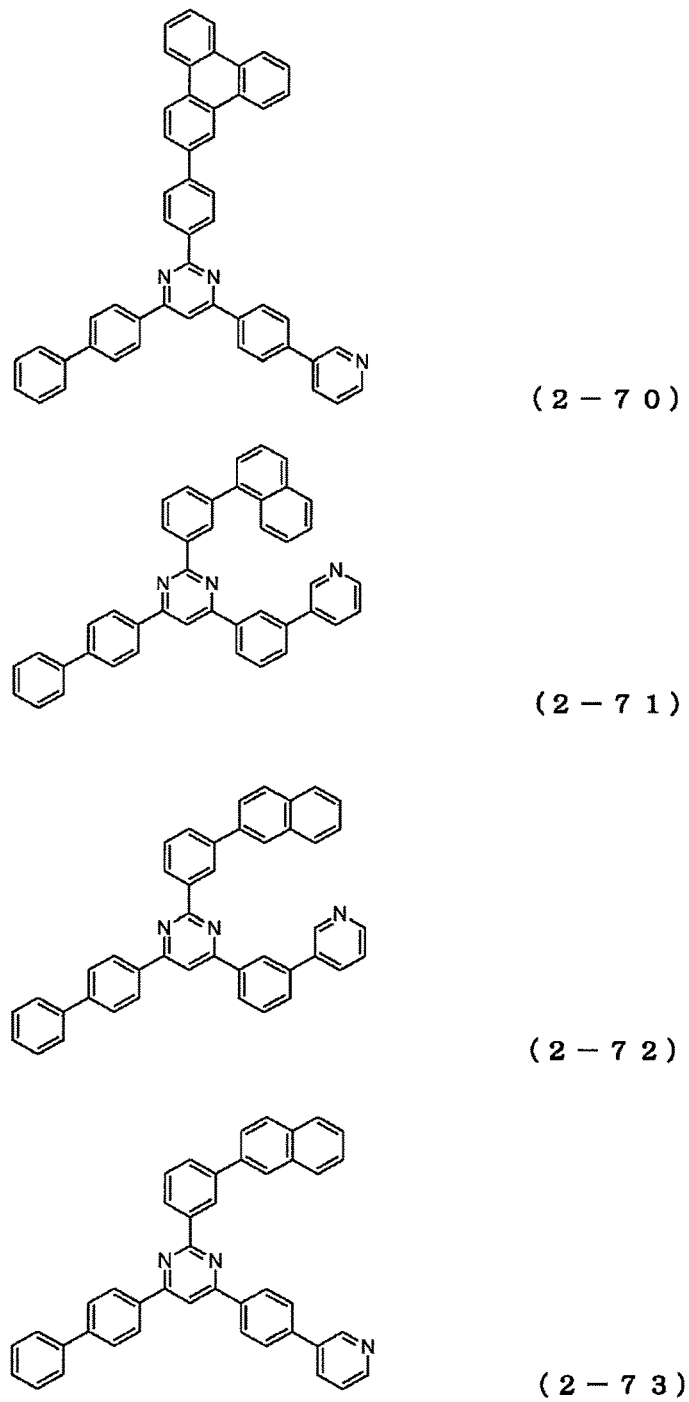
FIG. 30 is a view showing the structural formulas of Compounds (2-70) to (2-73) in the pyrimidine derivative of the general formula (2).
Figure 31:
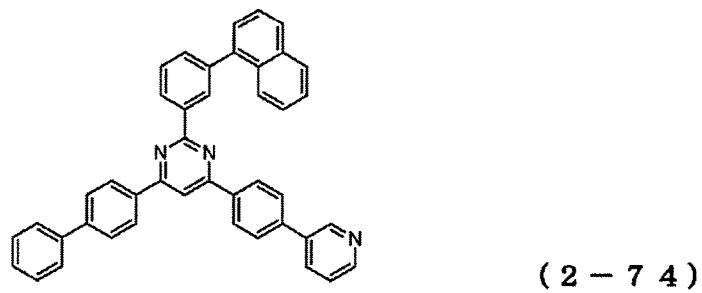
FIG. 31 is a view showing the structural formulas of Compounds (2-74) to (2-76) in the pyrimidine derivative of the general formula (2).
Figure 31:
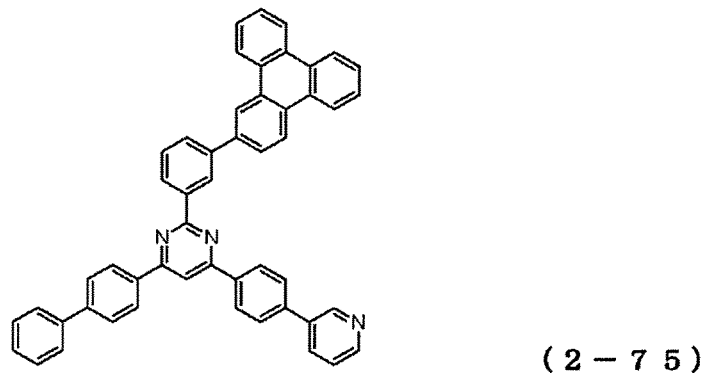
Figure 31:
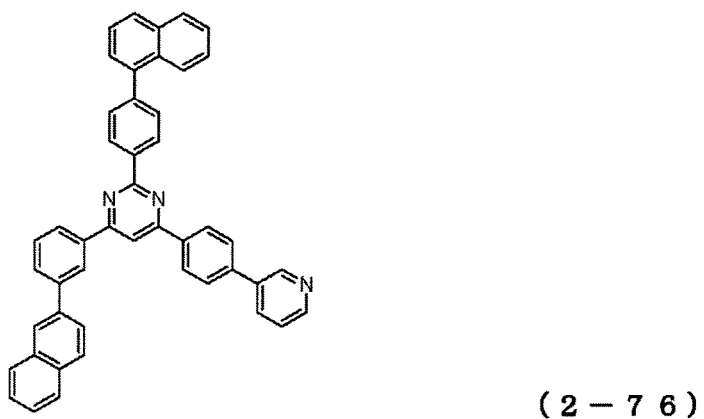
Figure 32:
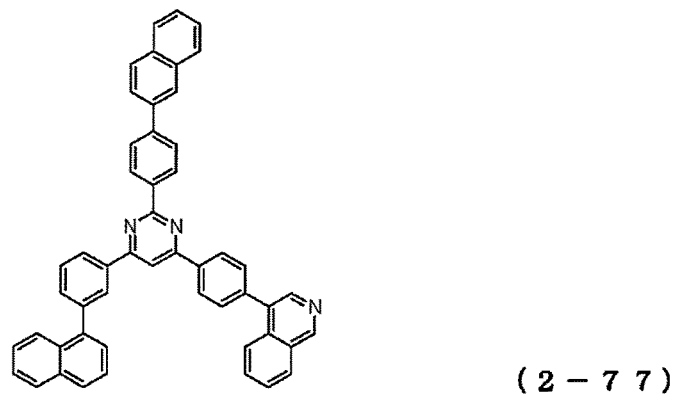
FIG. 32 is a view showing the structural formulas of Compounds (2-77) to (2-79) in the pyrimidine derivative of the general formula (2).
Figure 32:
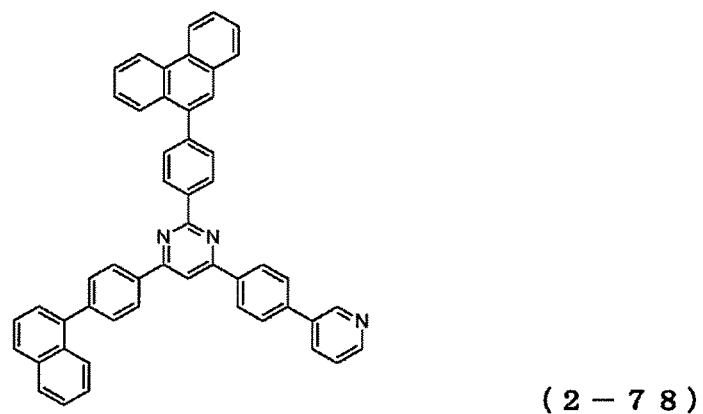
Figure 32:
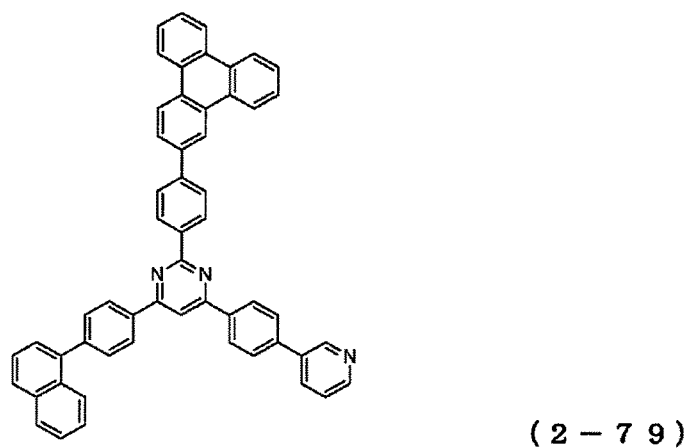
Figure 33:
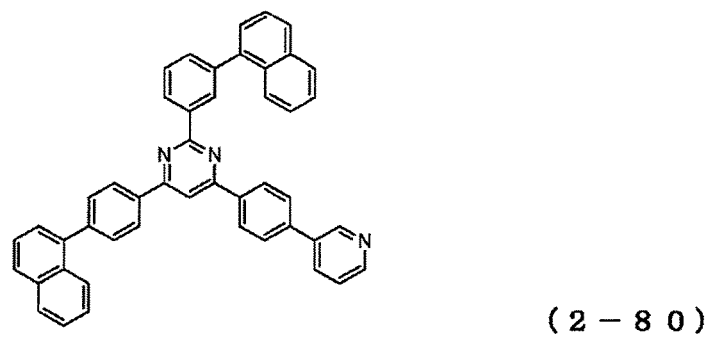
FIG. 33 is a view showing the structural formulas of Compounds (2-80) to (2-82) in the pyrimidine derivative of the general formula (2).
Figure 33:
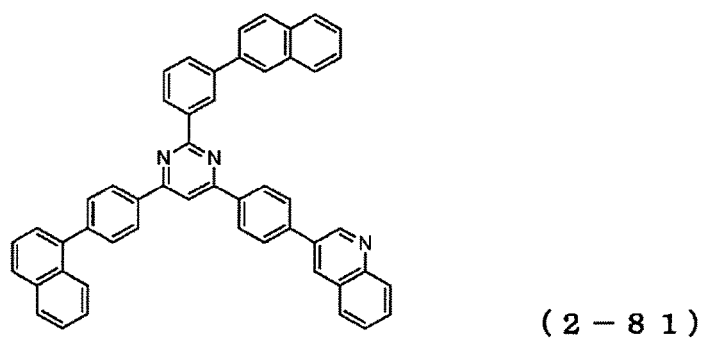
Figure 33:
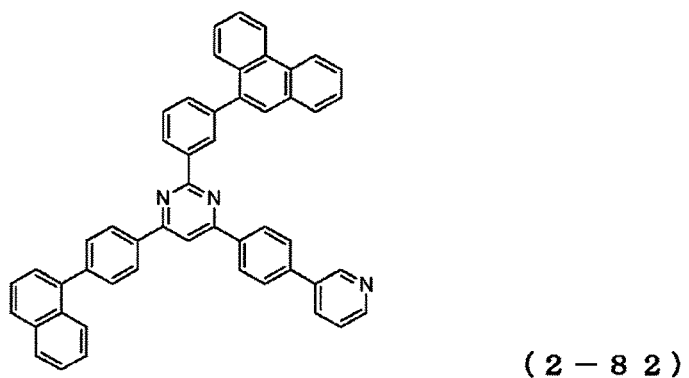
Figure 34:
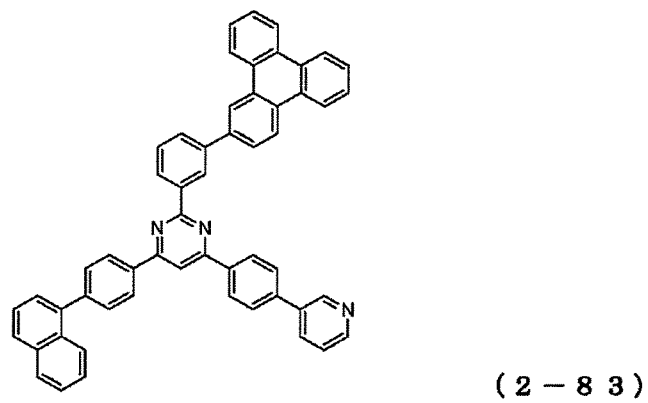
FIG. 34 is a view showing the structural formulas of Compounds (2-83) to (2-85) in the pyrimidine derivative of the general formula (2).
Figure 34:
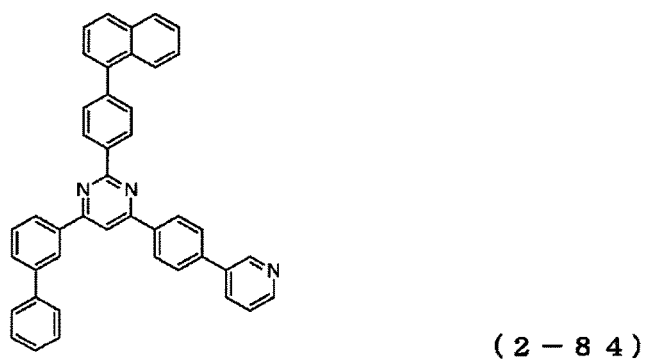
Figure 34:
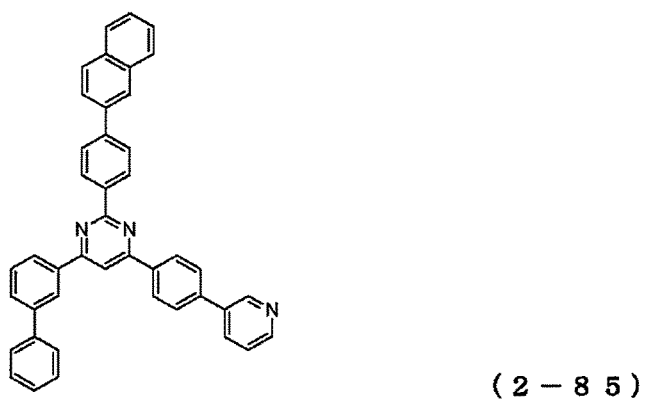
Figure 35:
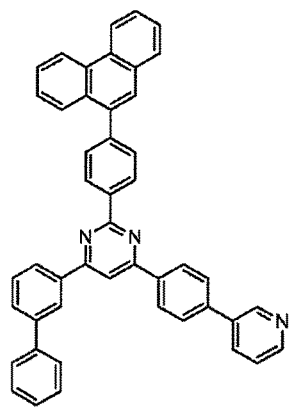
FIG. 35 is a view showing the structural formulas of Compounds (2-86) to (2-88) in the pyrimidine derivative of the general formula (2).
Figure 35:
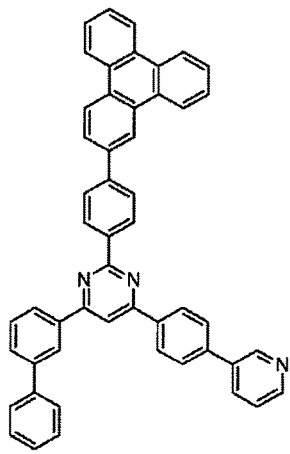
Figure 35:
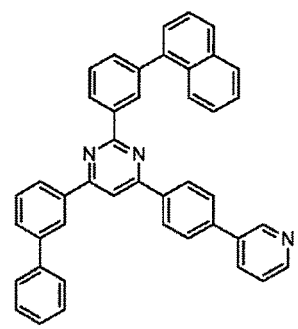
Figure 36:
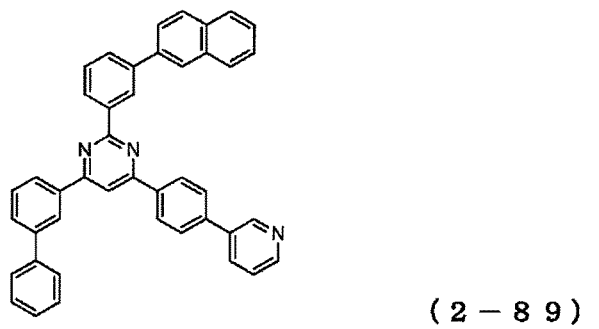
FIG. 36 is a view showing the structural formulas of Compounds (2-89) to (2-91) in the pyrimidine derivative of the general formula (2).
Figure 36:
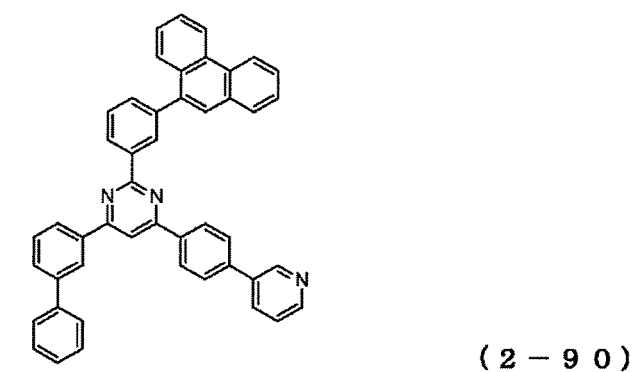
Figure 36:
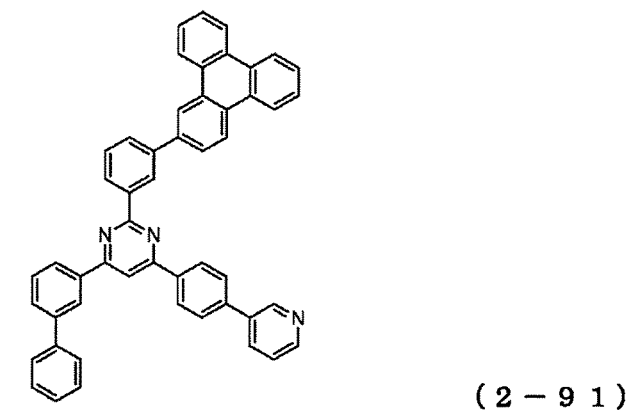
Figure 37:
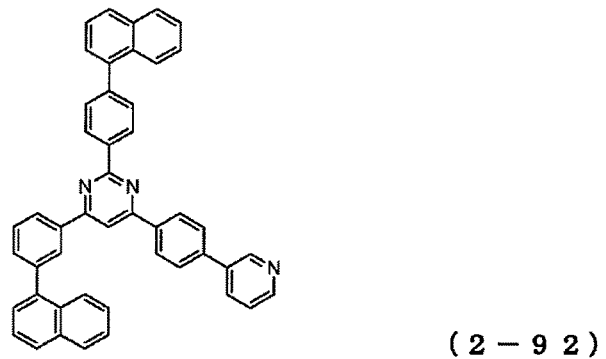
FIG. 37 is a view showing the structural formulas of Compounds (2-92) to (2-94) in the pyrimidine derivative of the general formula (2).
Figure 37:
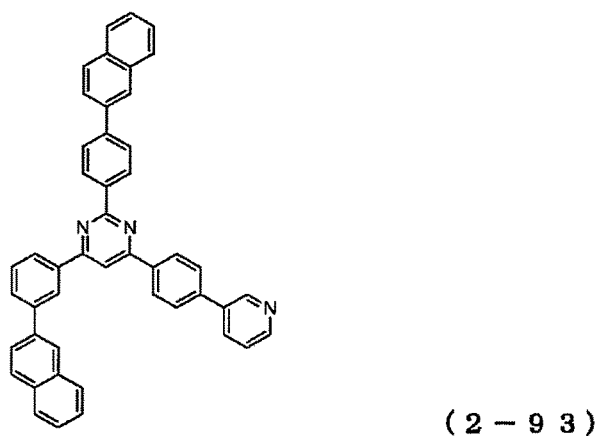
Figure 37:
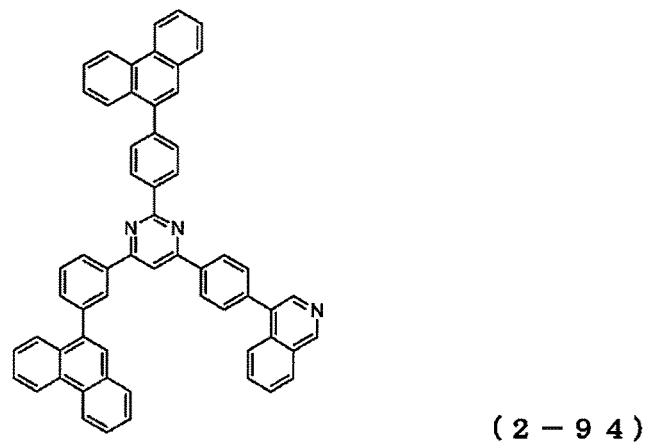
Figure 38:
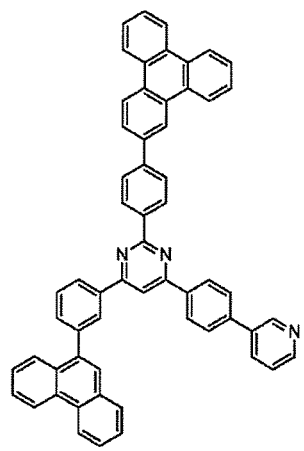
FIG. 38 is a view showing the structural formulas of Compounds (2-95) to (2-97) in the pyrimidine derivative of the general formula (2).
Figure 38:
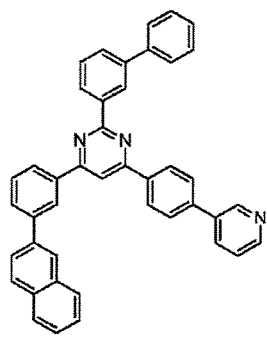
Figure 38:
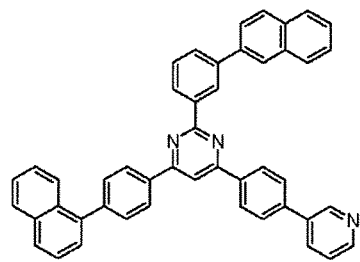
Figure 39:
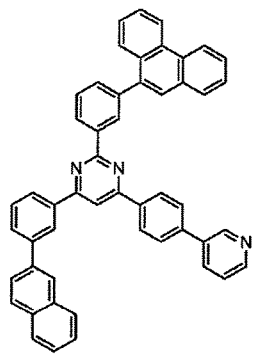
FIG. 39 is a view showing the structural formulas of Compounds (2-98) to (2-100) in the pyrimidine derivative of the general formula (2).
Figure 40:
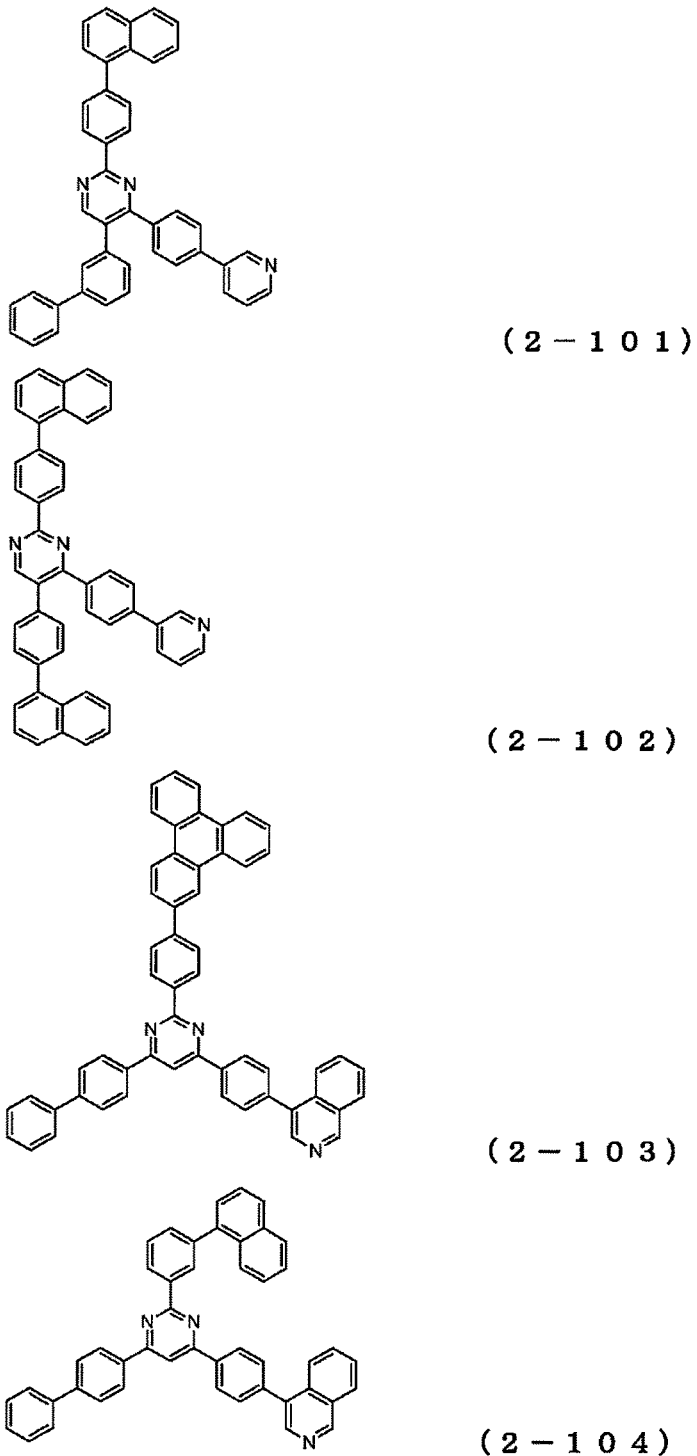
FIG. 40 is a view showing the structural formulas of Compounds (2-101) to (2-104) in the pyrimidine derivative of the general formula (2).
Figure 41:
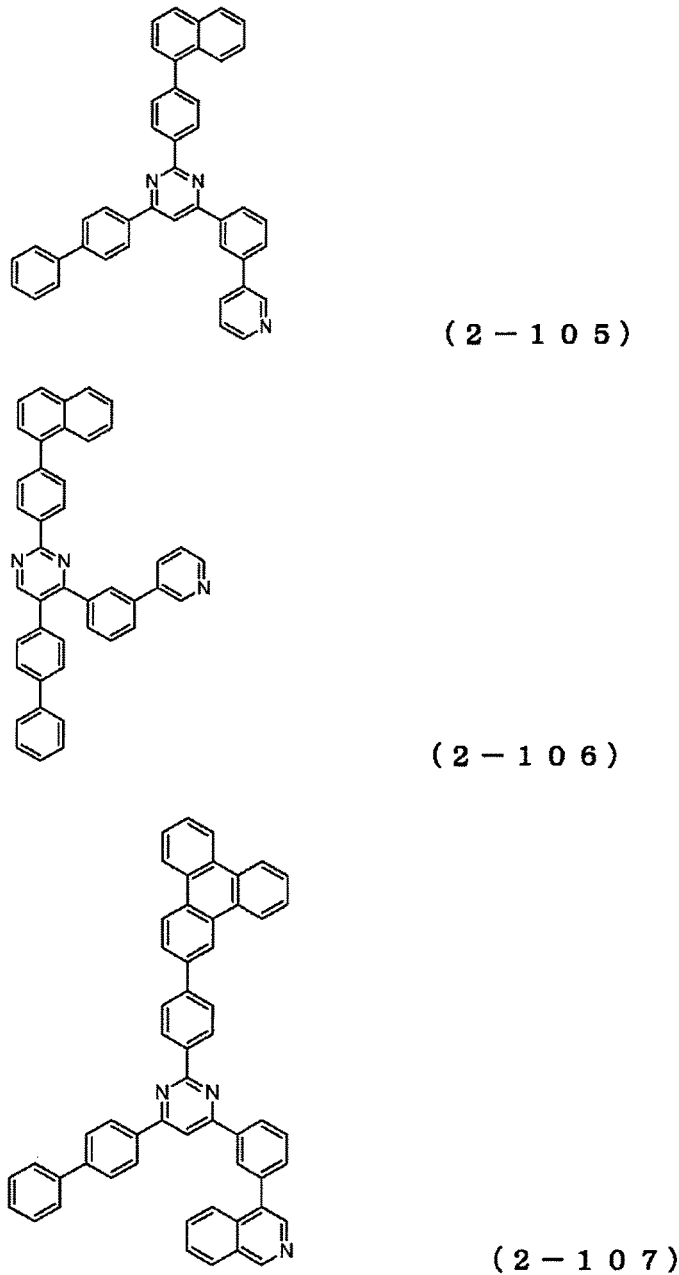
FIG. 41 is a view showing the structural formulas of Compounds (2-105) to (2-107) in the pyrimidine derivative of the general formula (2).
Figure 42:
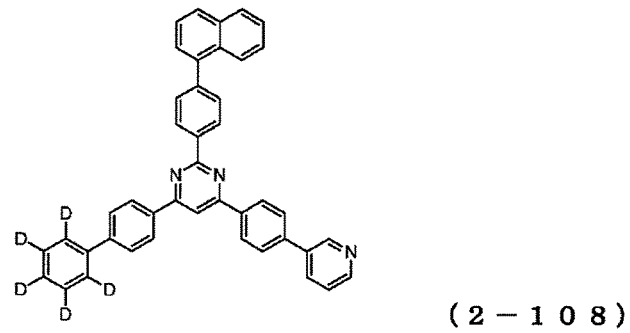
FIG. 42 is a view showing the structural formulas of Compounds (2-108) to (2-110) in the pyrimidine derivative of the general formula (2).
Figure 42:
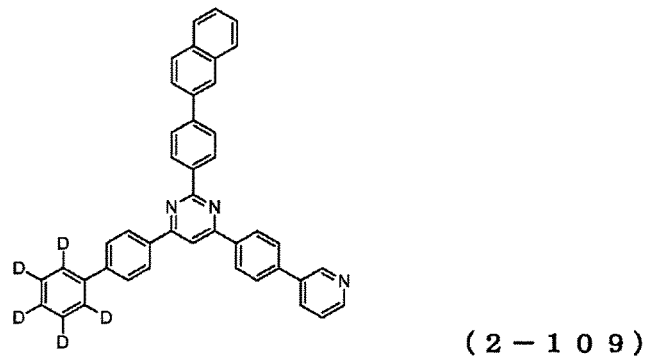
Figure 42:
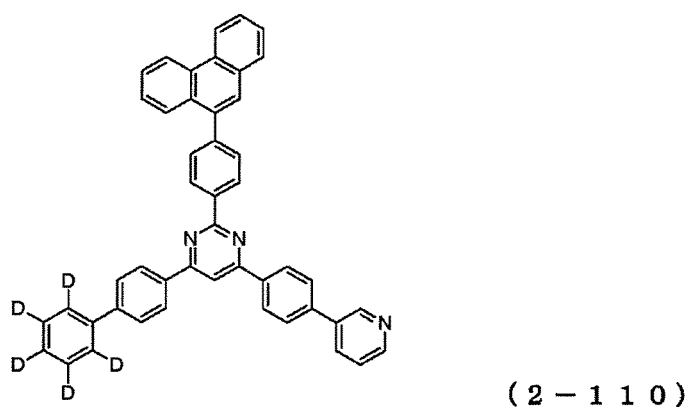
Figure 43:
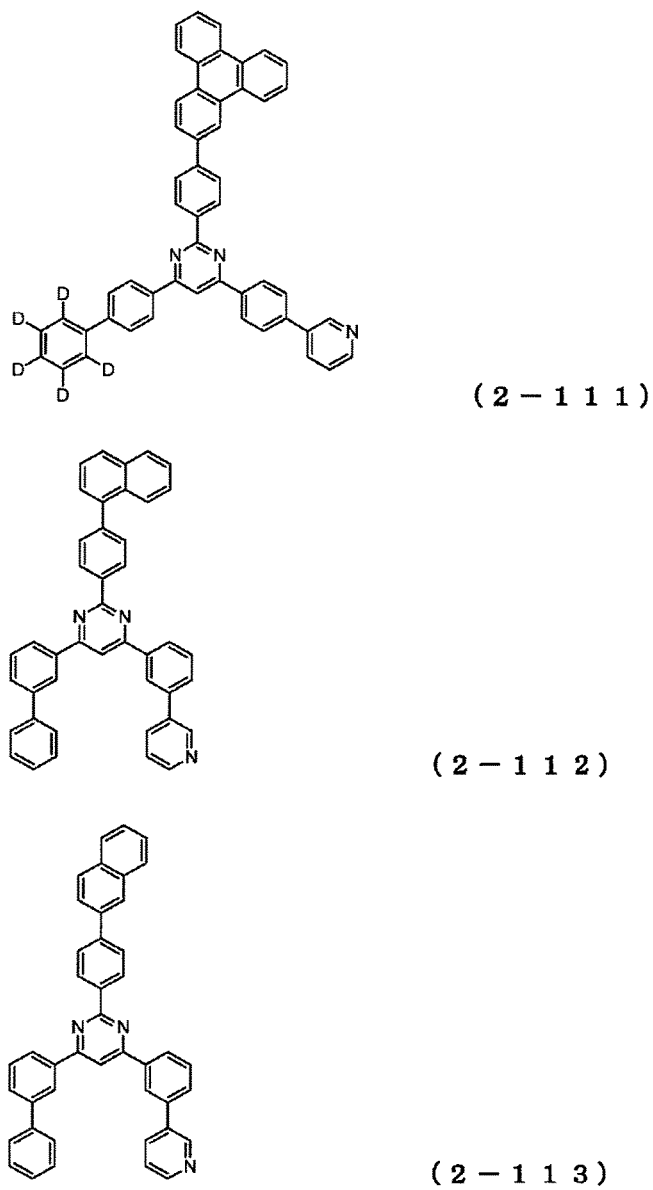
FIG. 43 is a view showing the structural formulas of Compounds (2-111) to (2-113) in the pyrimidine derivative of the general formula (2).
Figure 44:
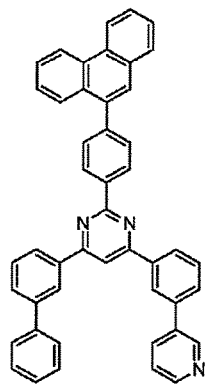
FIG. 44 is a view showing the structural formulas of Compounds (2-114) to (2-116) in the pyrimidine derivative of the general formula (2).
Figure 44:
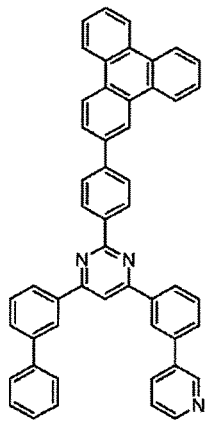
Figure 44:
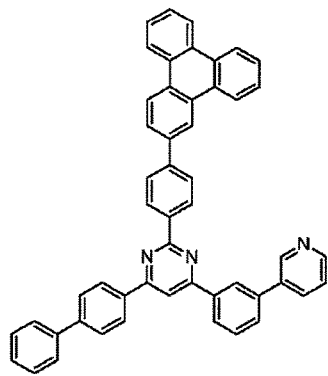
Figure 45:
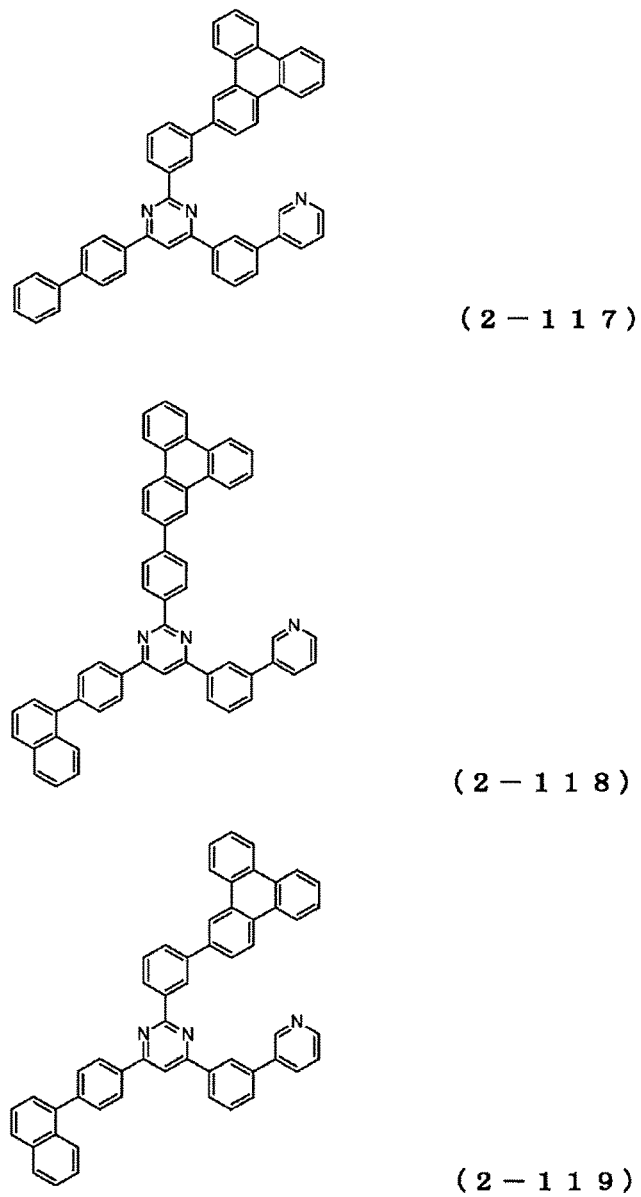
FIG. 45 is a view showing the structural formulas of Compounds (2-117) to (2-119) in the pyrimidine derivative of the general formula (2).
Figure 46:
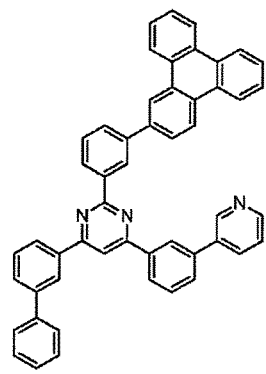
FIG. 46 is a view showing the structural formulas of Compounds (2-120) to (2-122) in the pyrimidine derivative of the general formula (2).
Figure 46:
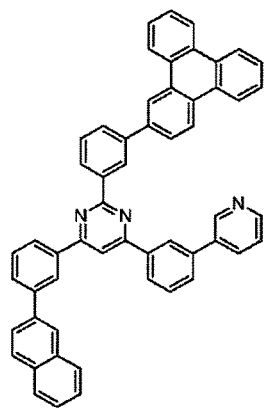
Figure 46:
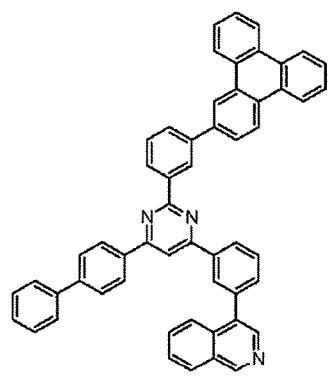
Figure 47:
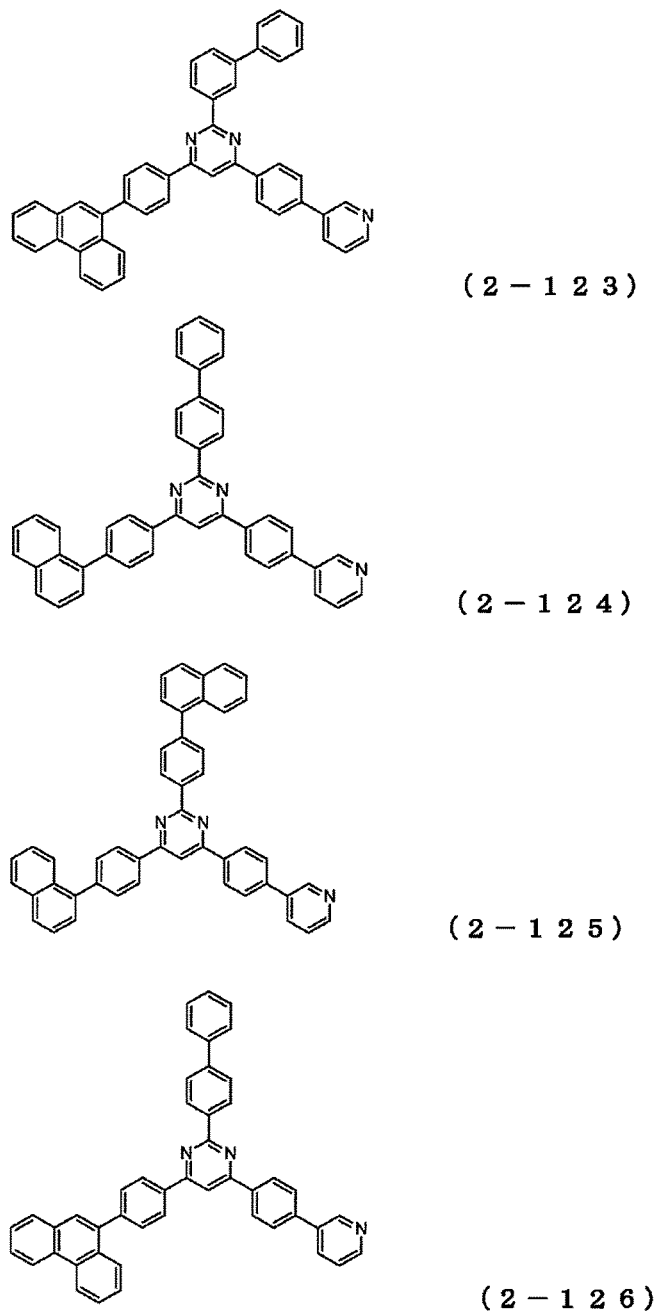
FIG. 47 is a view showing the structural formulas of Compounds (2-123) to (2-126) in the pyrimidine derivative of the general formula (2).
Figure 48:
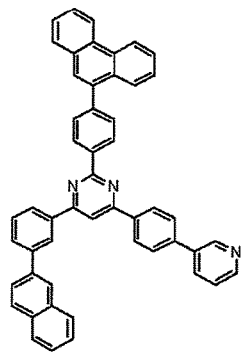
FIG. 48 is a view showing the structural formulas of Compounds (2-127) to (2-129) in the pyrimidine derivative of the general formula (2).
Figure 48:
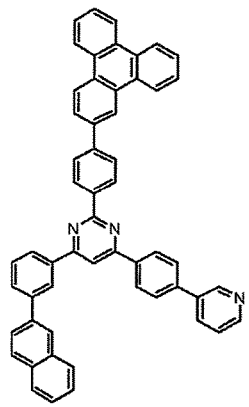
Figure 48:
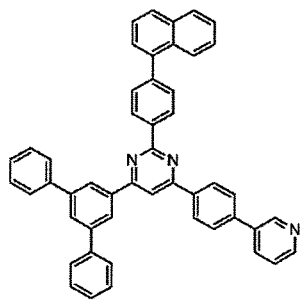
Figure 49:
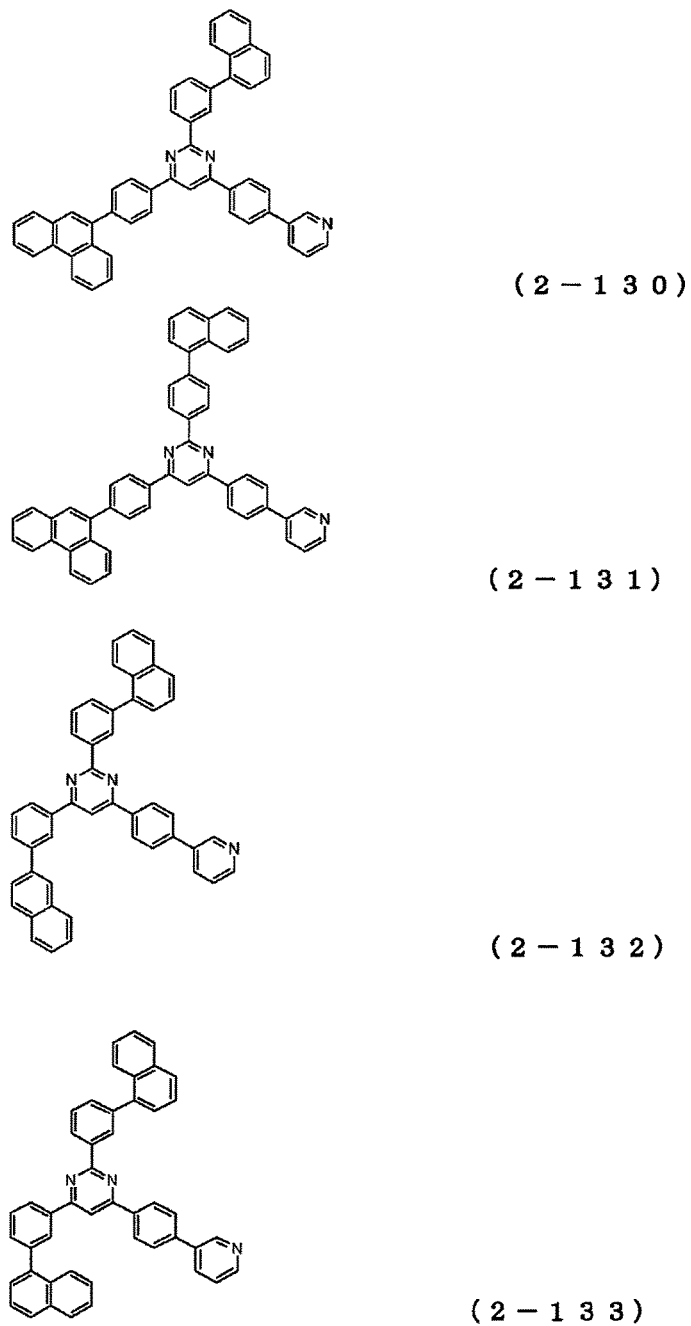
FIG. 49 is a view showing the structural formulas of Compounds (2-130) to (2-133) in the pyrimidine derivative of the general formula (2).
Figure 50:
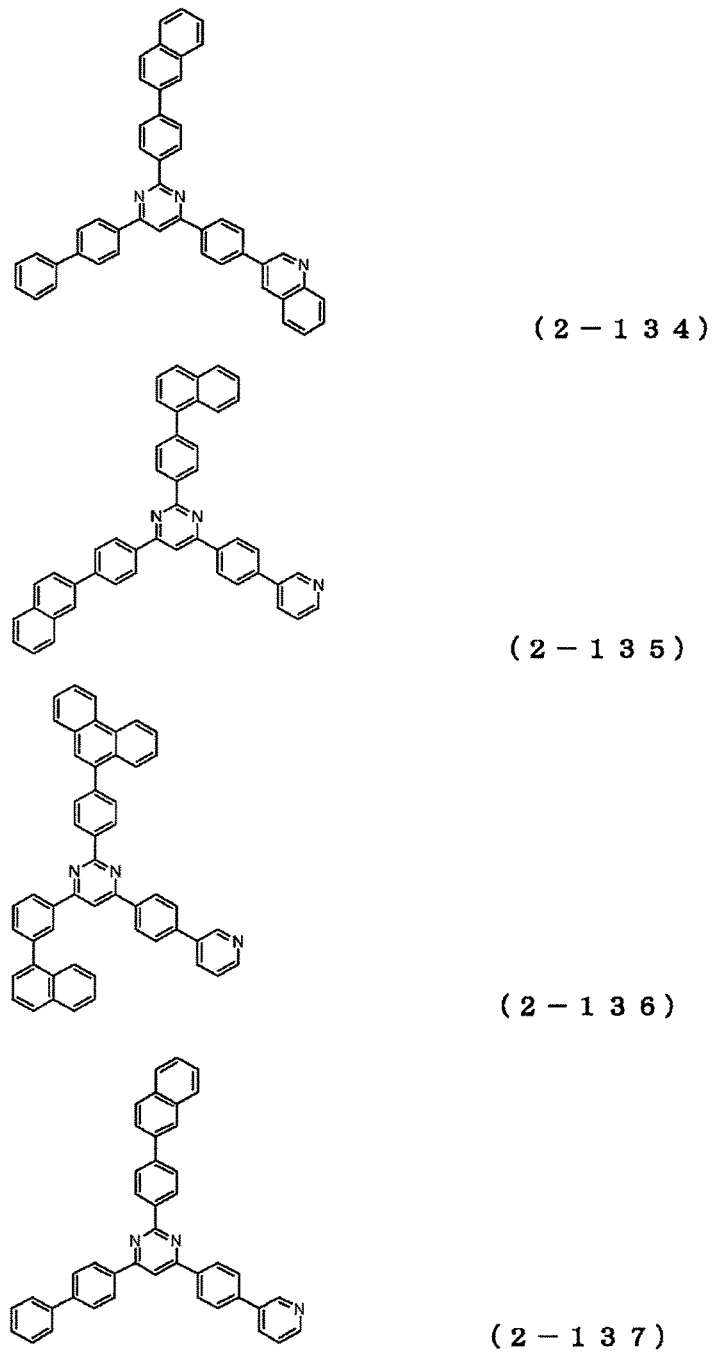
FIG. 50 is a view showing the structural formulas of Compounds (2-134) to (2-137) in the pyrimidine derivative of the general formula (2).
Figure 51:
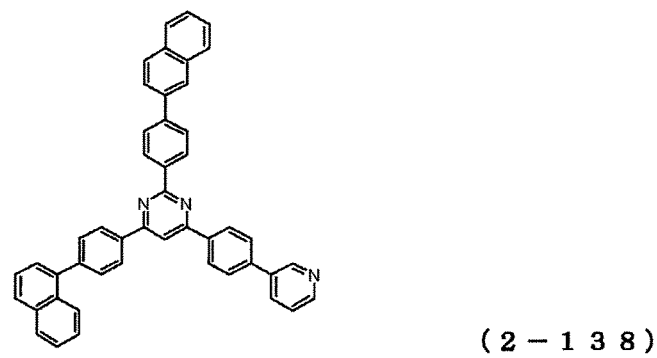
FIG. 51 is a view showing the structural formulas of Compounds (2-138) to (2-140) in the pyrimidine derivative of the general formula (2).
Figure 51:
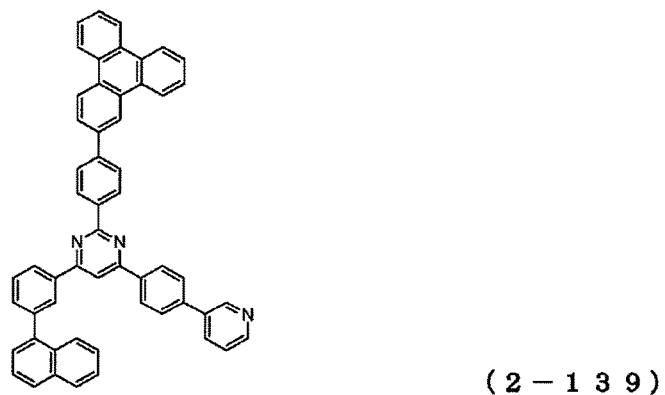
Figure 51:
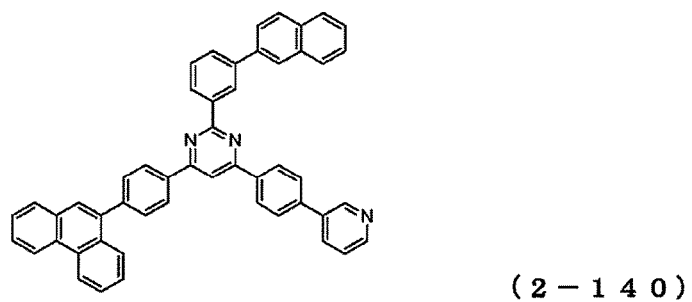
Figure 52:
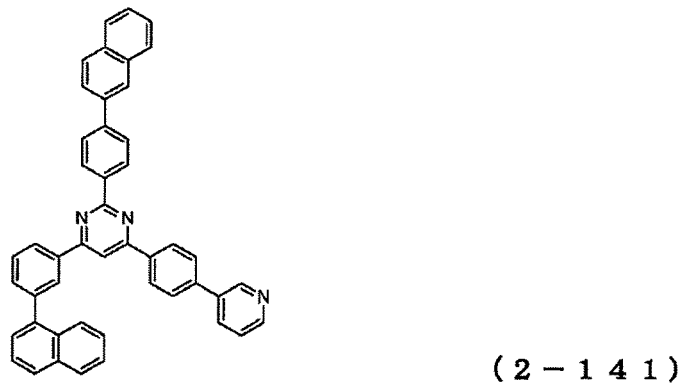
FIG. 52 is a view showing the structural formulas of Compounds (2-141) to (2-143) in the pyrimidine derivative of the general formula (2).
Figure 52:
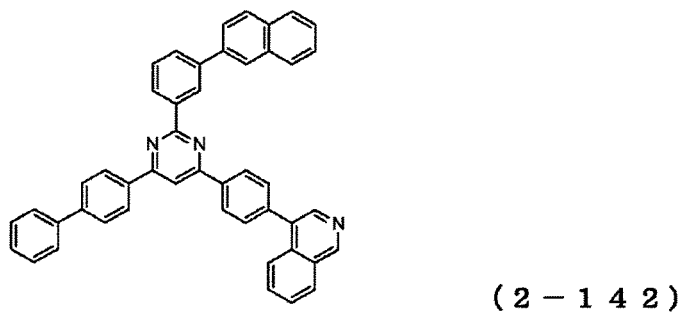
Figure 52:
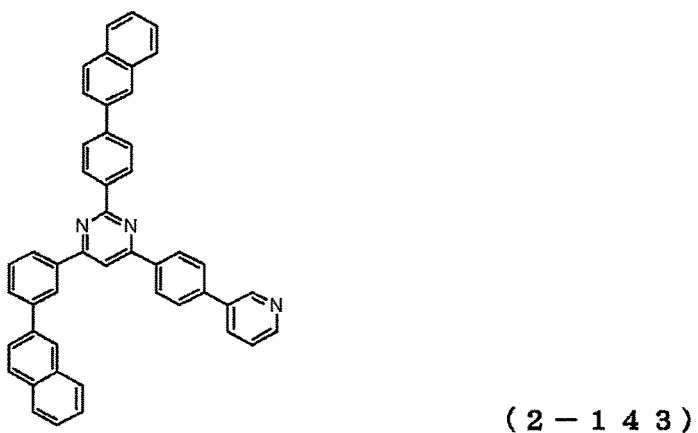
Figure 53:
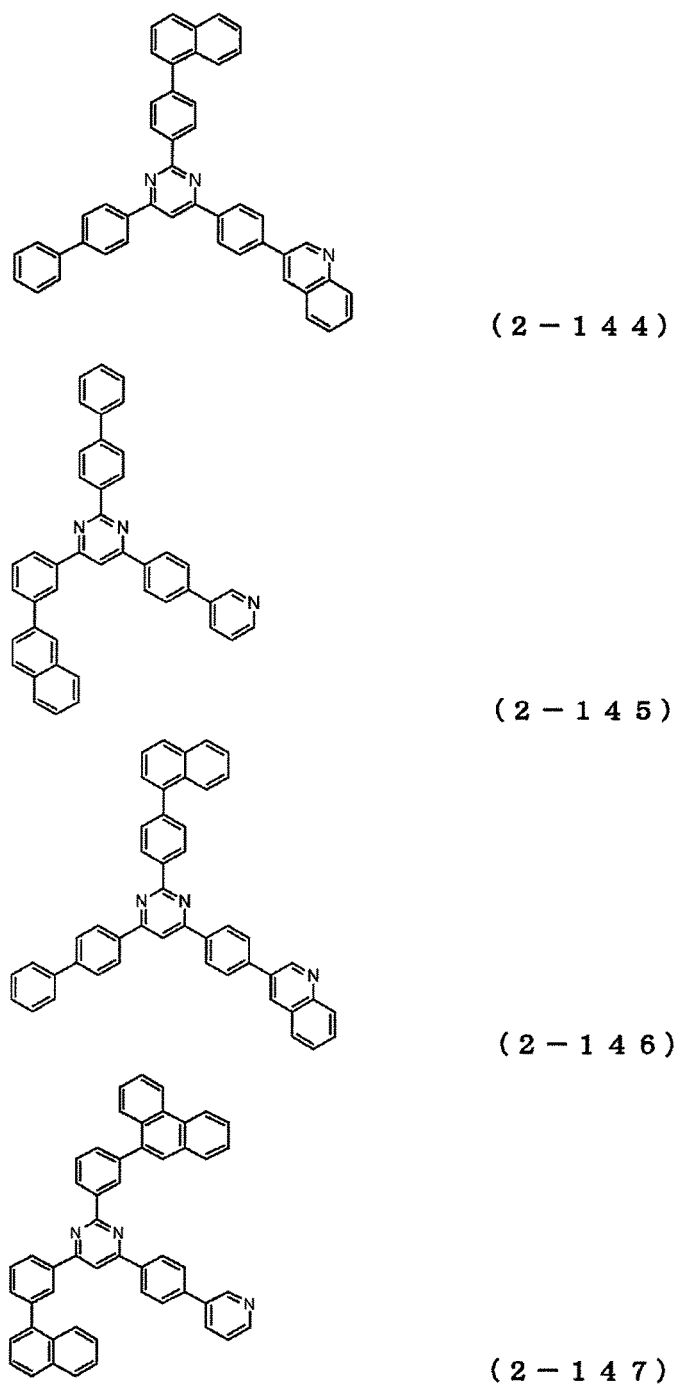
FIG. 53 is a view showing the structural formulas of Compounds (2-144) to (2-147) in the pyrimidine derivative of the general formula (2).
Figure 54:
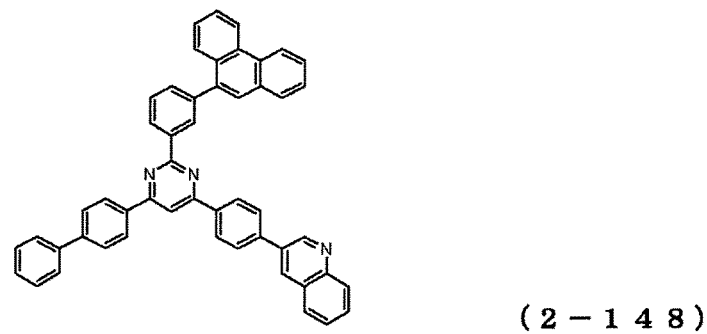
FIG. 54 is a view showing the structural formulas of Compounds (2-148) to (2-150) in the pyrimidine derivative of the general formula (2).
Figure 54:
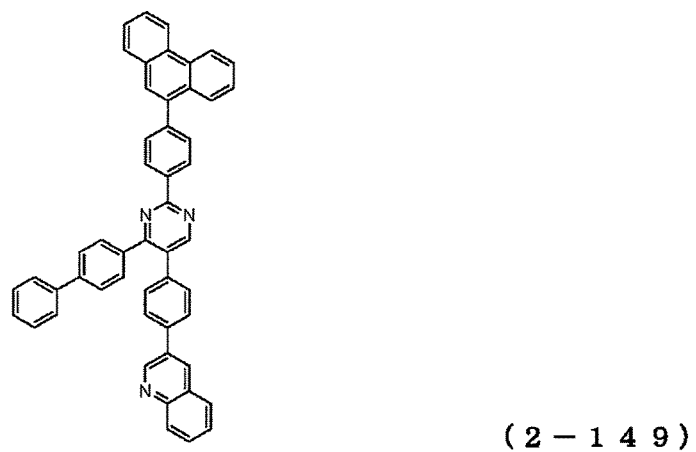
Figure 54:
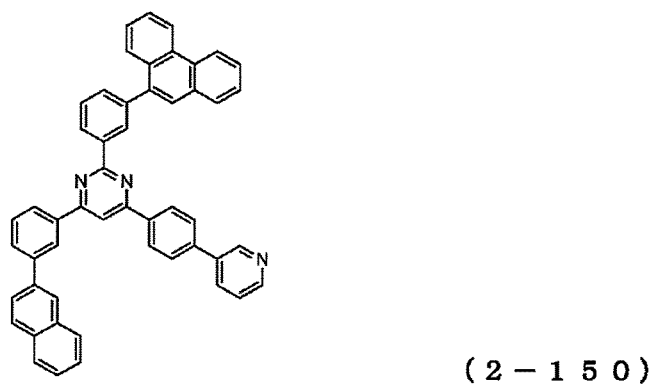
Figure 55:
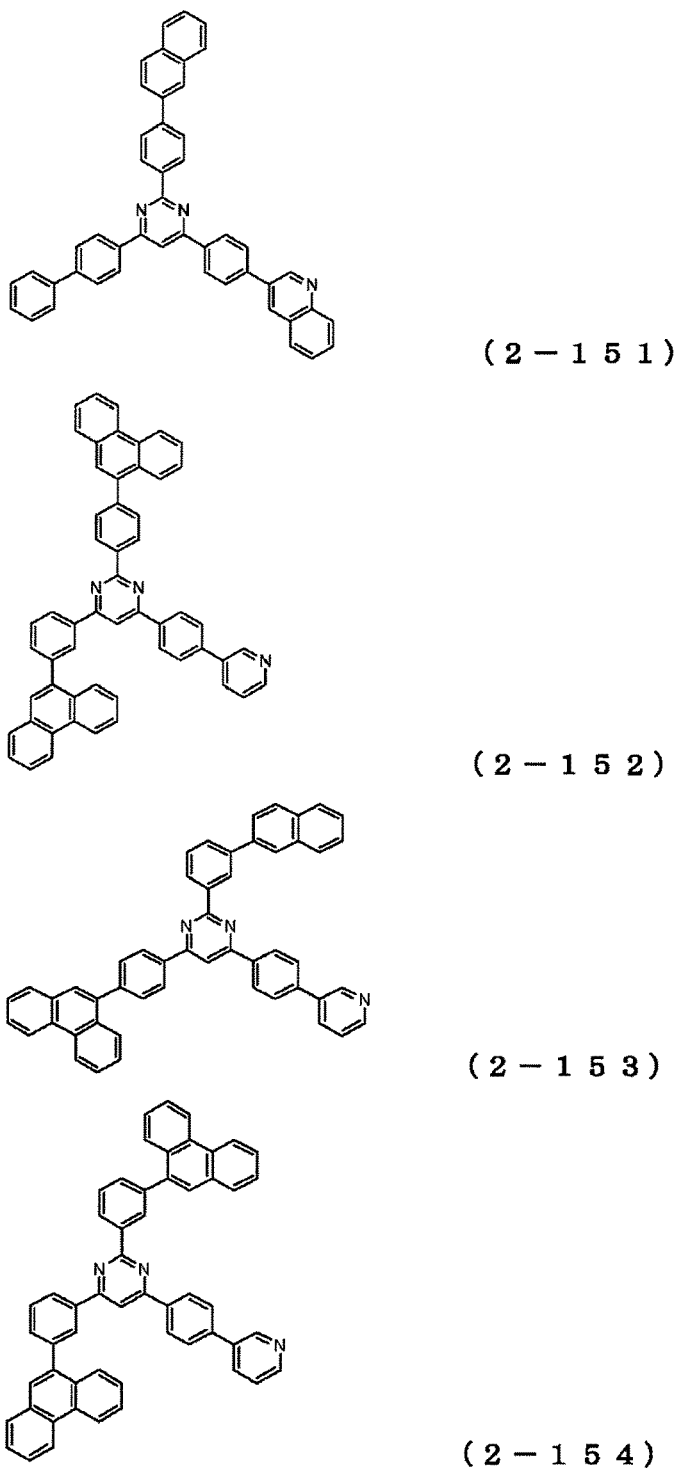
FIG. 55 is a view showing the structural formulas of Compounds (2-151) to (2-154) in the pyrimidine derivative of the general formula (2).
Figure 56:
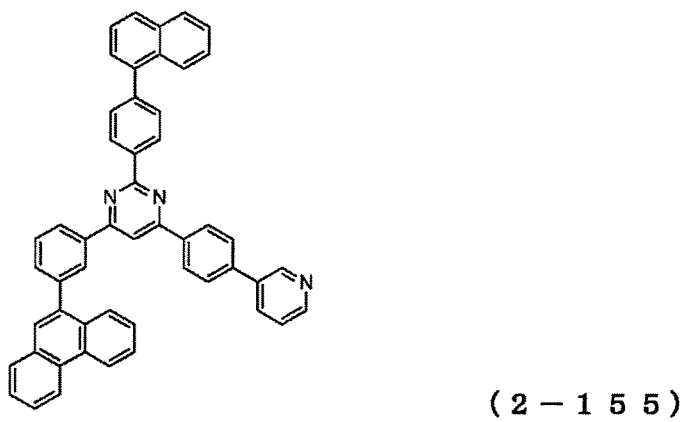
FIG. 56 is a view showing the structural formulas of Compounds (2-155) to (2-157) in the pyrimidine derivative of the general formula (2).
Figure 56:
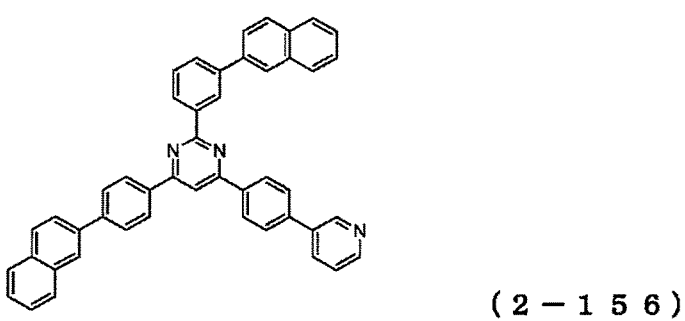
Figure 56:
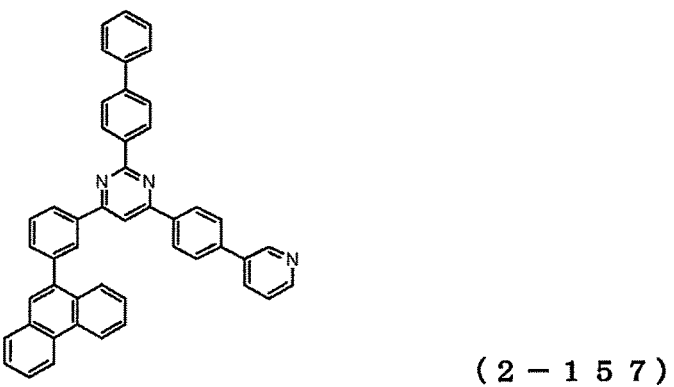
Figure 57:
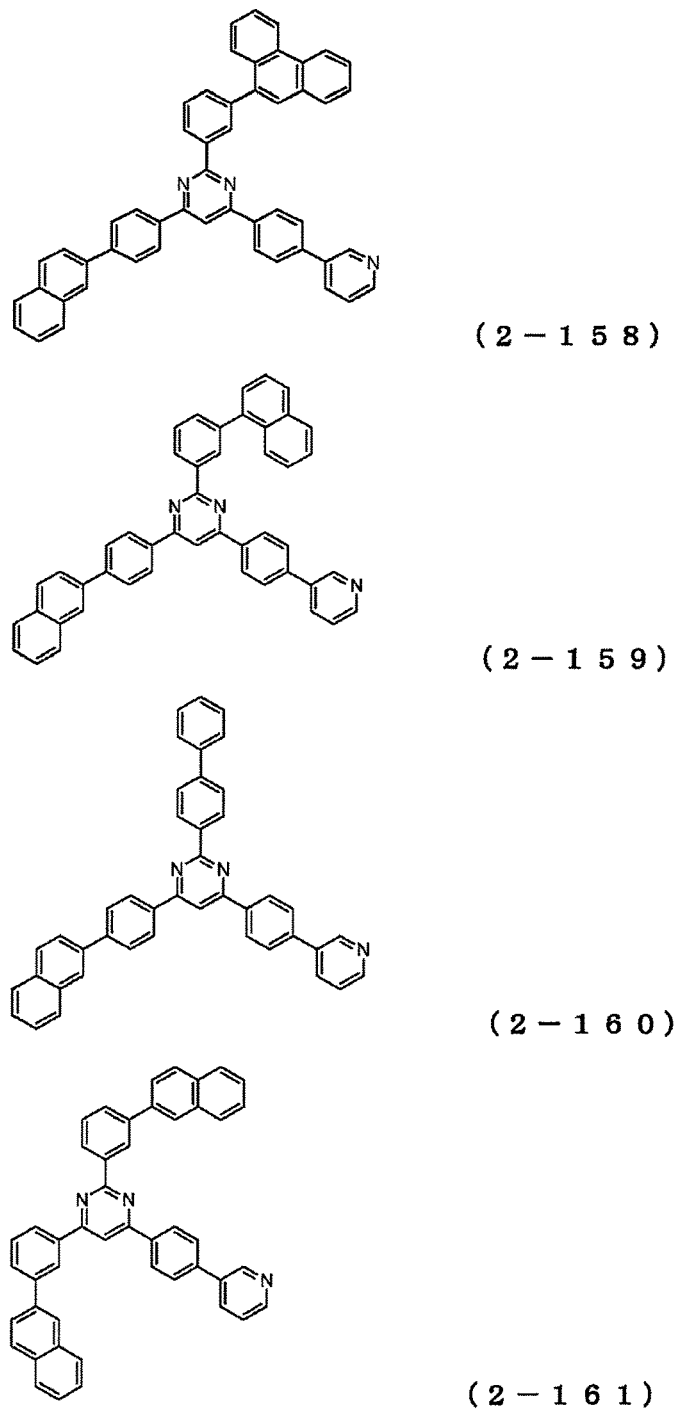
FIG. 57 is a view showing the structural formulas of Compounds (2-158) to (2-161) in the pyrimidine derivative of the general formula (2).
Figure 58:
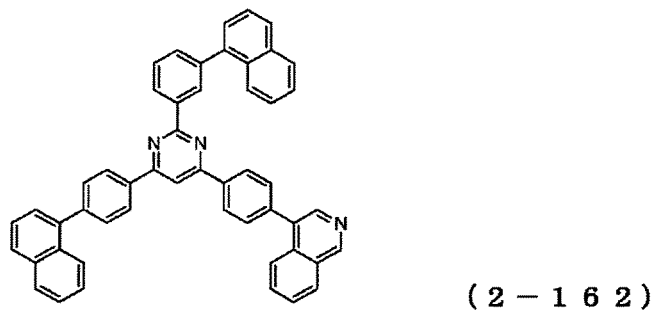
FIG. 58 is a view showing the structural formulas of Compounds (2-162) to (2-165) in the pyrimidine derivative of the general formula (2).
Figure 58:
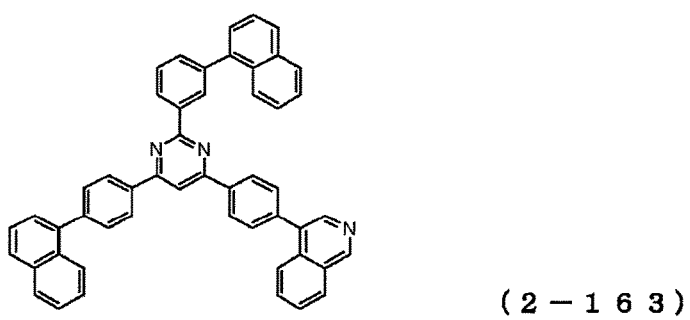
Figure 58:
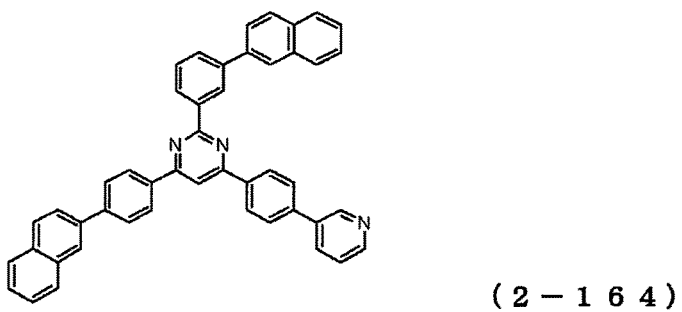
Figure 58:
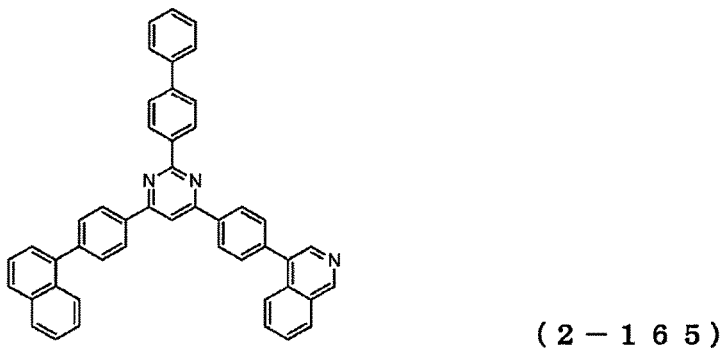
Figure 59:
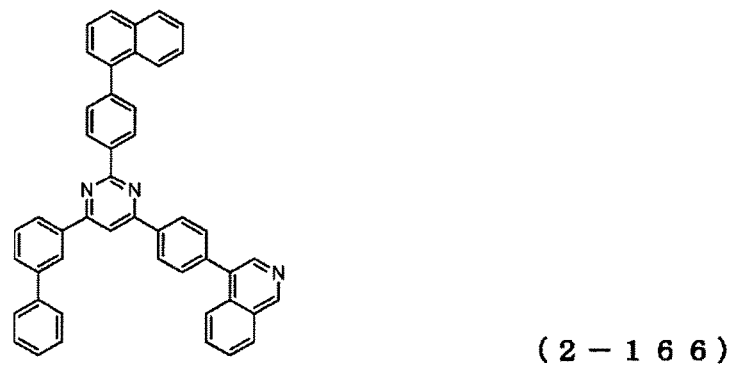
FIG. 59 is a view showing the structural formulas of Compounds (2-166) to (2-168) in the pyrimidine derivative of the general formula (2).
Figure 59:
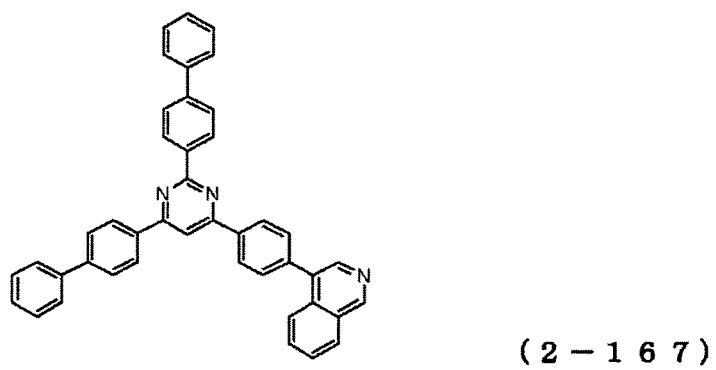
Figure 59:
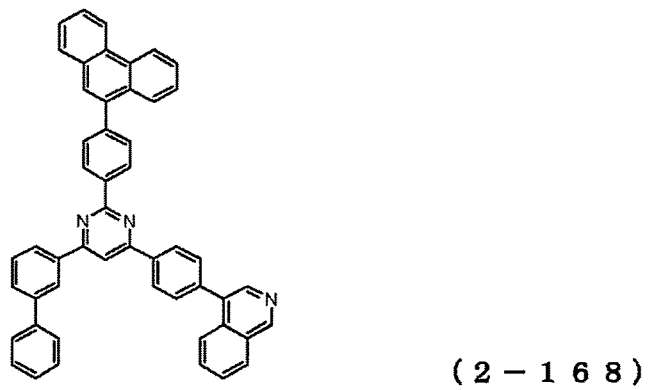
Figure 60:
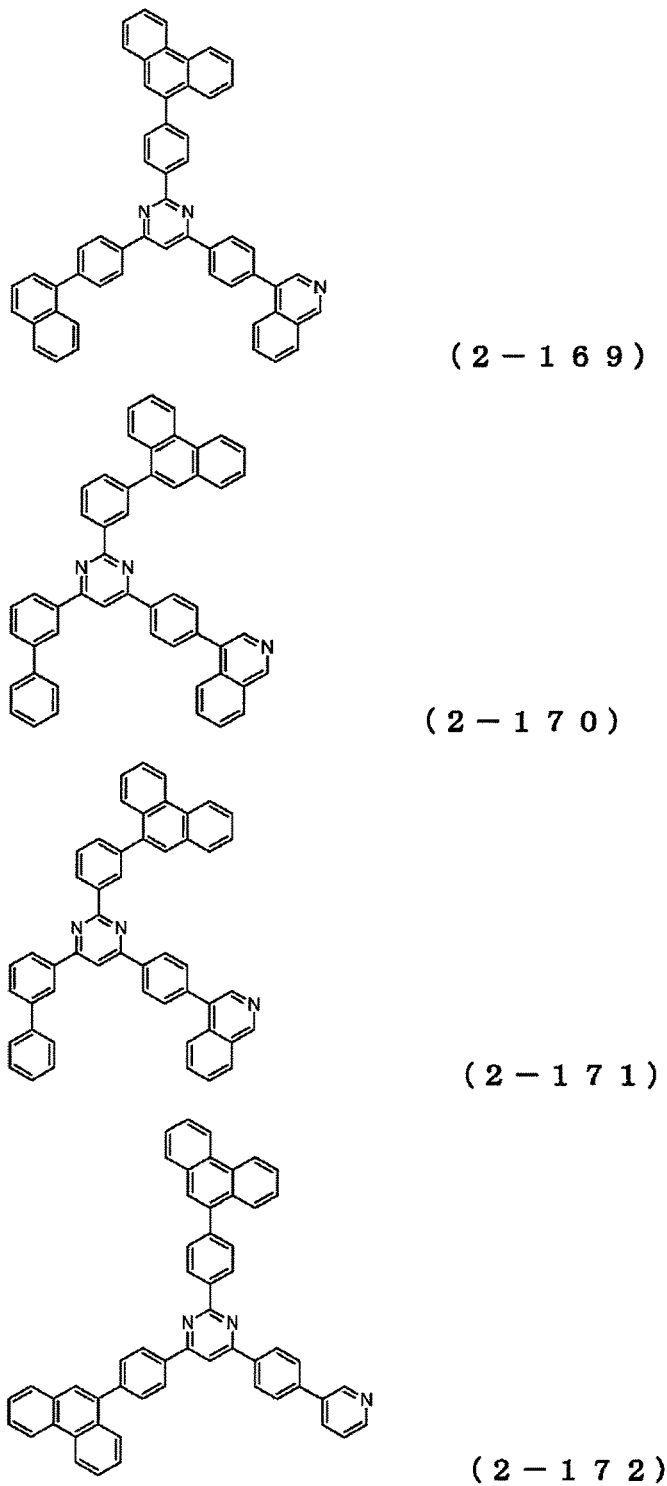
FIG. 60 is a view showing the structural formulas of Compounds (2-169) to (2-172) in the pyrimidine derivative of the general formula (2).
Figure 61:
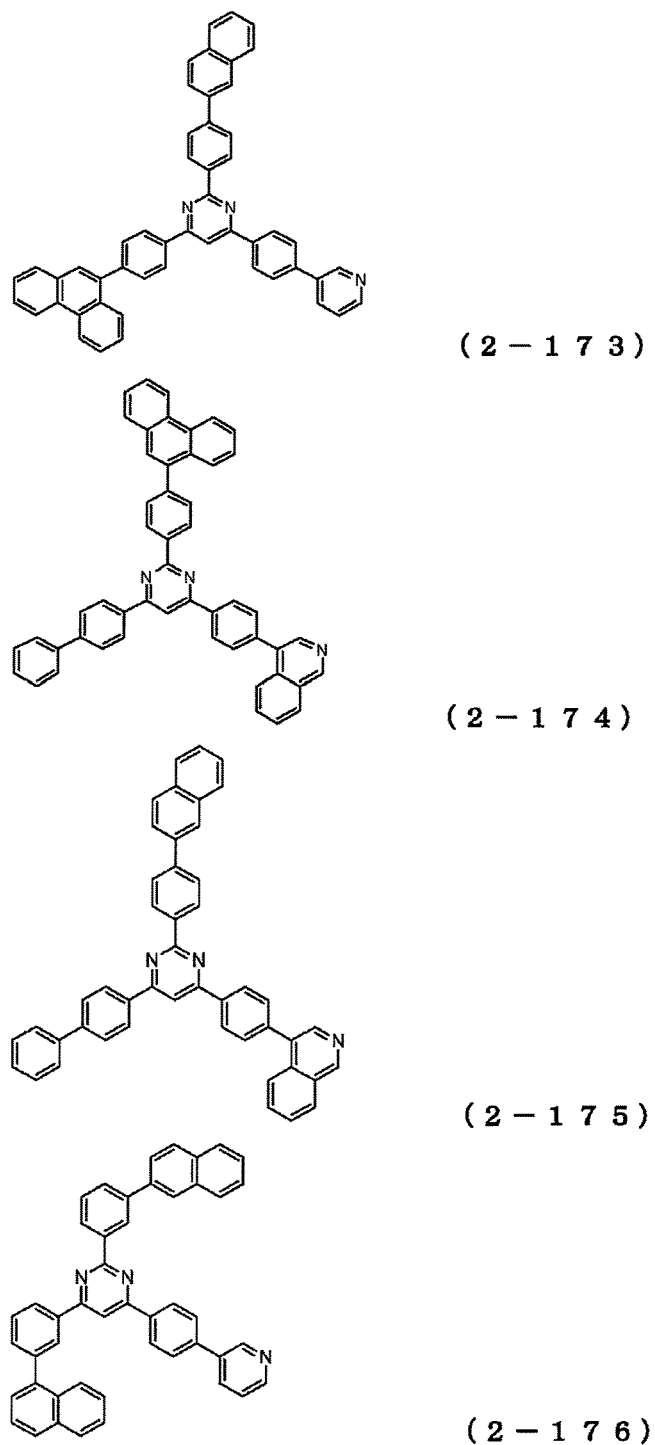
FIG. 61 is a view showing the structural formulas of Compounds (2-173) to (2-176) in the pyrimidine derivative of the general formula (2).
Figure 62:
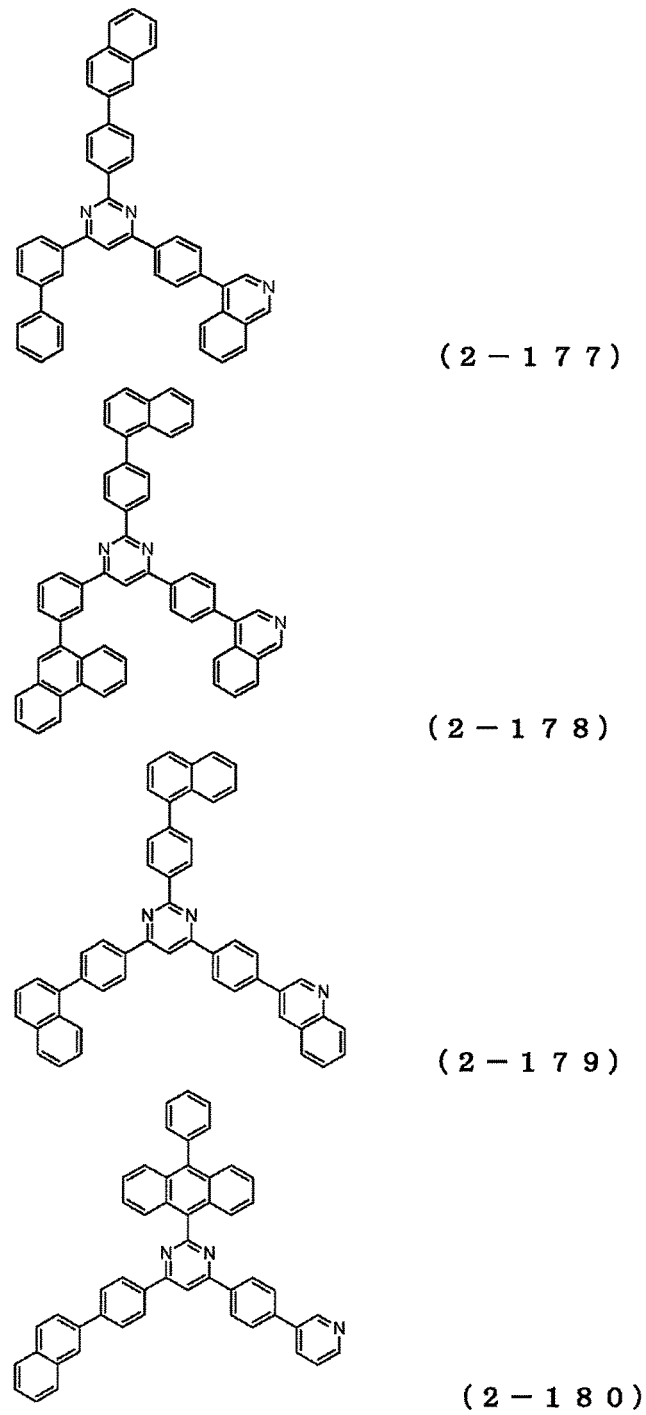
FIG. 62 is a view showing the structural formulas of Compounds (2-177) to (2-180) in the pyrimidine derivative of the general formula (2).
Figure 63:
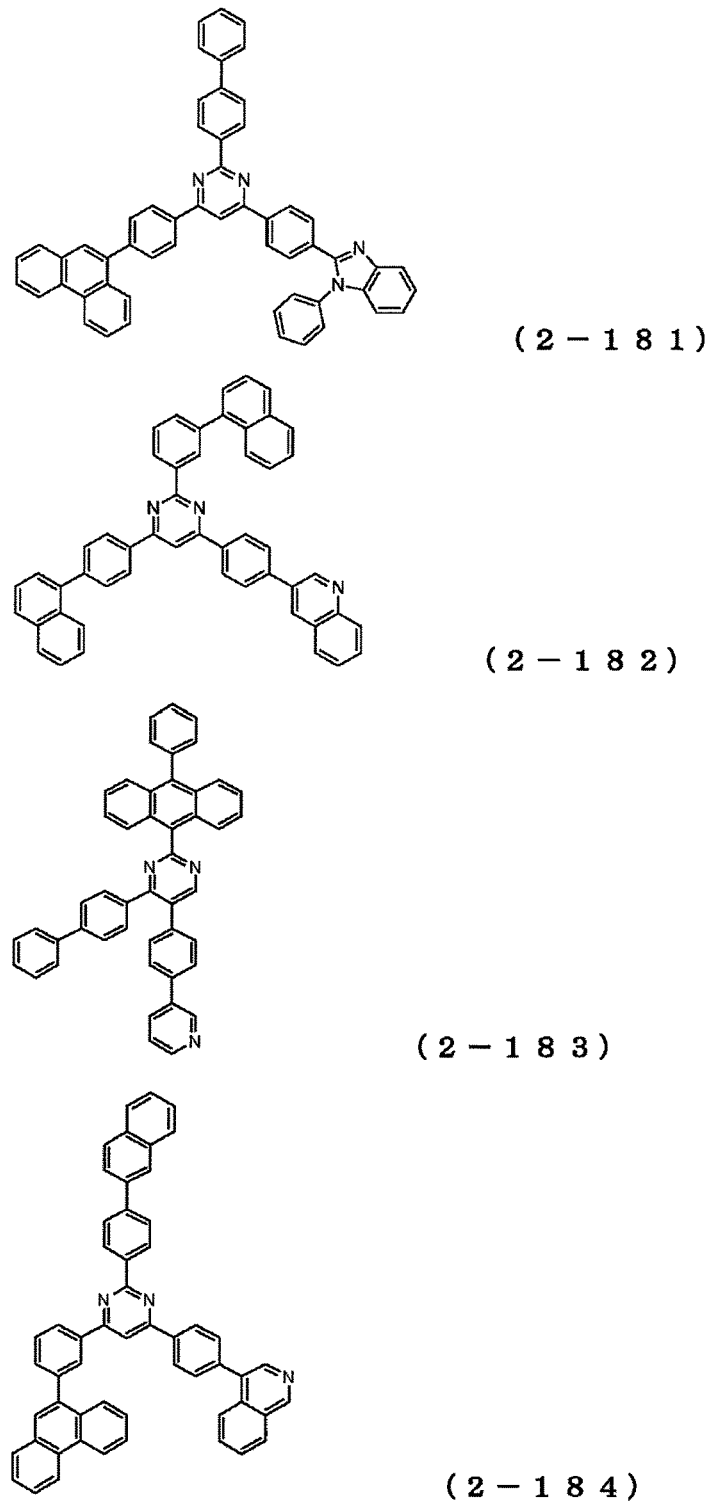
FIG. 63 is a view showing the structural formulas of Compounds (2-181) to (2-184) in the pyrimidine derivative of the general formula (2).
Figure 64:
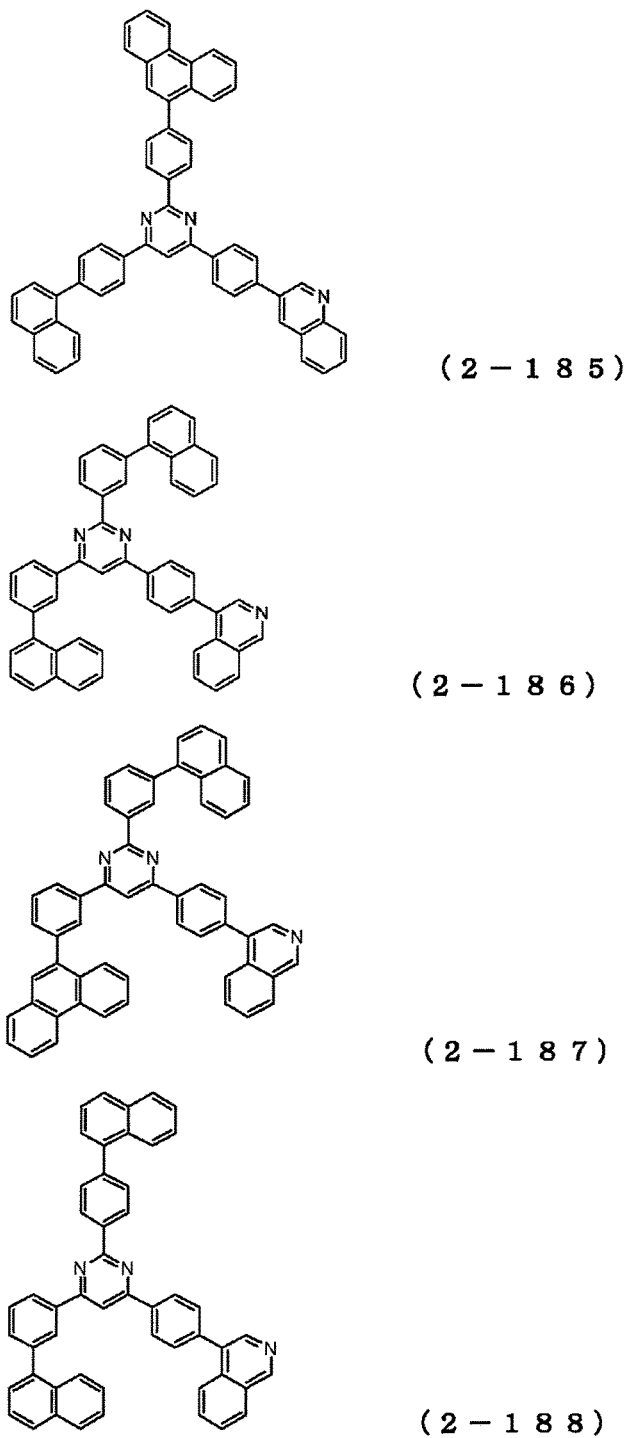
FIG. 64 is a view showing the structural formulas of Compounds (2-185) to (2-188) in the pyrimidine derivative of the general formula (2).
Figure 65:
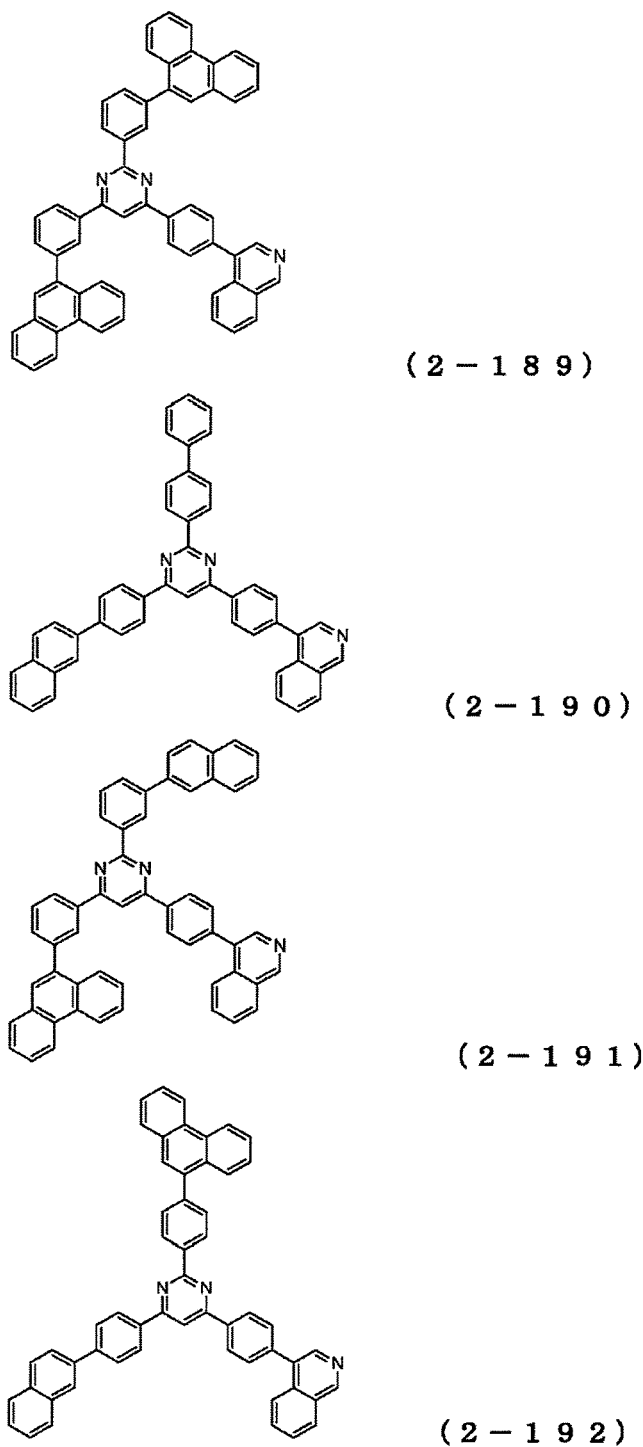
FIG. 65 is a view showing the structural formulas of Compounds (2-189) to (2-192) in the pyrimidine derivative of the general formula (2).
Figure 66:
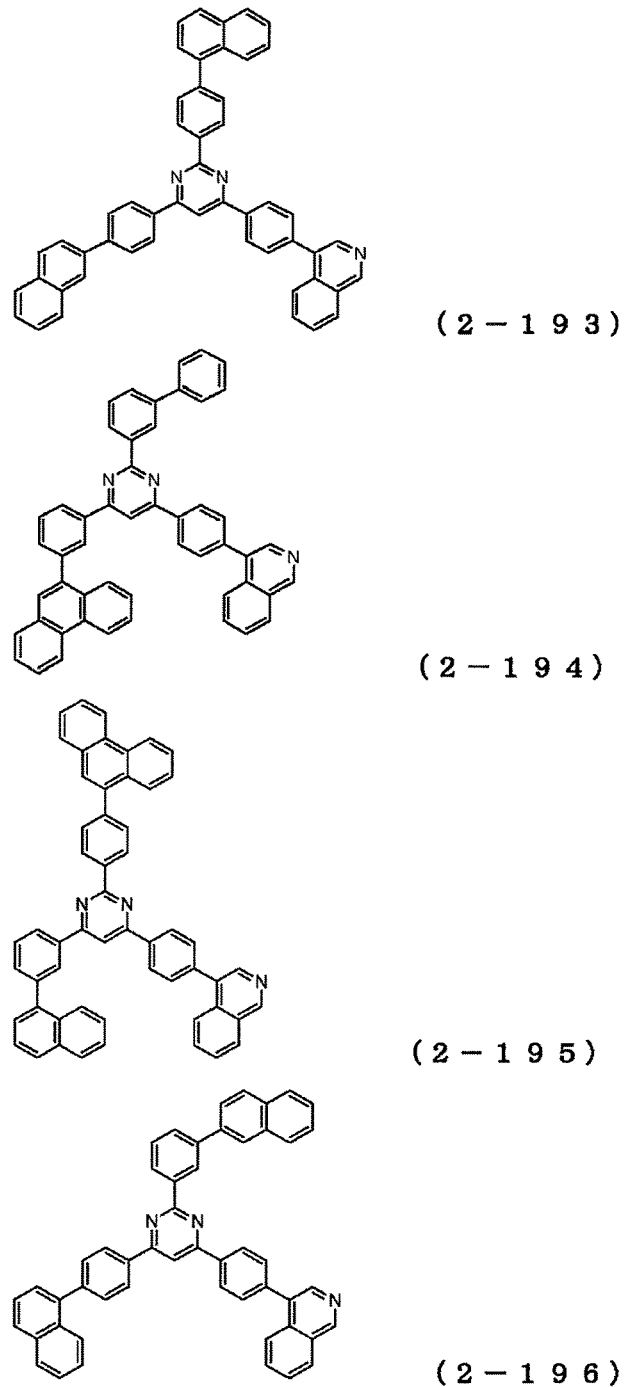
FIG. 66 is a view showing the structural formulas of Compounds (2-193) to (2-196) in the pyrimidine derivative of the general formula (2).
Figure 67:
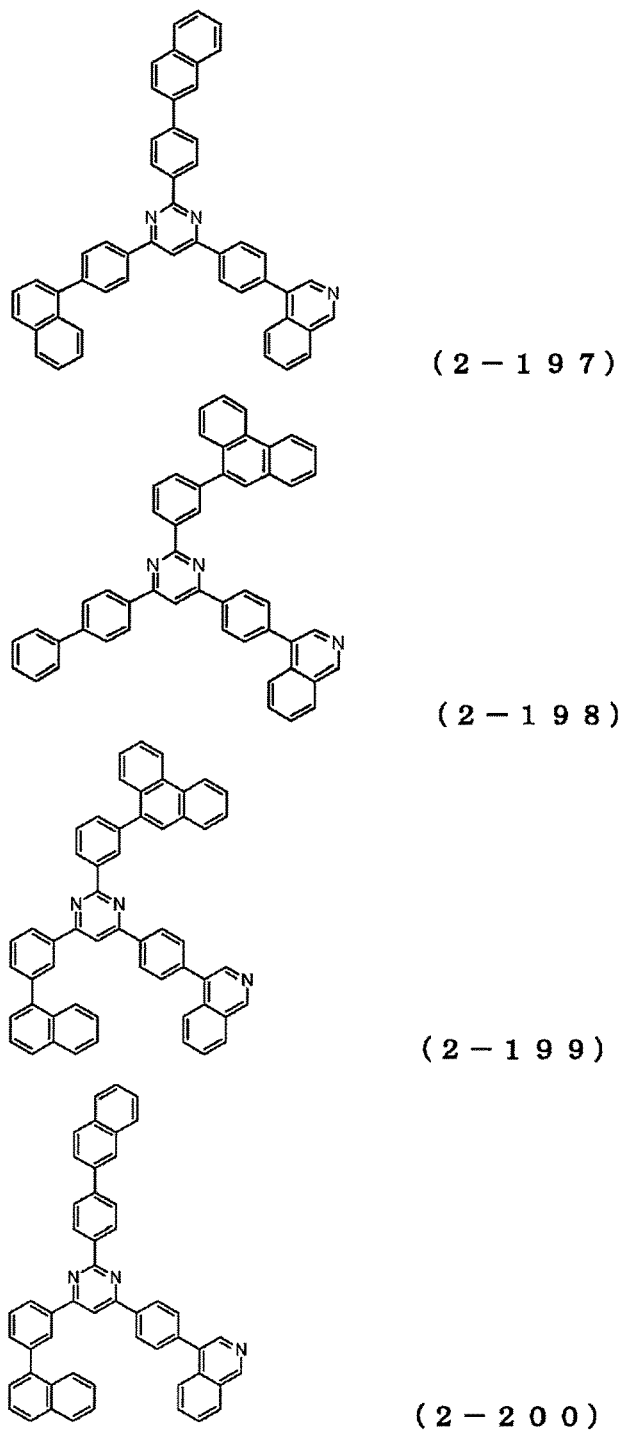
FIG. 67 is a view showing the structural formulas of Compounds (2-197) to (2-200) in the pyrimidine derivative of the general formula (2).
Figure 68:
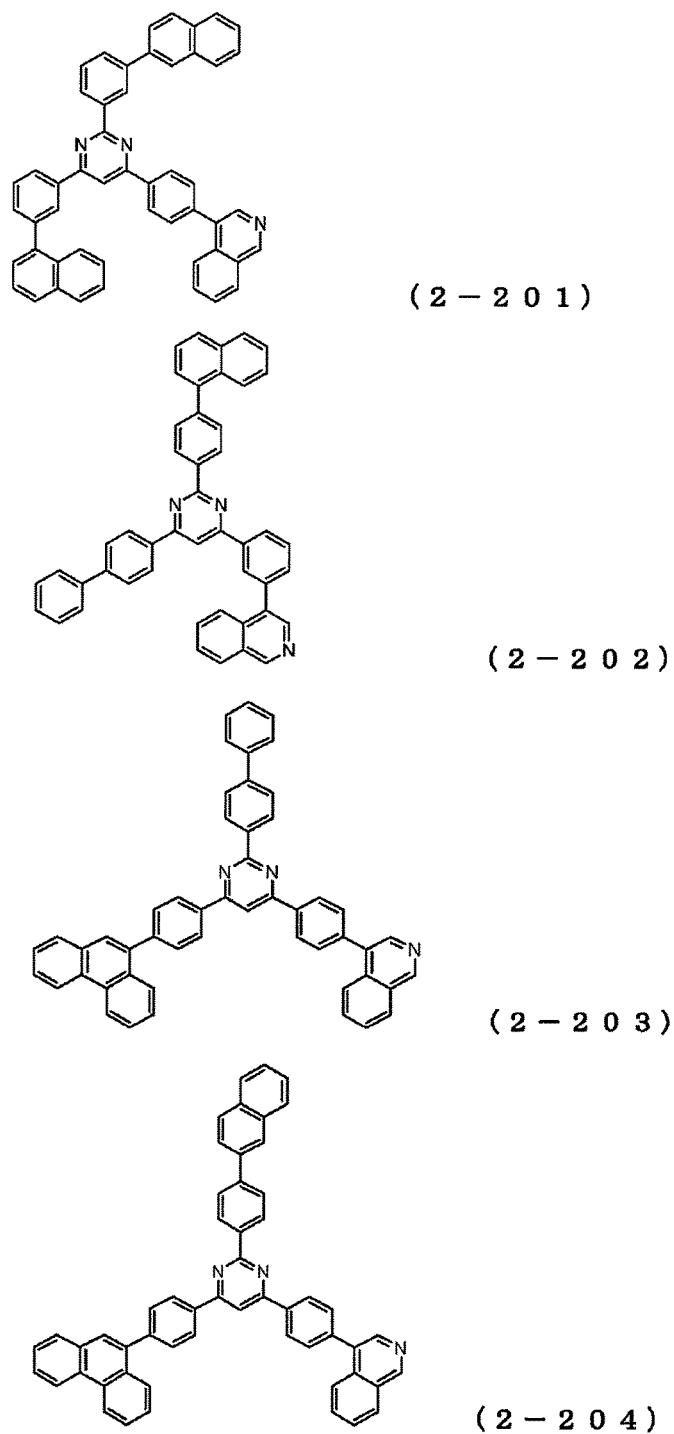
FIG. 68 is a view showing the structural formulas of Compounds (2-201) to (2-204) in the pyrimidine derivative of the general formula (2).
Figure 69:
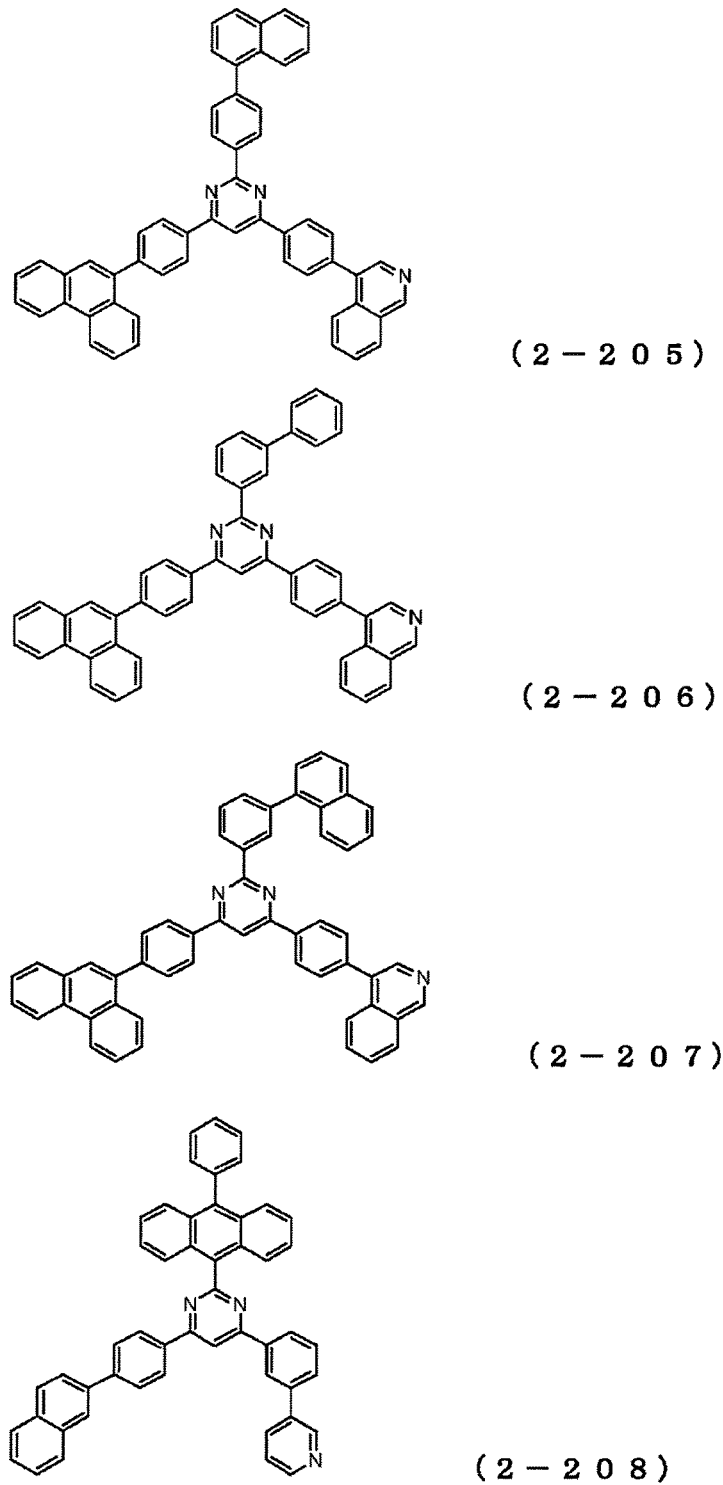
FIG. 69 is a view showing the structural formulas of Compounds (2-205) to (2-208) in the pyrimidine derivative of the general formula (2).
Figure 70:
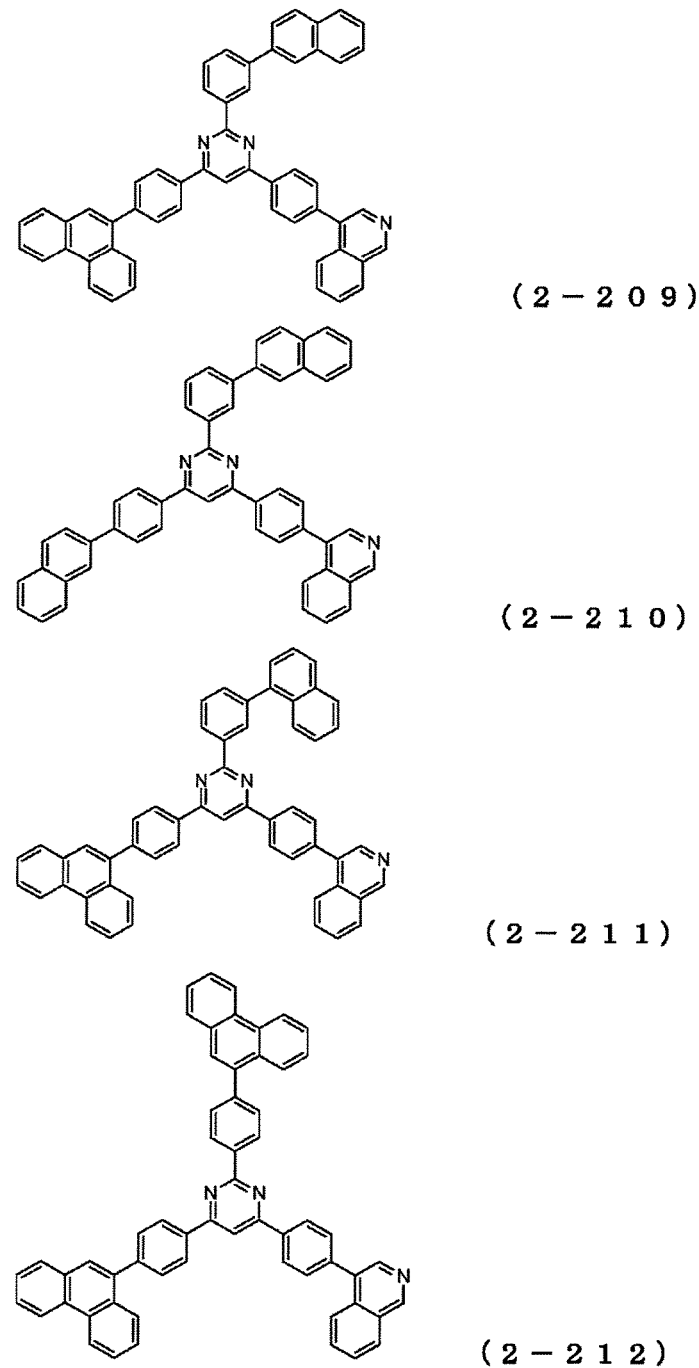
FIG. 70 is a view showing the structural formulas of Compounds (2-209) to (2-212) in the pyrimidine derivative of the general formula (2).
Figure 71:
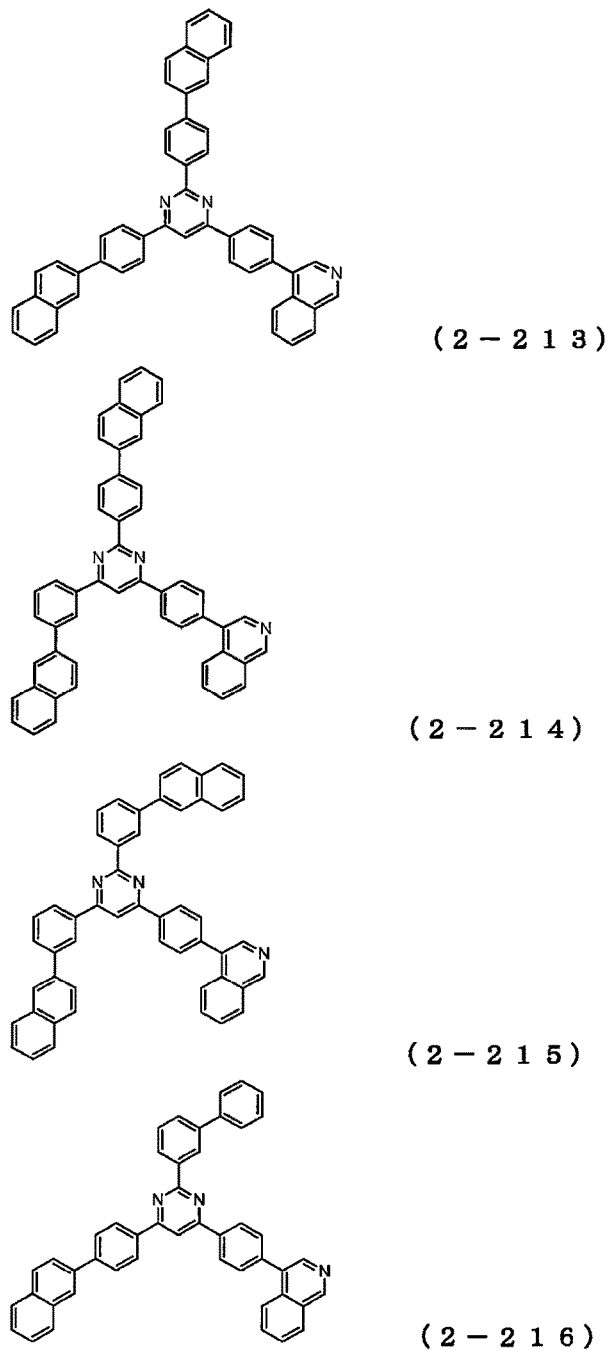
FIG. 71 is a view showing the structural formulas of Compounds (2-213) to (2-216) in the pyrimidine derivative of the general formula (2).
Figure 72:
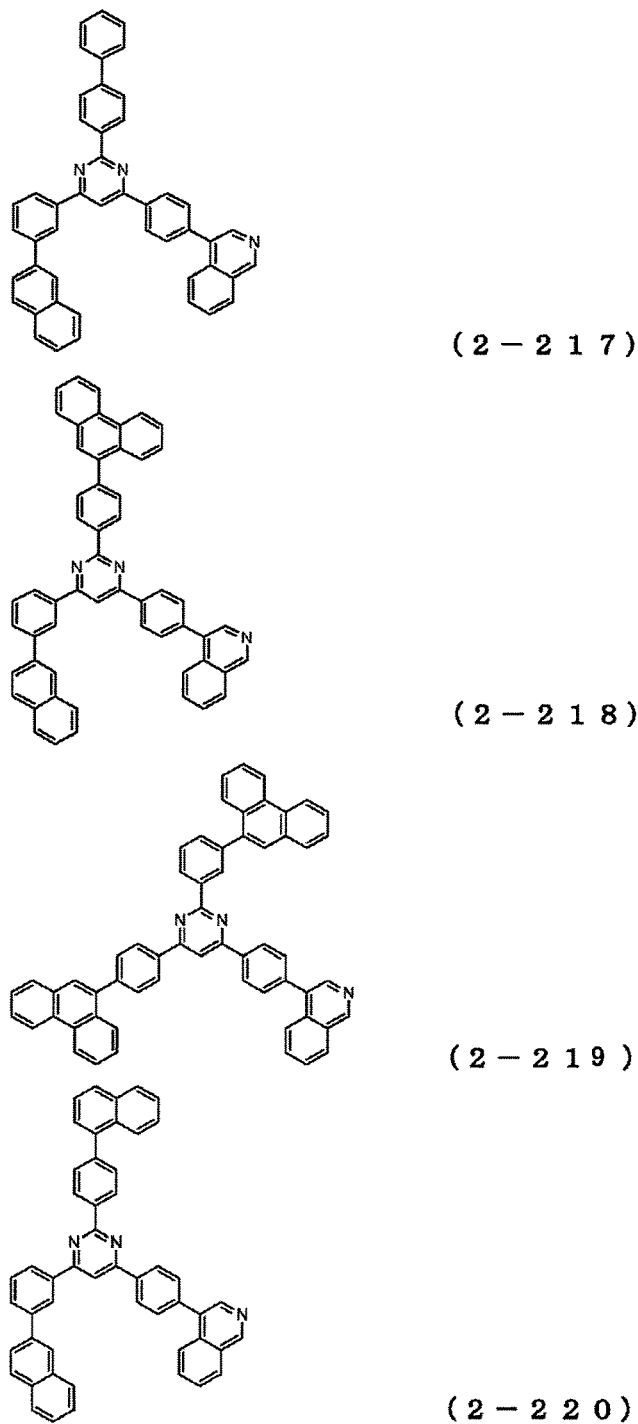
FIG. 72 is a view showing the structural formulas of Compounds (2-217) to (2-220) in the pyrimidine derivative of the general formula (2).
Figure 73:
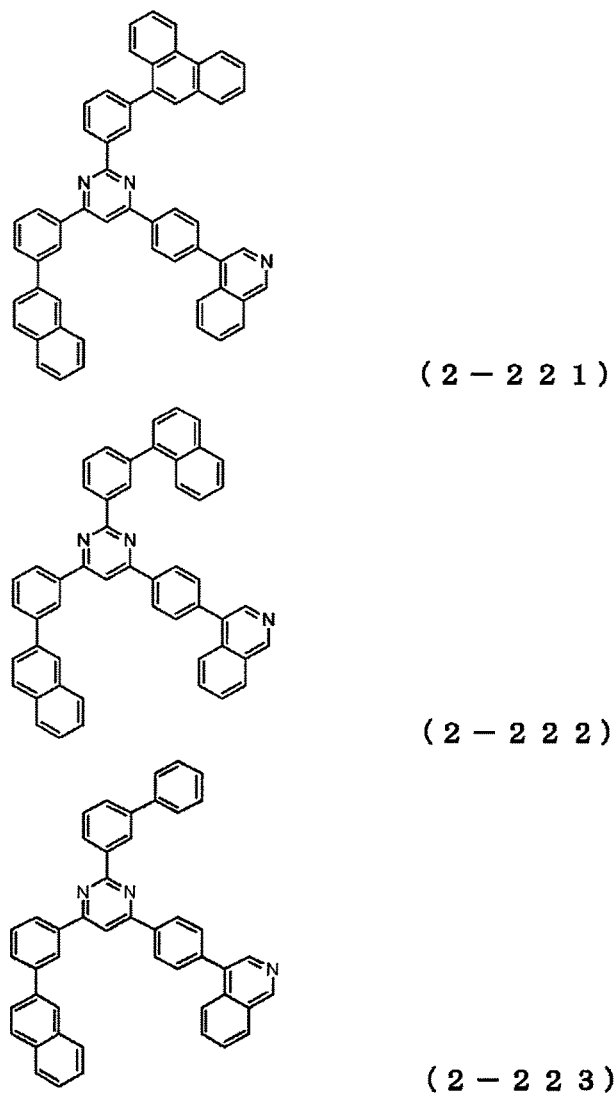
FIG. 73 is a view showing the structural formulas of Compounds (2-221) to (2-223) in the pyrimidine derivative of the general formula (2).
Figure 74:
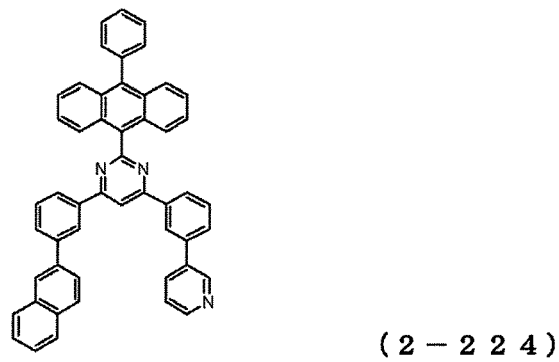
FIG. 74 is a view showing the structural formulas of Compounds (2-224) to (2-227) in the pyrimidine derivative of the general formula (2).
Figure 74:
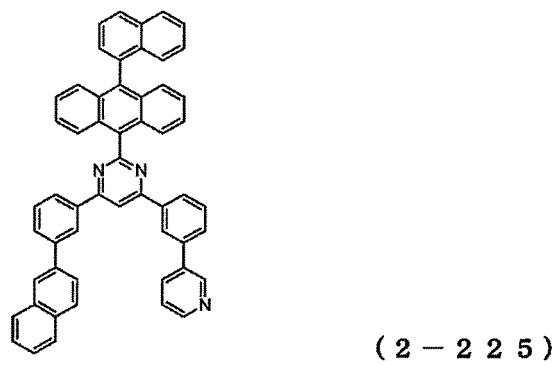
Figure 74:
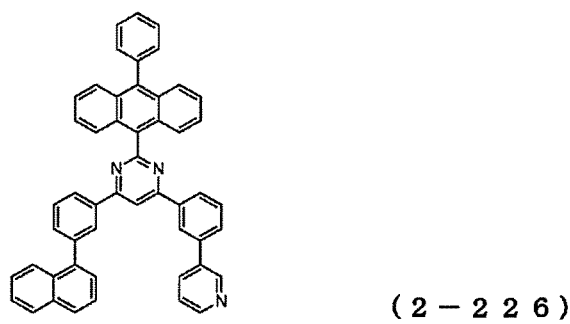
Figure 74:
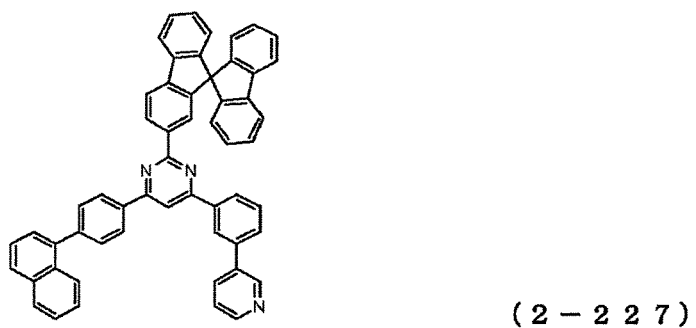
Figure 75:
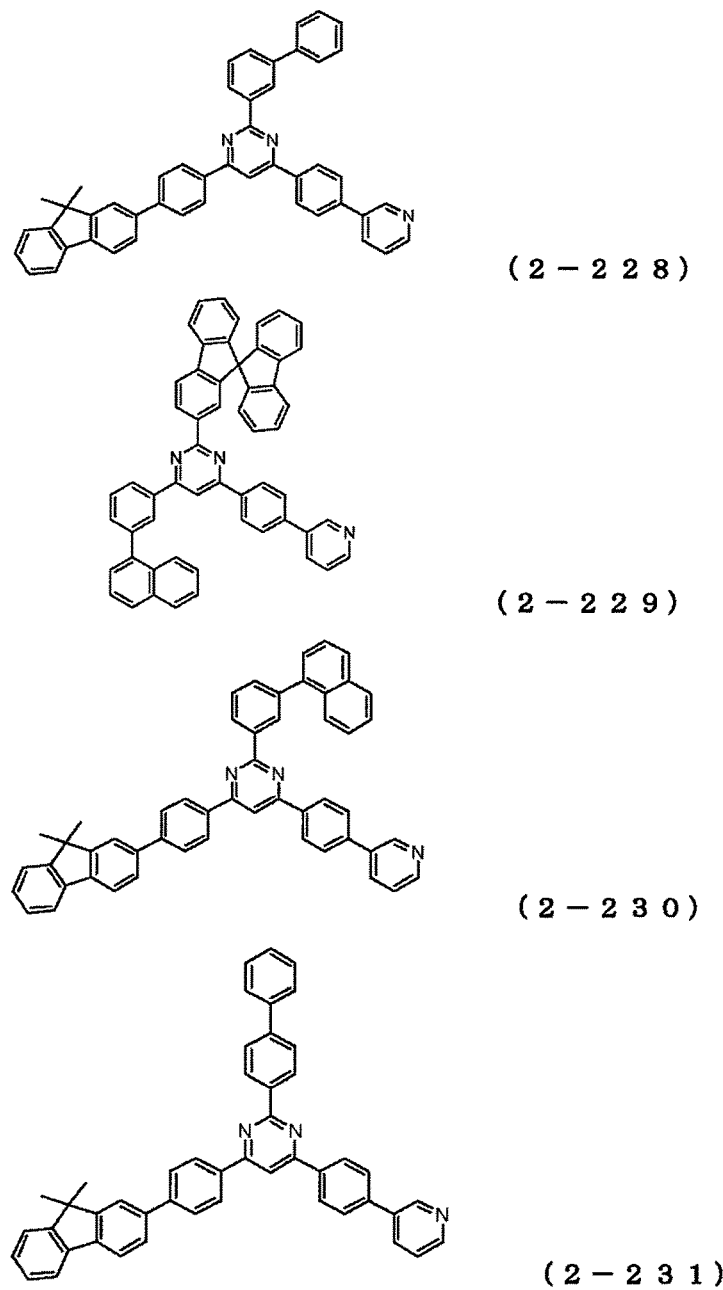
FIG. 75 is a view showing the structural formulas of Compounds (2-228) to (2-231) in the pyrimidine derivative of the general formula (2).
Figure 76:
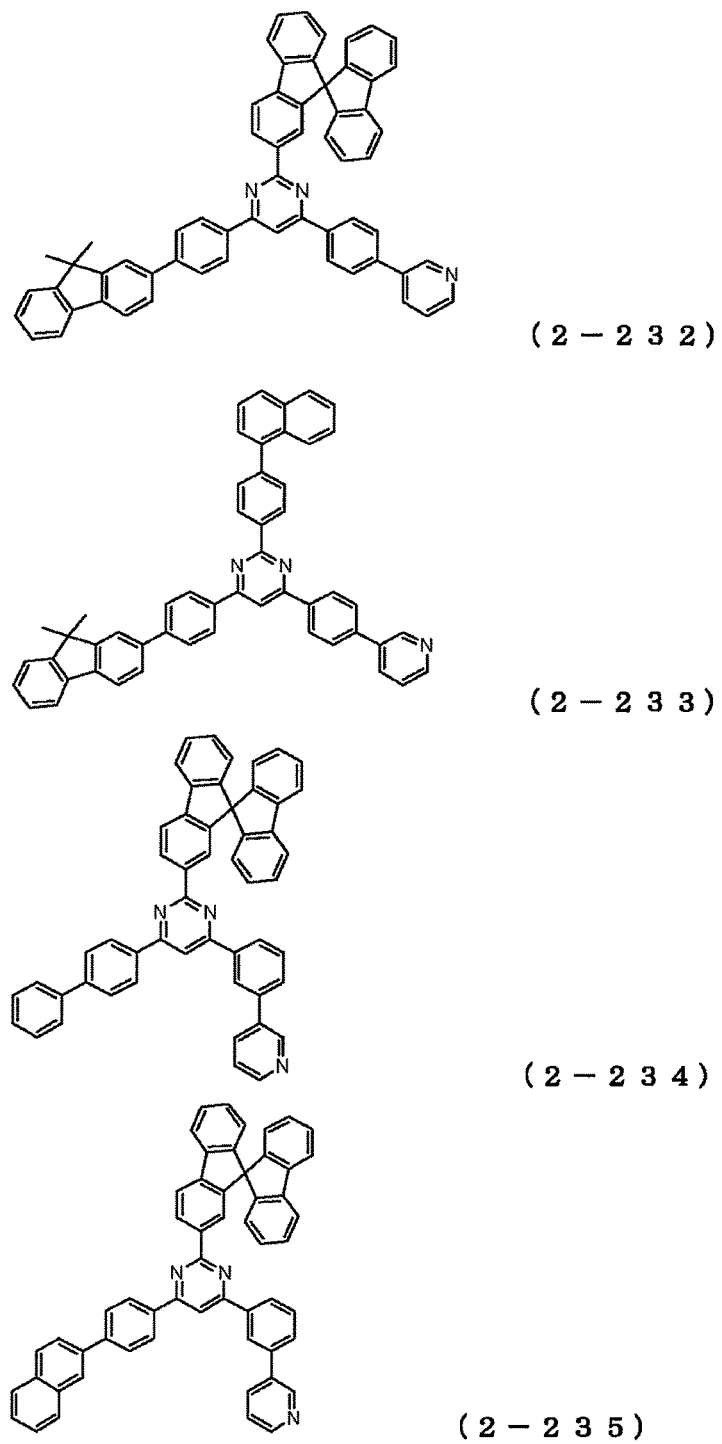
FIG. 76 is a view showing the structural formulas of Compounds (2-232) to (2-235) in the pyrimidine derivative of the general formula (2).
Figure 77:
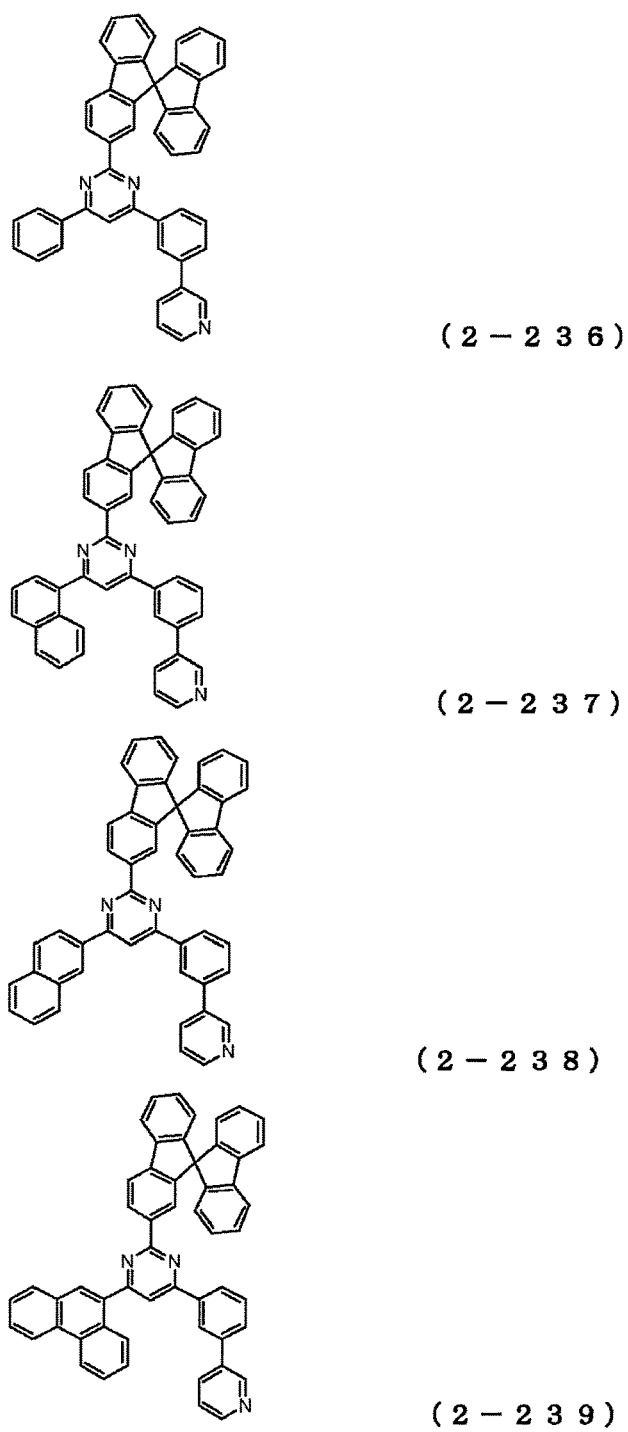
FIG. 77 is a view showing the structural formulas of Compounds (2-236) to (2-239) in the pyrimidine derivative of the general formula (2).
Figure 78:
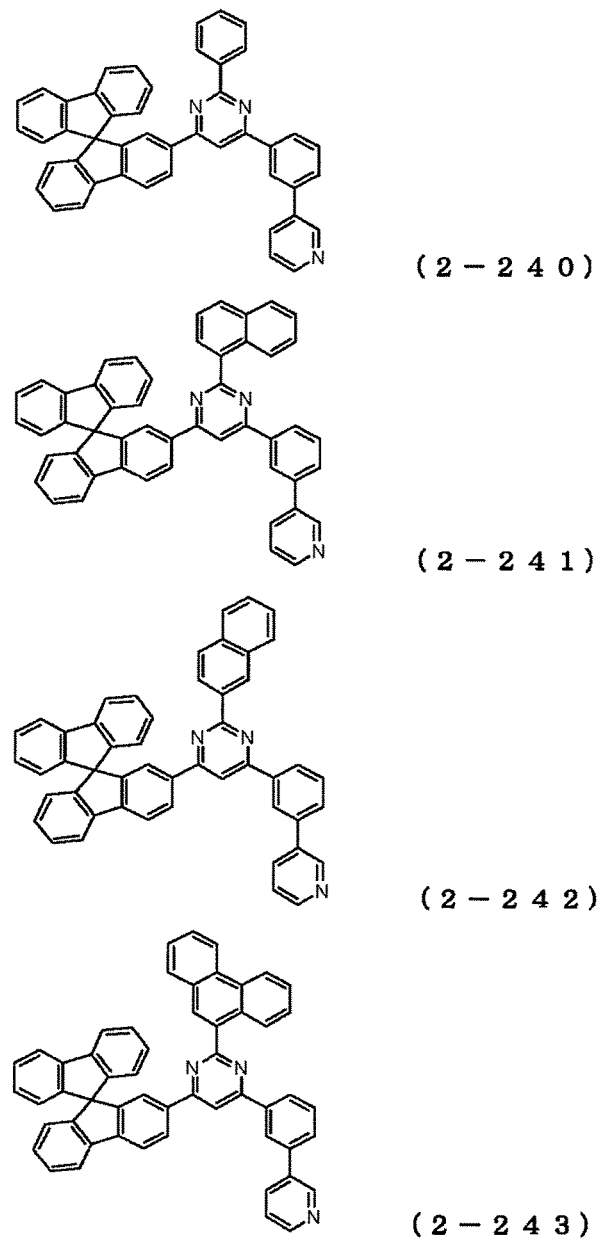
FIG. 78 is a view showing the structural formulas of Compounds (2-240) to (2-243) in the pyrimidine derivative of the general formula (2).
Figure 79:
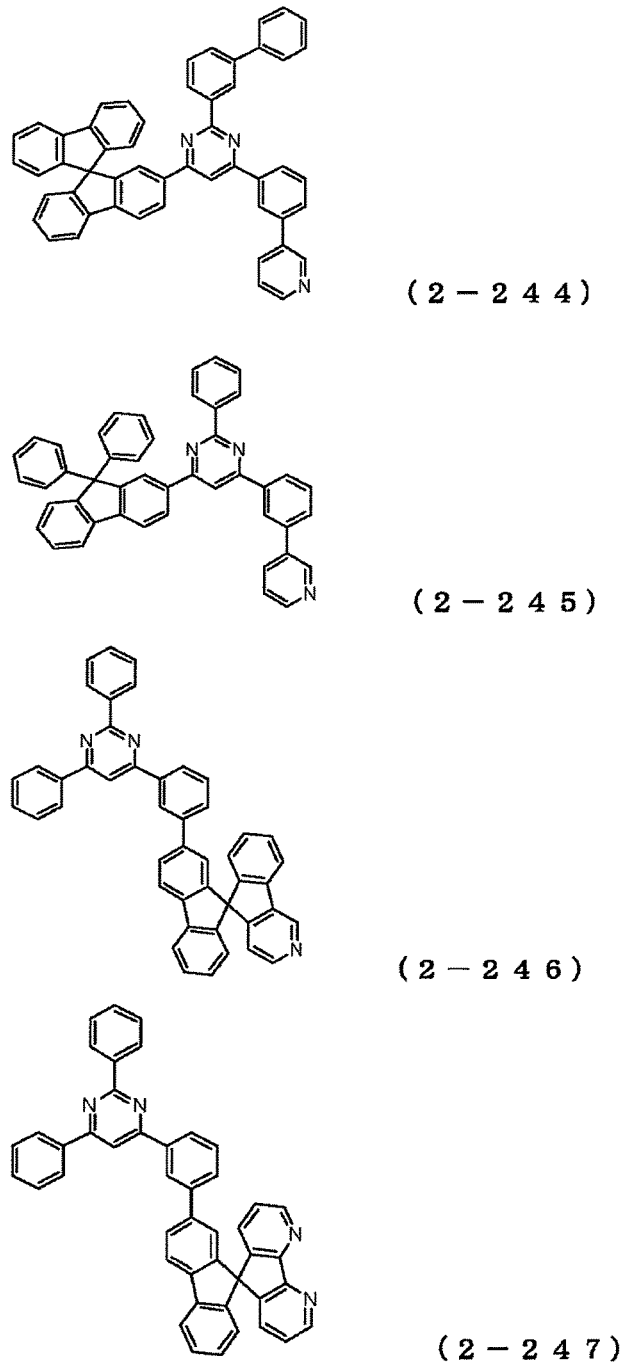
FIG. 79 is a view showing the structural formulas of Compounds (2-244) to (2-247) in the pyrimidine derivative of the general formula (2).
Figure 80:
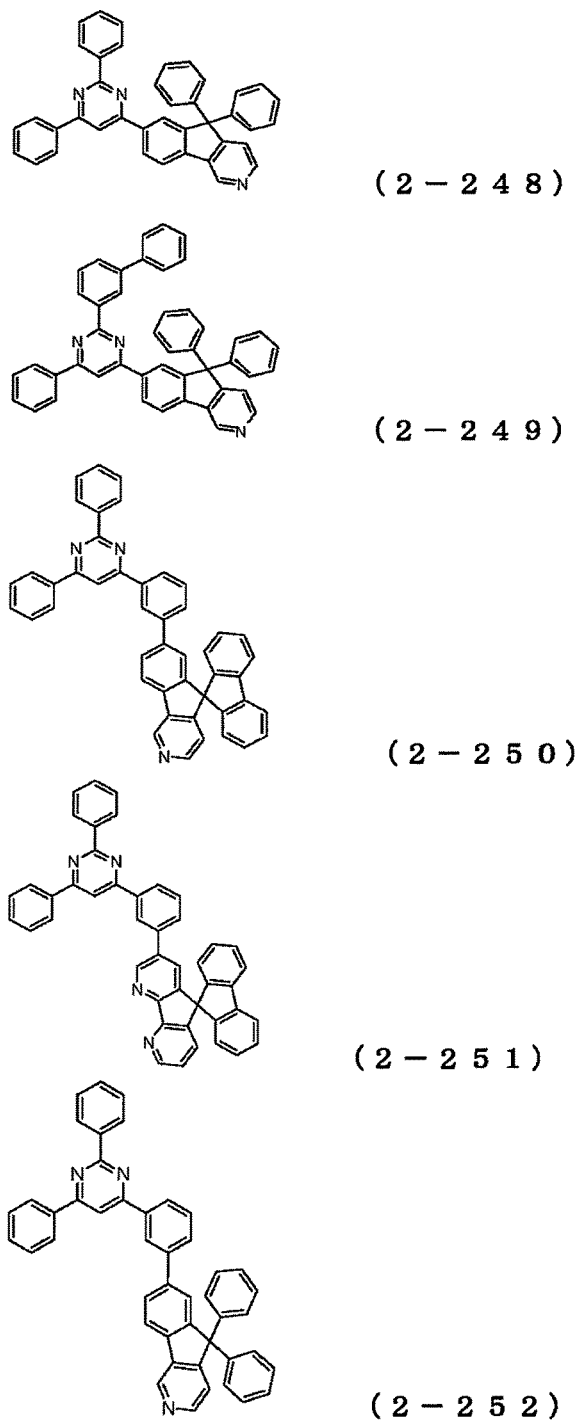
FIG. 80 is a view showing the structural formulas of Compounds (2-248) to (2-252) in the pyrimidine derivative of the general formula (2).
Figure 81:
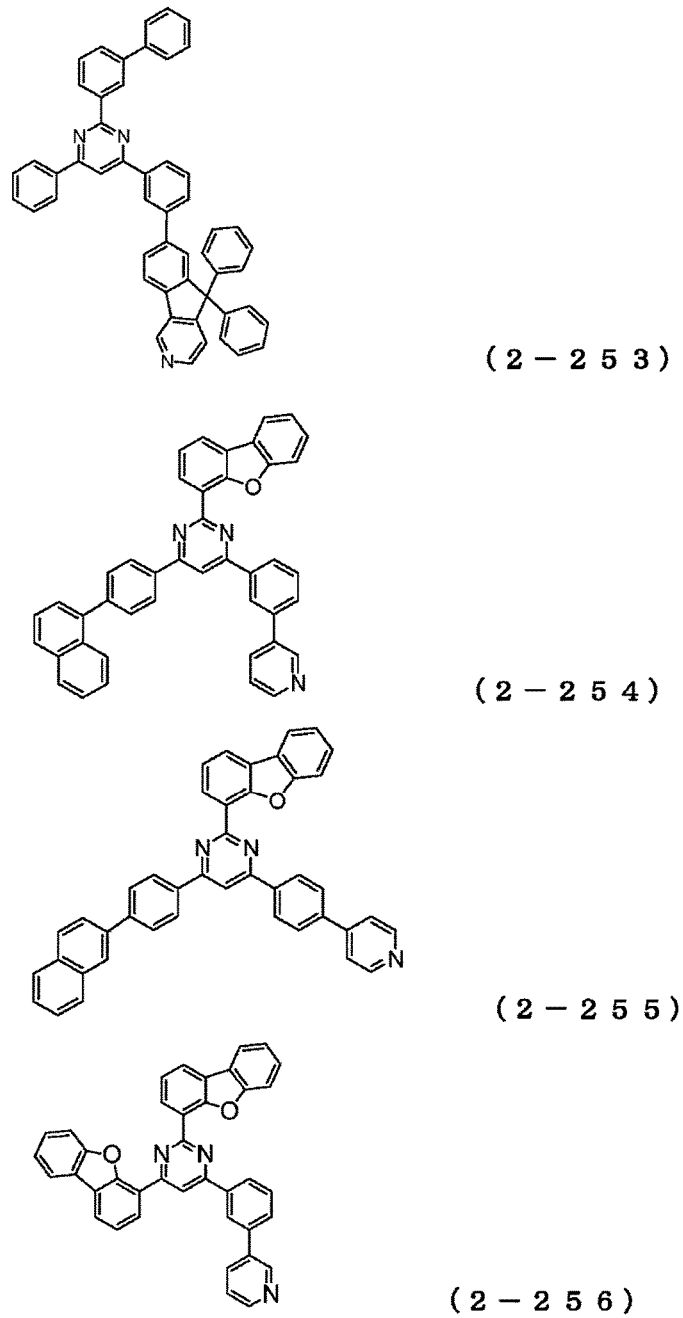
FIG. 81 is a view showing the structural formulas of Compounds (2-253) to (2-256) in the pyrimidine derivative of the general formula (2).
Figure 82:
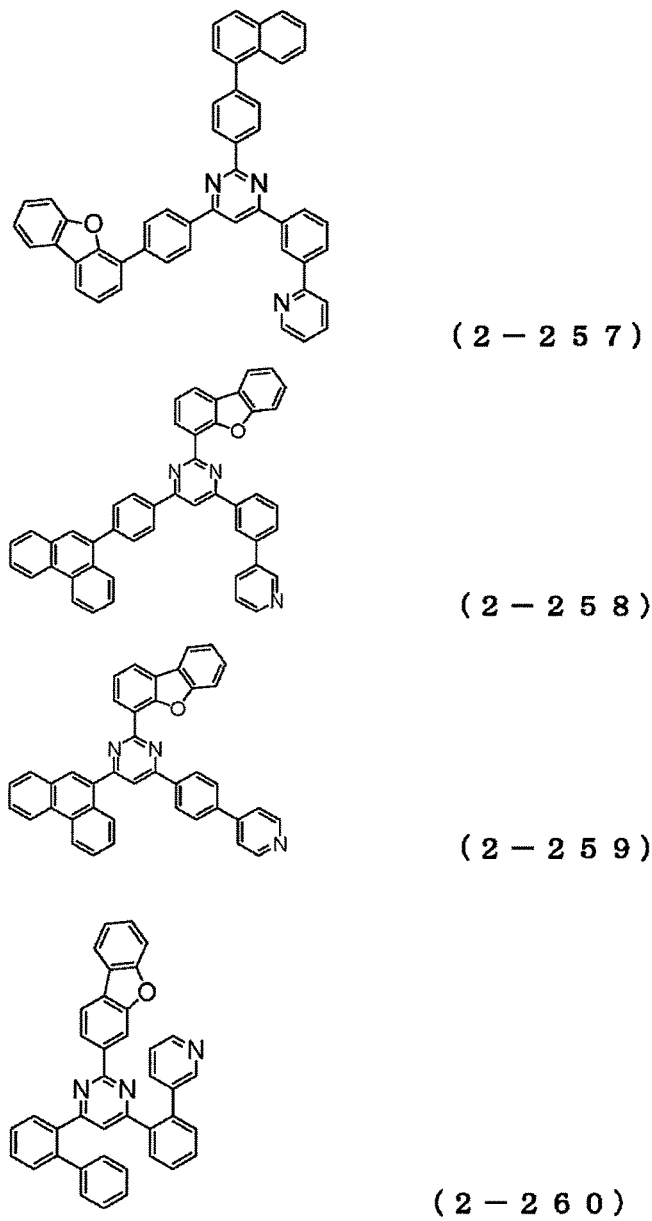
FIG. 82 is a view showing the structural formulas of Compounds (2-257) to (2-260) in the pyrimidine derivative of the general formula (2).
Figure 83:
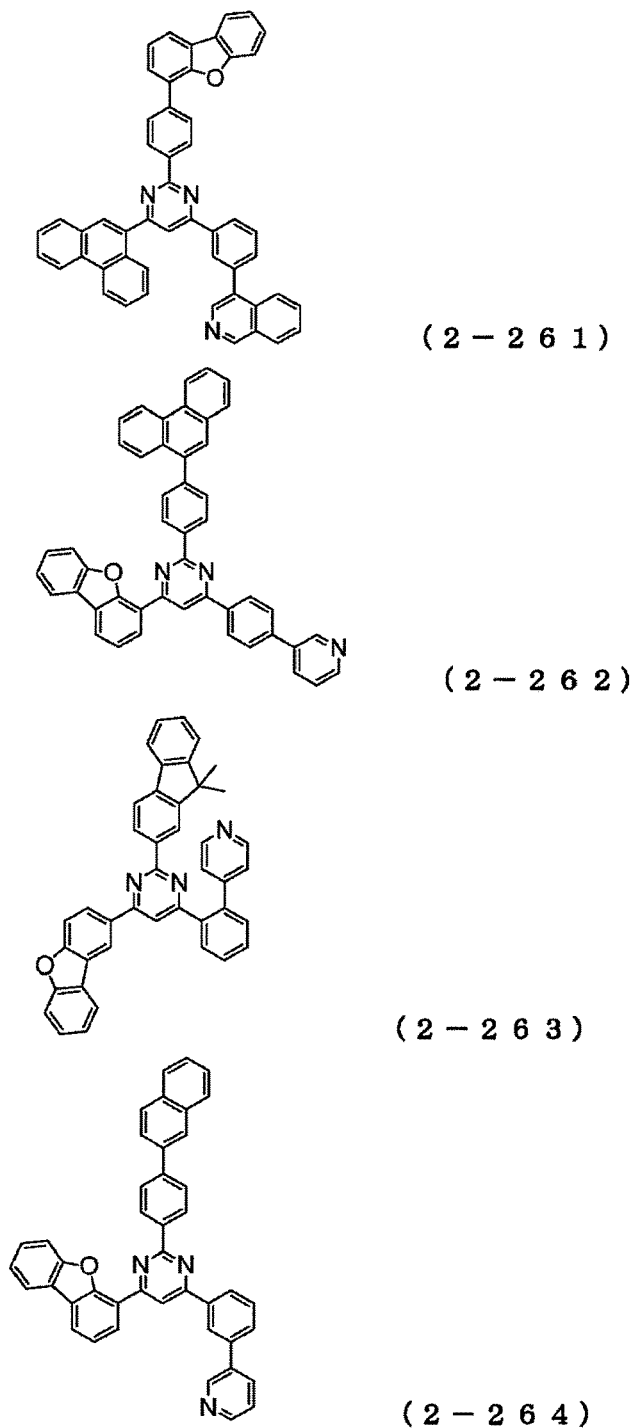
FIG. 83 is a view showing the structural formulas of Compounds (2-261) to (2-264) in the pyrimidine derivative of the general formula (2).
Figure 84:
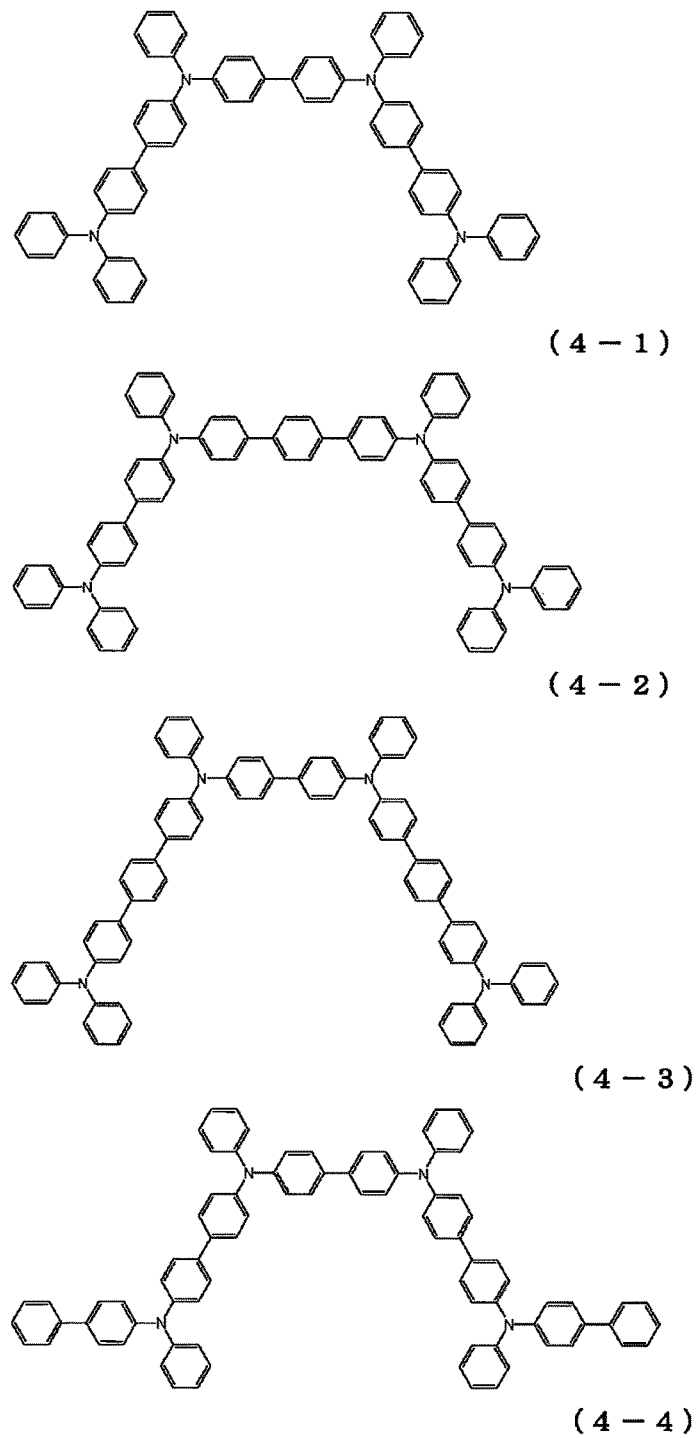
FIG. 84 is a view showing the structural formulas of Compounds (4-1) to (4-4) in the triarylamine compound of a general formula (4).
Figure 85:
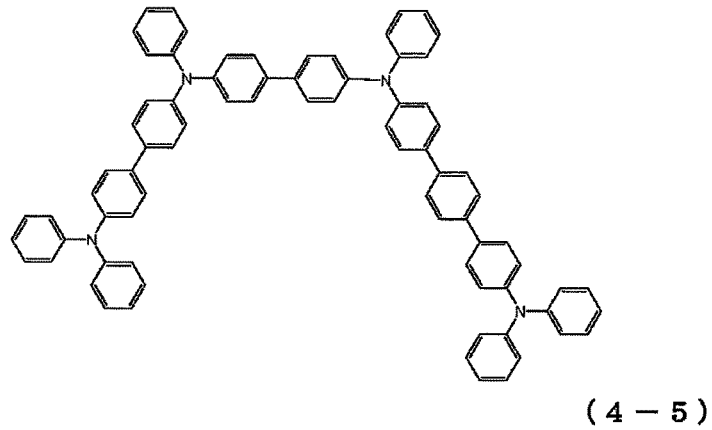
FIG. 85 is a view showing the structural formulas of Compounds (4-5) to (4-7) in the triarylamine compound of the general formula (4).
Figure 85:
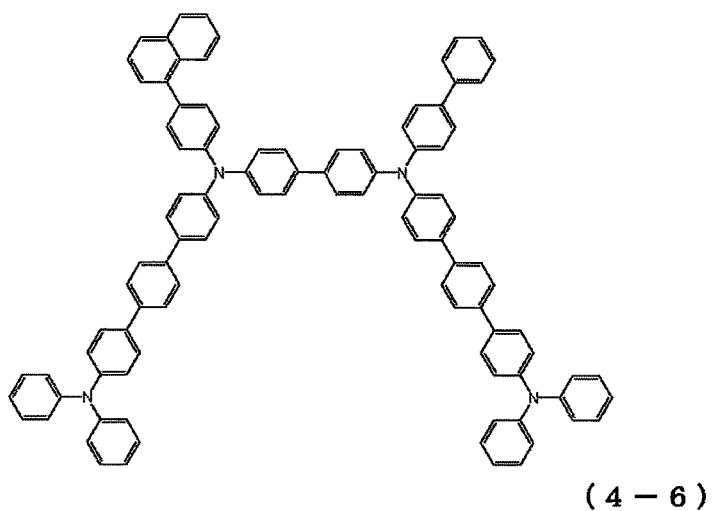
Figure 85:
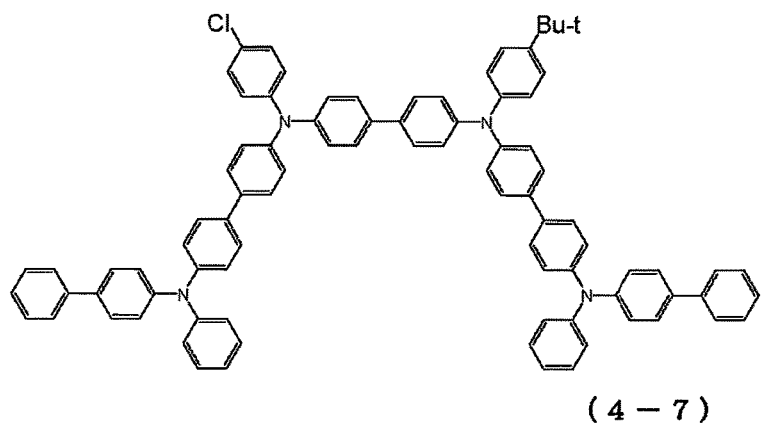
Figure 86:
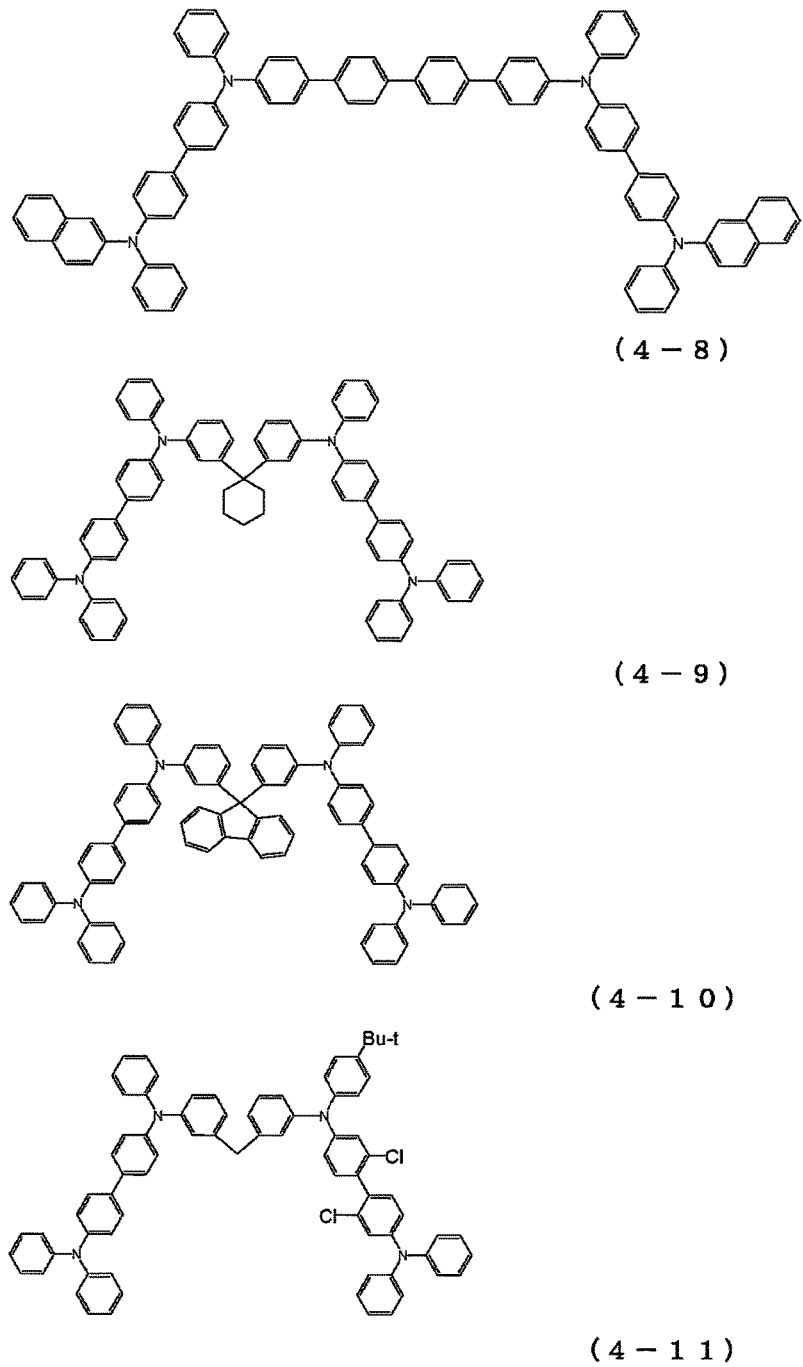
FIG. 86 is a view showing the structural formulas of Compounds (4-8) to (4-11) in the triarylamine compound of the general formula (4).
Figure 87:
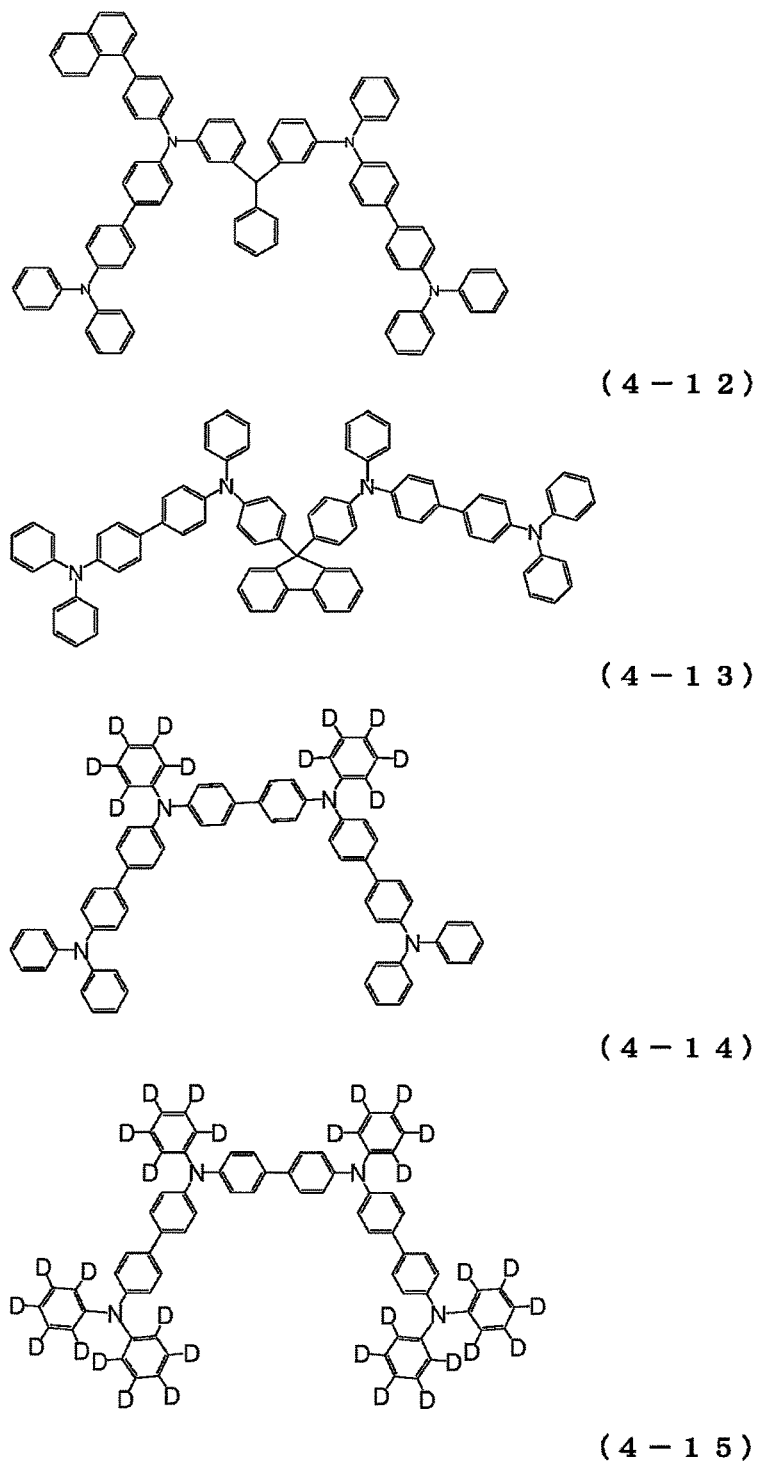
FIG. 87 is a view showing the structural formulas of Compounds (4-12) to (4-15) in the triarylamine compound of the general formula (4).
Figure 88:
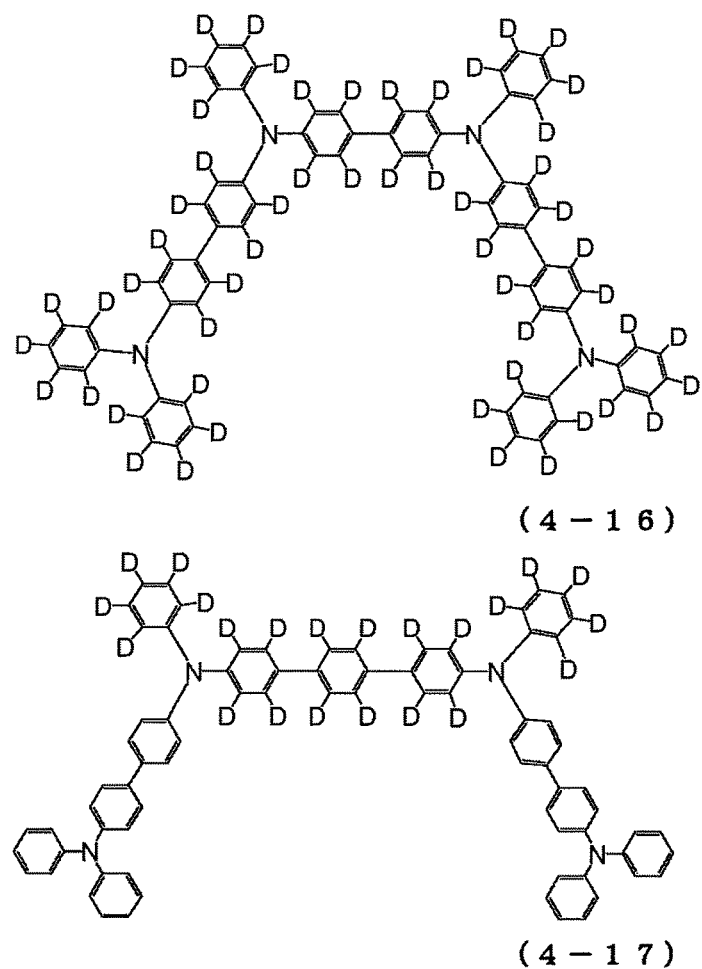
FIG. 88 is a view showing the structural formulas of Compounds (4-16) and (4-17) in the triarylamine compound of the general formula (4).

Specific examples of preferred compounds among the pyrimidine derivatives represented by the general formula (2) are shown in FIGS. 13 to 83, but the pyrimidine derivatives are not intended to be limited to these compounds. Compounds 2-1 to 2-49, 2-66 to 2-99, 2-103 to 2-105, 2-107 to 2-148, 2-150 to 2-182, and 2-184 to 2-264 correspond to the general formula (2a). Compounds 2-50 to 2-65, 2-100 to 2-102, 2-106, 2-149, and 2-183 correspond to the general formula (2b). D in the structural formulas represents deuterium.

The pyrimidine derivatives represented by the general formula (2) can be synthesized by a publicly known method (see PTL 6 and 7).

Each layer constituting the organic EL device of the present invention will be explained hereinbelow.

<Anode>

The anode 2 is formed on the transparent substrate 1 by vapor deposition of an electrode material with a large work function, such as ITO or gold.

<Hole Injection Layer>

The hole injection layer 3 is provided between the anode 2 and the first hole transport layer 4. The hole injection layer 3 can be formed using publicly known materials, for example, triphenylamine derivatives of a starburst type; various triphenylamine tetramers; porphyrin compounds represented by copper phthalocyanine; heterocyclic compounds having acceptor property, such as hexacyanoazatriphenylene; and coating-type polymer materials. Alternatively, the arylamine compound represented by the general formula (1), the below-described triarylamine compound represented by a general formula (4), or the below-described triarylamine compound represented by a general formula (5) can be also used.

Further, a material P-doped with trisbromophenylamine hexachloroantimony, a radialene derivative (see WO 2014/009310), or the like, or a polymer compound having the structure of a benzidine derivative such as TPD in a partial structure thereof can be used in combination with the above-described materials suitable for the hole injection layer.

The hole injection layer 3 can be obtained by using these materials and performing thin-film formation by a publicly known method such as a vapor deposition method, a spin coat method, and an ink jet method. The below-described layers may be likewise obtained by performing thin-film formation by a publicly known method such as a vapor deposition method, a spin coat method, and an ink jet method.

<Hole Transport Layer>

The hole transport layer is provided between the hole injection layer 3 and the luminous layer 6. In the present invention, the hole transport layer has a two-layer structure including the first hole transport layer 4 and the second hole transport layer 5.

(First Hole Transport Layer)

In the organic EL device of the present invention, the first hole transport layer can use publicly known hole transport materials. Specific examples of the publicly known hole transport materials are presented below;

benzidine derivatives, for example,
N,N'-diphenyl-N,N'-di(m-tolyl)benzidine (TPD),
N,N'-diphenyl-N,N'-di(α-naphthyl)benzidine (NPD), and
N,N,N',N'-tetrabiphenylylbenzidine;
1,1-bis[4-(di-4-tolylamino)phenyl]cyclohexane (TAPC); and various triphenylamine trimers and tetramers, for example, triarylamine compounds having 3 to 6 triarylamine structures in a molecule, the triarylamine structures being linked to each other via a single bond or a divalent group having no heteroatom, and triarylamine compounds having 2 triarylamine structures in a molecule, the triarylamine structures being linked to each other via a single bond or a divalent group having no heteroatom.

Among the above-described publicly known materials, it is preferred that triarylamine compounds having 3 to 6 triarylamine structures in a molecule, the triarylamine structures being linked to each other via a single bond or a divalent group having no heteroatom (can be abbreviated below as "triarylamine compounds having 3 to 6 triarylamine structures"); and triarylamine compounds having 2 triarylamine structures in a molecule, the triarylamine structures being linked to each other via a single bond or a divalent group having no heteroatom (can be abbreviated below as "triarylamine compounds having 2 triarylamine structures") be used.

The below-described triarylamine compounds represented by the general formula (4) are preferred as the triarylamine compounds having 3 to 6 triarylamine structures. This is because such compounds excel in hole transport property, thin film stability and heat resistance and are also easy to synthesize.

The below-described triarylamine compounds represented by the general formula (5) are preferred as the triarylamine compounds having 2 triarylamine structures. This is because such compounds excel in hole transport property, thin film stability and heat resistance and are also easy to synthesize.

Further, for example, a material P-doped with trisbromophenylamine hexachloroantimony, a radialene derivative (see WO 2014/009310), or the like, or a polymer compound having the structure of a benzidine derivative such as TPD in a partial structure thereof can be used in combination with the above-described materials suitable for the first hole transport layer.

In the present invention, a condition that the compound to be used for forming the first hole transport layer 4 and the compound to be used for forming the below-described second hole transport layer 5 be different from each other needs to be fulfilled, but as long as this condition is fulfilled, for example, an arylamine compound corresponding to the general formula (1) may be used for the first hole transport layer 4.

The above-described materials may be used individually to form a film, or may be used in a mixture with other materials to form a film. Further, a laminated structure may be obtained which includes layers each formed from a single material, which includes layers each formed from a mixture or materials, or which includes layers each formed from a single material and layers each formed from a mixture of materials.

The triarylamine compound represented by the general formula (4);

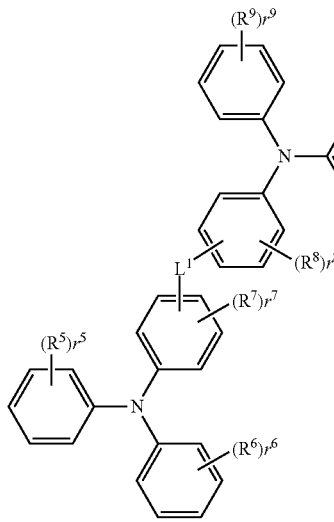 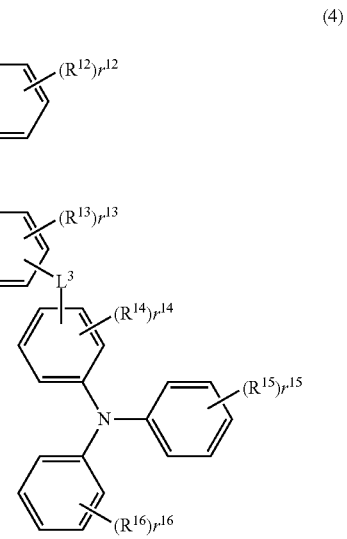

(4)

The triarylamine compound represented by the general formula (4) has 4 triarylamine structures.

In the general formula (4), $r^5$ to $r^{16}$ represent the number of substituents $R^5$ to $R^{16}$ bonded to the aromatic ring. $r^5$, $r^6$, $r^9$, $r^{12}$, $r^{15}$, and $r^{16}$ each represent an integer of 0 to 5. $r^7$, $r^8$, $r^{10}$, $r^{11}$, $r^{13}$, and $r^{14}$ each represent an integer of 0 to 4.

When $r^{5s}$ to $r^{16}$ are 0, it means that $R^5$ to $R^{16}$ are not present on the aromatic ring, that is, that the aromatic ring is not substituted by the groups represented by $R^5$ to $R^{16}$.

When $r^5$, $r^6$, $r^9$, $r^{12}$, $r^{15}$, and $r^{16}$ each are an integer of 2 to 5, or $r^7$, $r^8$, $r^{10}$, $r^{11}$, $r^{13}$, and $r^{14}$ each are an integer of 2 to 4, it means that a plurality of $R^5$ to $R^{16}$ is bonded to the same aromatic ring (benzene ring). When the plurality of these groups is present on the same aromatic ring, the plurality of substituents may be present independently from each other, or may be bonded to each other via a single bond, a substituted or unsubstituted methylene group, an oxygen atom, or a sulfur atom to form a ring. For example, a plurality of substituents may be bonded to each other to form a naphthalene ring, as in the below-described Exemplary Compound 4-8.

Further, $R^5$ to $R^{16}$ substituted in the aromatic ring each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group. The alkyl group having 1 to 6 carbon atoms, the alkenyl group having 2 to 6 carbon atoms, and the alkyloxy group having 1 to 6 carbon atoms may be straight-chain or branched.

Specific examples of the alkyl group having 1 to 6 carbon atoms, the cycloalkyl group having 5 to 10 carbon atoms, or the alkenyl group having 2 to 6 carbon atoms, which is represented by $R^5$ to $R^{16}$, include a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, and a 2-butenyl group, etc.

Specific examples of the alkyloxy group having 1 to 6 carbon atoms or the cycloalkyloxy group having 5 to 10 carbon atoms, which is represented by $R^5$ to $R^{16}$, include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, etc.

The aromatic hydrocarbon group, aromatic heterocyclic group, or condensed polycyclic aromatic group represented by $R^5$ to $R^{16}$ can be exemplified by the same ones as those illustrated in relation to the aromatic hydrocarbon group, aromatic heterocyclic group, or condensed polycyclic aromatic group represented by $Ar^1$ to $Ar^4$ in the general formula (1).

Specific examples of the aryloxy group represented by $R^5$ to $R^{16}$ include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group, etc.

The alkyl group having 1 to 6 carbon atoms, cycloalkyl group having 5 to 10 carbon atoms, alkenyl group having 2 to 6 carbon atoms, alkyloxy group having 1 to 6 carbon atoms, cycloalkyloxy group having 5 to 10 carbon atoms, aromatic hydrocarbon group, aromatic heterocyclic group, condensed polycyclic aromatic group, or aryloxy group represented by $R^5$ to $R^{16}$ may have a substituent. The substituents can be exemplified by the same ones as those illustrated as the substituents optionally possessed by the aromatic hydrocarbon group, aromatic heterocyclic group, or condensed polycyclic aromatic group represented by $A^1$ to $Ar^4$ in the general formula (1). Modes which the substituents can adopt are also the same.

In the general formula (4), $L^1$ to $L^3$ are bridging groups that bond two triarylamine skeletons, and each represent a single bond or a divalent group represented by any one of the following structural formulas (B) to (G). The divalent groups represented by the following structural formulas (B) to (G) may be unsubstituted, or may be substituted with deuterium as in the below-described Exemplary Compound 4-17.

(B)

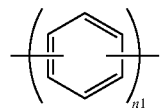

In this formula, n1 represents an integer of 1 to 3.

(C)

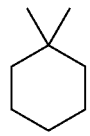

(D)

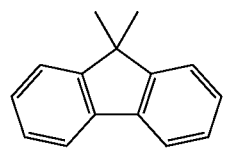

(E)

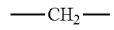

(F)

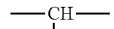

(G)

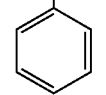

Specific examples of preferred compounds among the triarylamine compounds represented by the general formula (4) are shown in FIGS. 84 to 88, but the triarylamine compounds represented by the general formula (4) are not limited to these compounds. D in the structural formula represents deuterium.

Figure 89:
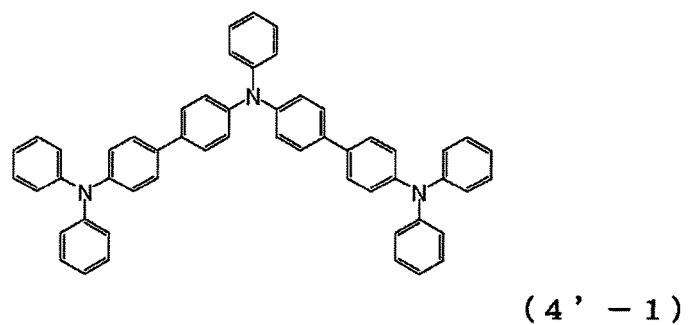
FIG. 89 is a view showing the structural formulas of Compounds (4'-1) and (4'-2) in the triarylamine compound other than that of the general formula (4).
Figure 89:
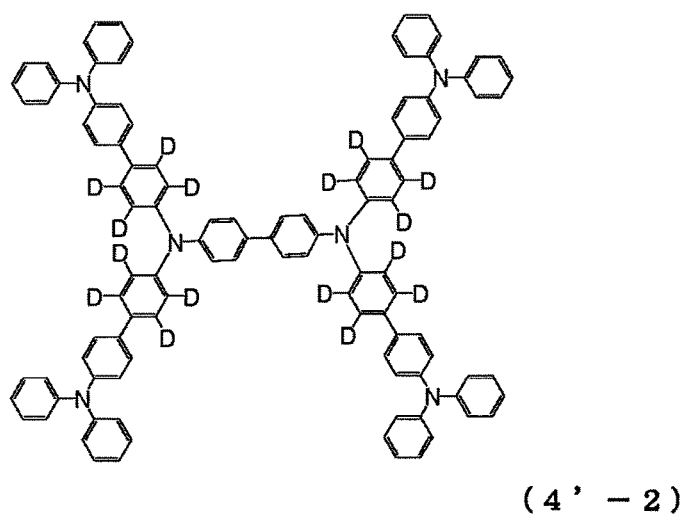
Figure 90:
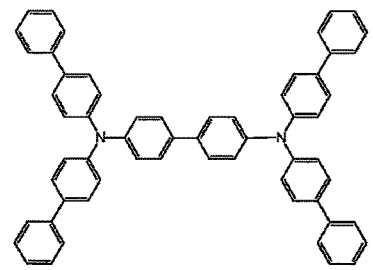
FIG. 90 is a view showing the structural formulas of Compounds (5-1) to (5-4) in the triarylamine compound of a general formula (5).
Figure 90:
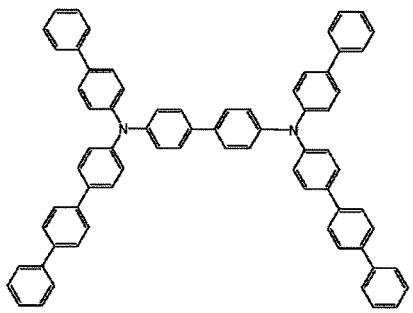
Figure 90:
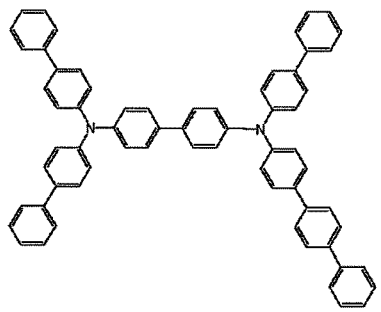
Figure 90:
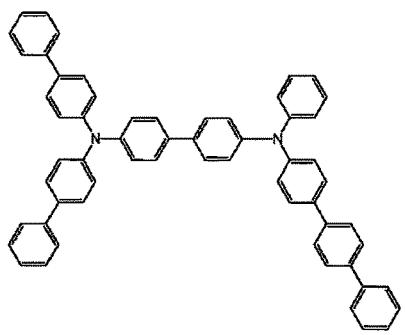
Figure 91:
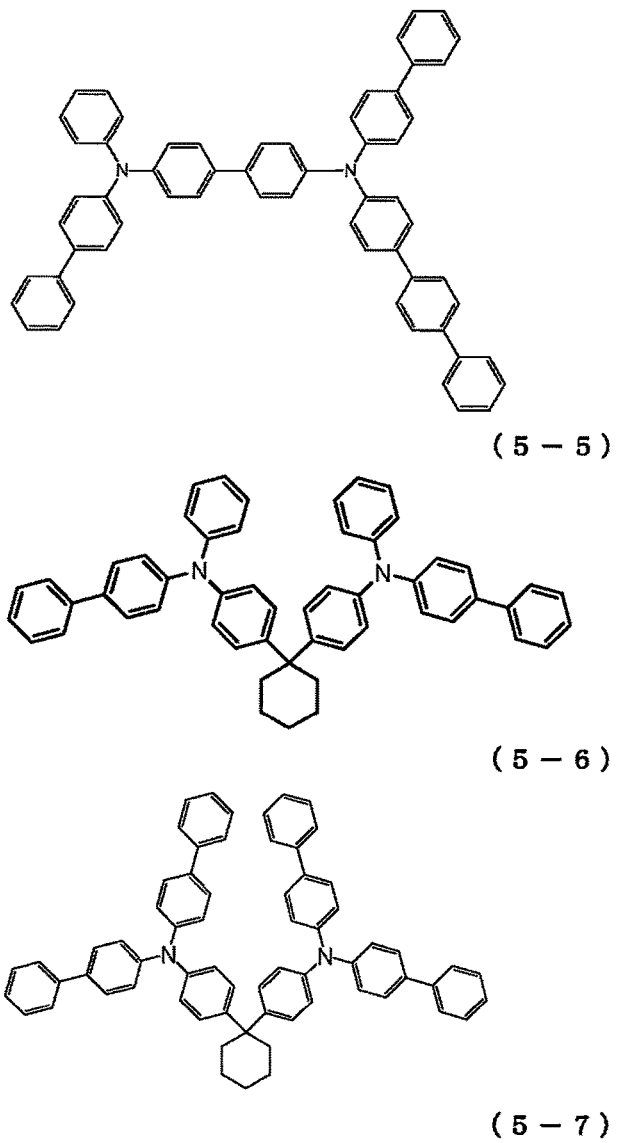
FIG. 91 is a view showing the structural formulas of Compounds (5-5) to (5-7) in the triarylamine compound of the general formula (5).
Figure 92:
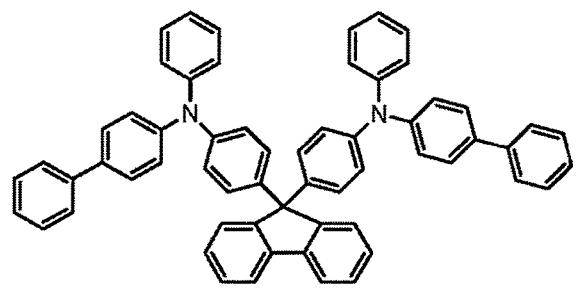
FIG. 92 is a view showing the structural formulas of Compounds (5-8) to (5-10) in the triarylamine compound of the general formula (5).
Figure 92:
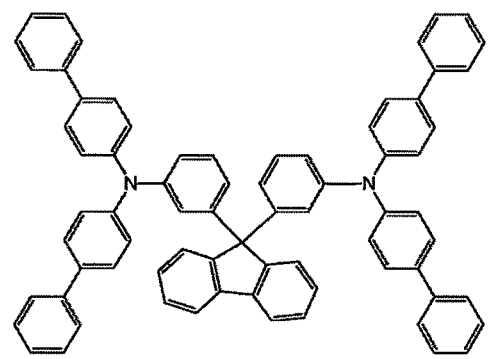
Figure 92:
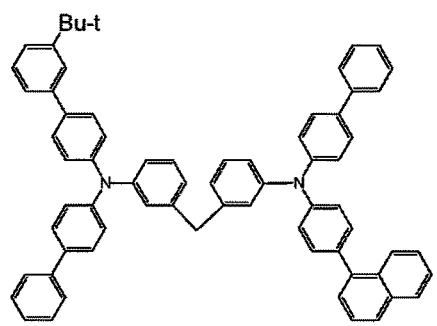
Figure 93:
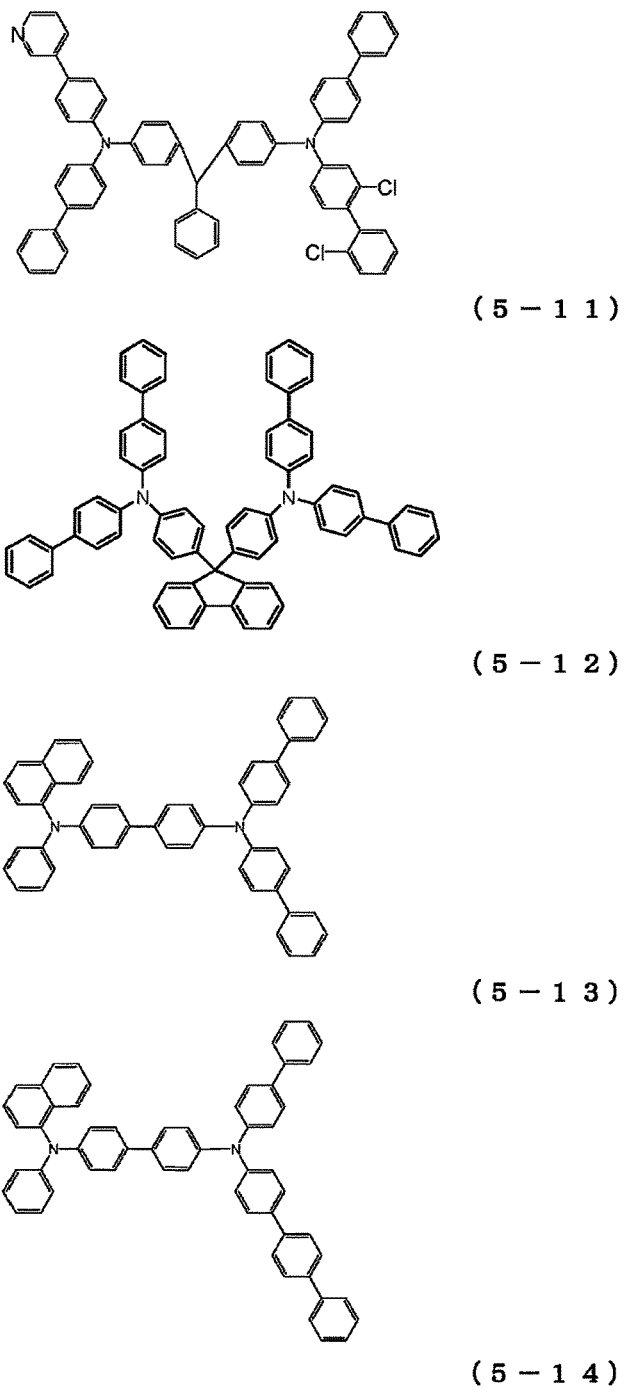
FIG. 93 is a view showing the structural formulas of Compounds (5-11) to (5-14) in the triarylamine compound of the general formula (5).
Figure 94:
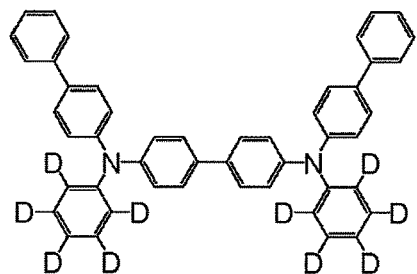
FIG. 94 is a view showing the structural formulas of Compounds (5-15) to (5-18) in the triarylamine compound of the general formula (5).
Figure 94:
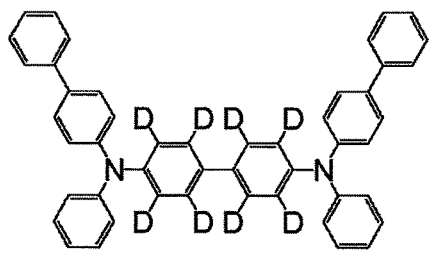
Figure 94:
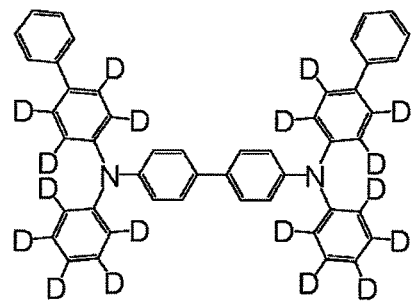
Figure 94:
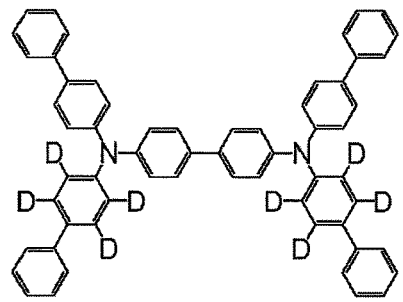
Figure 95:
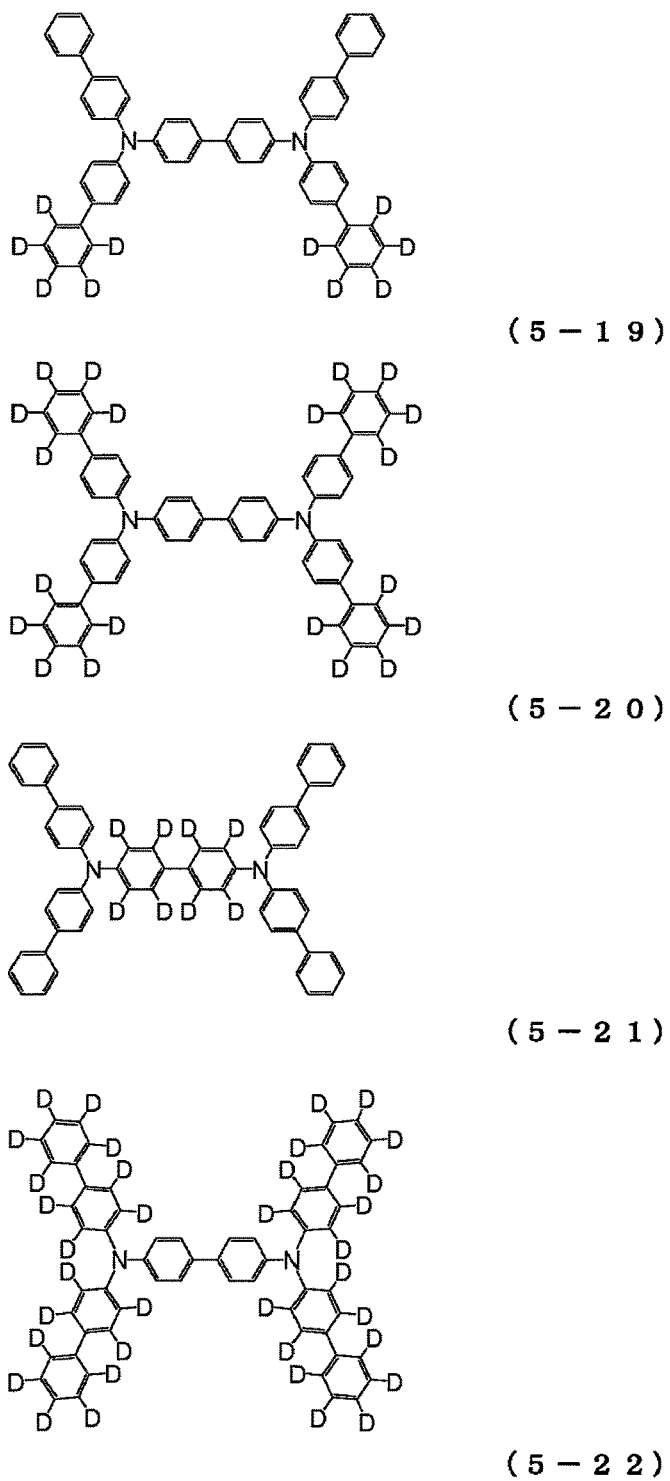
FIG. 95 is a view showing the structural formulas of Compounds (5-19) to (5-22) in the triarylamine compound of the general formula (5).
Figure 96:
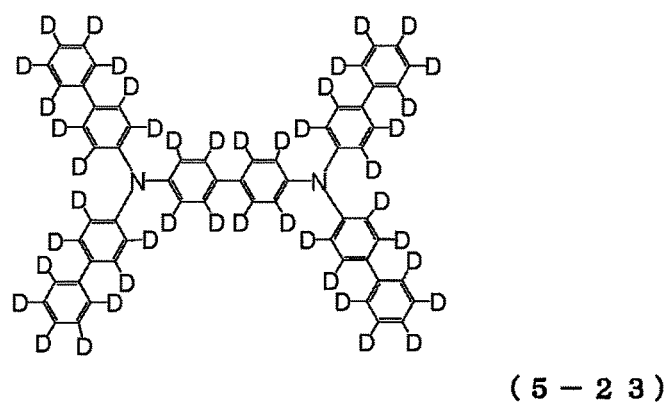
FIG. 96 is a view showing the structural formula of Compound (5-23) in the triarylamine compound of the general formula (5).

Specific examples of preferred compounds, other than the triarylamine compounds represented by the general formula (4), among the triarylamine compounds having 3 to 6 triarylamine structures are shown in FIG. 89, but the triarylamine compounds having 3 to 6 triarylamine structures are not limited to these compounds.

The triarylamine compound represented by the general formula (5);

(5)

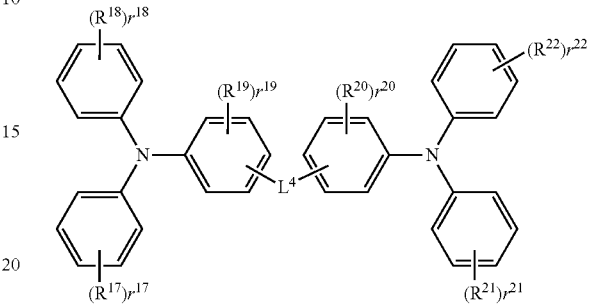

The triarylamine compound represented by the general formula (5) has 2 triarylamine structures.

In the general formula (5), $r^{18}$ to $r^{22}$ represent the number of groups $R^{18}$ to $R^{22}$ bonded to the aromatic ring. $r^{17}$, $r^{18}$, $r^{21}$ and $r^{22}$ each represent an integer of 0 to 5. $r^{19}$ and $r^{20}$ each represent an integer of 0 to 4.

When $r^{17}$ to $r^{22}$ are 0, it means that $R^{17}$ to $R^{22}$ are not present on the aromatic ring, that is, that the aromatic ring is not substituted by the groups represented by $R^{17}$ to $R^{22}$.

When $r^{17}$, $r^{18}$, $r^{21}$, and $r^{22}$ each are an integer of 2 to 5, or $r^{19}$ and $r^{20}$ each are an integer of 2 to 4, it means that a plurality of $R^{18}$ to $R^{22}$ is bonded to the same aromatic ring (benzene ring). When the plurality of $R^{18}$ to $R^{22}$ is bonded the same aromatic ring, the plurality of bonded groups may be present independently from each other, or may be bonded to each other via a single bond, a substituted or unsubstituted methylene group, an oxygen atom, or a sulfur atom to form a ring. For example, a plurality of substituents may be bonded to each other to form a naphthalene ring, as in the below-described Exemplary Compound 5-13.

Further, substituents $R^{17}$ to $R^{22}$ bonded to the aromatic ring each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group. The alkyl group having 1 to 6 carbon atoms, the alkenyl group having 2 to 6 carbon atoms, and the alkyloxy group having 1 to 6 carbon atoms may be straight-chain or branched.

The alkyl group having 1 to 6 carbon atoms, the cycloalkyl group having 5 to 10 carbon atoms, or the alkenyl group having 2 to 6 carbon atoms represented by $R^{17}$ to $R^{22}$ can be exemplified by the same ones as those illustrated in relation to the alkyl group having 1 to 6 carbon atoms, the cycloalkyl group having 5 to 10 carbon atoms, or the alkenyl group having 2 to 6 carbon atoms represented by $R^5$ to $R^{16}$ in the general formula (4). Modes which the groups can adopt are also the same.

The alkyloxy group having 1 to 6 carbon atoms or the cycloalkyloxy group having 5 to 10 carbon atoms represented by $R^{17}$ to $R^{22}$ can be exemplified by the same ones as those illustrated in relation to the alkyloxy group having 1 to 6 carbon atoms or the cycloalkyloxy group having 5 to 10 carbon atoms represented by $R^5$ to $R^{16}$ in the general formula (4). Modes which the groups can adopt are also the same.

The aromatic hydrocarbon group, aromatic heterocyclic group, or condensed polycyclic aromatic group represented by $R^{17}$ to $R^{22}$ can be exemplified by the same ones as those illustrated in relation to the aromatic hydrocarbon group, aromatic heterocyclic group, or condensed polycyclic aromatic group represented by $Ar^1$ to $Ar^4$ in the general formula (1).

The aryloxy groups represented by $R^{17}$ to $R^{22}$ can be exemplified by the same ones as those illustrated in relation to the aryloxy group represented by $R^5$ to $R^{16}$ in the general formula (4). Modes which the groups can adopt are also the same.

The alkyl group having 1 to 6 carbon atoms, cycloalkyl group having 5 to 10 carbon atoms, alkenyl group having 2 to 6 carbon atoms, alkyloxy group having 1 to 6 carbon atoms, cycloalkyloxy group having 5 to 10 carbon atoms, aromatic hydrocarbon group, aromatic heterocyclic group, condensed polycyclic aromatic group, or aryloxy group represented by $R^{17}$ to $R^{22}$ may have a substituent. The substituents can be exemplified by the same ones as those illustrated as the substituents optionally possessed by the aromatic hydrocarbon group, aromatic heterocyclic group, or condensed polycyclic aromatic group represented by $Ar^1$ to $Ar^4$ in the general formula (1). Modes which the substituents can adopt are also the same.

In the general formula (5), $L^4$ is a bridging group that bonds two triarylamine structures and represents a single bond or a divalent group represented by any one of the structural formulas (C) to (G).

Specific examples of preferred compounds among the triarylamine compounds represented by the general formula (5) are shown in FIGS. 90 to 96, but the triarylamine compounds represented by the general formula (5) are not limited to these compounds. D in the structural formula represents deuterium.

Figure 97:
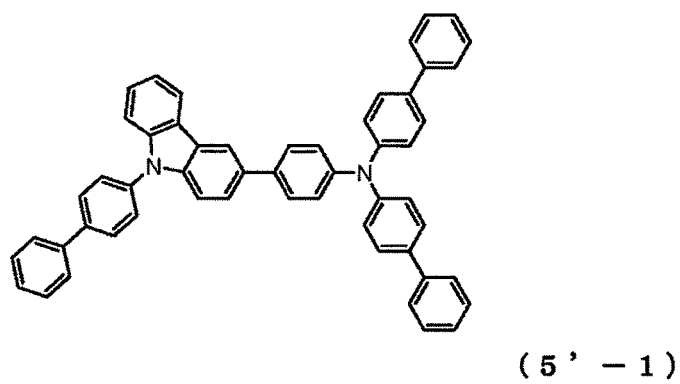
FIG. 97 is a view showing the structural formulas of Compounds (5'-1) and (5'-2) in the triarylamine compounds other than that of the general formula (5).
Figure 97:
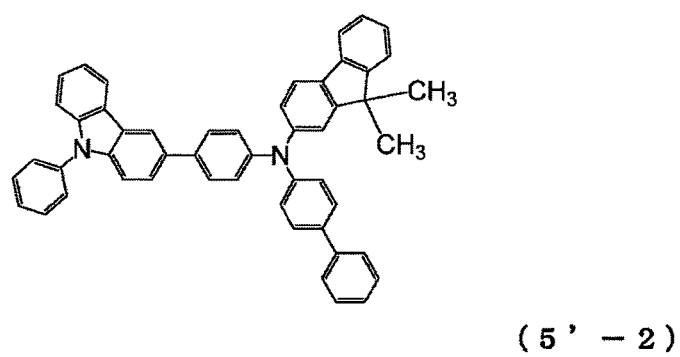

Specific examples of preferred compounds, other than the triarylamine compounds represented by the general formula (5), among the triarylamine compounds having 2 triarylamine structures are shown in FIG. 97, but the triarylamine compounds having 2 triarylamine structures are not limited to these compounds.

In the present invention, the triarylamine compounds having 3 to 6 triarylamine structures and the triarylamine compounds having 2 triarylamine structures can be synthesized by publicly known methods (see PTL 1, 8, and 9).

The produced compound is purified by column chromatography purification, adsorption purification with silica gel, activated carbon, activated clay, and the like, or recrystallization or crystallization with a solvent, and finally purified by sublimation purification, or the like, in the same manner as in the case of the arylamine compound represented by the general formula (1).

(Second Hole Transport Layer)

As described hereinabove, in the present invention, the second hole transport layer 5 on the side of the luminous layer 6 is formed using the arylamine compound represented by the general formula (1). Since the arylamine compound represented by the general formula (1) demonstrates a high electron blocking property in addition to the hole transport property, the second hole transport layer 5 excels in both the hole transport property and the electron blocking property.

Therefore, by arranging the second hole transport layer 5 adjacently to the luminous layer 6, as shown in FIG. 1, it is possible to maintain a higher carrier balance in the luminous layer 6 which is very effective for improving the characteristics of the organic EL device.

These materials may be used individually to form a film, or may be used in a mixture with other materials to form a film. The second hole transport layer 5 may be a monolayer or may have a laminated structure which includes layers each formed from a single material, which includes layers each formed from a mixture or materials, or which includes layers each formed from a single material and layers each formed from a mixture of materials.

<Luminous Layer>

The luminous layer 6 is formed on the second hole transport layer 5. Publicly known luminous materials exemplified by metal complexes of a quinolinol derivative such as $Alq_3$; various metal complexes; anthracene derivatives; bis-styrylbenzene derivatives; pyrene derivatives; oxazole derivatives; and polyparaphenylene vinylene derivatives can be used for the luminous layer 6.

Further, the luminous layer 6 may be composed of a host material and a dopant material. Anthracene derivatives are preferably used as the host material, but the aforementioned luminous materials, heterocyclic compounds having an indole ring as a partial structure of a condensed ring, heterocyclic compounds having a carbazole ring as a partial structure of a condensed ring, carbazole derivatives, thiazole derivatives, benzimidazole derivatives, and polydialkylfluorene derivatives can be also used. It is preferred that blue luminous dopants such as pyrene derivatives; and amine derivatives having a fluorene ring as a partial structure of a condensed ring be used as the dopant material, but quinacridone, coumarin, rubrene, perylene, and derivatives thereof; benzopyran derivatives; indenophenanthrene derivatives; rhodamine derivatives; and aminostyryl derivatives can be also used.

These materials may be used individually to form a film, or may be used in a mixture with other materials to form a film. The luminous layer 6 may be a monolayer or may have a laminated structure which includes layers each formed from a single material, which includes layers each formed from a mixture or materials, or which includes layers each formed from a single material and layers each formed from a mixture of materials.

A phosphorescent luminous body can be also used as the luminous material. A phosphorescent luminous body of a metal complex including iridium, platinum, or the like can be used as the phosphorescent luminous body. For example, green phosphorescent luminous bodies such as $Ir(ppy)_3$; blue phosphorescent luminous bodies such as Flrpic and $Flr^6$; and red phosphorescent luminous bodies such as $Btp_2Ir$ (acac) can be used.

In this case, a carbazole derivative such as 4,4'-di(N-carbazolyl)biphenyl (CBP), TCTA, and mCP can be used as a hole injecting/transporting host material. As an electron transporting host material, p-bis(triphenylsilyl)benzene (UGH2); and 2,2'2''-(1,3,5-phenylene)-tris(1-phenyl-1H-benzimidazole) (TPBI) can be used. By using such host material, a high-performance organic EL device can be produced.

The host material is preferably doped with the phosphorescent luminous material in an amount in a range of 1 to 30% by weight relative to the whole luminous layer by co-deposition to avoid concentration quenching.

A material which emits delayed fluorescence, such as a CDCB derivative, for example, PIC-TRZ, CC2TA, PXZ-TRZ, and 4CzIPN, can be used as the luminous material.

<Electron Transport Layer>

The electron transport layer 7 is formed on the luminous layer 6. The electron transport layer 7 is formed using the pyrimidine derivative represented by the general formula (2).

In addition to the pyrimidine derivative, metal complexes of quinolinol derivatives such as $Alq_3$ and BAlq; various metal complexes; triazole derivatives; triazine derivatives; oxadiazole derivatives; pyridine derivatives; pyrimidine derivatives; benzimidazole derivatives; thiadiazole derivatives; anthracene derivatives; carbodiimido derivatives; quinoxaline derivatives; pyridoindole derivatives; phenanthroline derivatives; and silole derivatives can be also used for the electron transport layer 7.

These materials may be used individually to form a film, or may be used in a mixture with other materials to form a film. The electron transport layer 7 may be a monolayer or may have a laminated structure which includes layers each formed from a single material, which includes layers each formed from a mixture or materials, or which includes layers each formed from a single material and layers each formed from a mixture of materials.

<Cathode>

An electrode material with a low work function, such as aluminum, or an alloy with a lower work function, such as a magnesium-silver alloy, a magnesium-indium alloy, and an aluminum-magnesium alloy, is used as the cathode 9 in the organic EL device of the present invention.

<Other Layers>

(Electron Blocking Layer)

The organic EL device of the present invention may have an electron blocking layer between the second hole transport layer 5 and the luminous layer 6. The following compounds demonstrating the electron blocking action can be used for the electron blocking layer:

arylamine compounds represented by the general formula (1);

triarylamine compounds represented by the general formula (4);

triarylamine compounds represented by the general formula (5);

carbazole derivatives, for example, 4,4',4"-tri(N-carbazolyl)triphenylamine (TCTA), 9,9-bis[4-(carbazol-9-yl)phenyl]fluorene, 1,3-bis(carbazol-9-yl)benzene (mCP), 2,2-bis(4-carbazol-9-ylphenyl)adamantane (Ad-Cz); and compounds having a triphenylsilyl group and a triarylamine structure, for example, 9-[4-(carbazol-9-yl)phenyl]-9-[4-(triphenylsilyl)phenyl]-9H-fluorene. These materials may be used individually to form a film, or may be used in a mixture with other materials to form a film. The electron blocking layer may be a monolayer or may have a laminated structure which includes layers each formed from a single material, which includes layers each formed from a mixture or materials, or which includes layers each formed from a single material and layers each formed from a mixture of materials.

(Hole Blocking Layer)

The organic EL device of the present invention may have a hole blocking layer between the luminous layer 6 and the electron transport layer 7. In addition to phenanthroline derivatives such as bathocuproine (BCP), and metal complexes of quinolinol derivatives such as aluminum(III) bis (2-methyl-8-quinolinato)-4-phenylphenolate (BAlq), compounds demonstrating the hole blocking action, such as various rare earth complexes, triazole derivatives, triazine derivatives, and oxadiazole derivatives, can be used for the hole blocking layer. These materials may also serve as materials for the electron transport layer. These materials may be used individually to form a film, or may be used in a mixture with other materials to form a film. The hole blocking layer may be a monolayer or may have a laminated structure which includes layers each formed from a single material, which includes layers each formed from a mixture or materials, or which includes layers each formed from a single material and layers each formed from a mixture of materials.

(Electron Injection Layer)

The organic EL device of the present invention may have the electron injection layer 8 between the electron transport layer 7 and the cathode 9. The following materials can be used for the electron injection layer: an alkali metal salt such as lithium fluoride and cesium fluoride; an alkaline earth metal salt such as magnesium fluoride; and a metal oxide such as aluminum oxide. However, when the preferred electron transport layer and cathode are selected, this layer can be omitted.

The present invention will be described more concretely by way of Examples, but the present invention is in no way limited to the following Examples.

Synthesis Example 1: Compound 1-1

Synthesis of 4,4'''-bis{(biphenyl-4-yl)-phenylamino}-(1,1':4',1":4",1'''-quaterphenyl)

| | |
|---|---|
| a nitrogen-purged reaction vessel was charged with N-phenyl-N-{4-(4,4,5,5-tetramethyl-1,3,2-dioxaborolan-2-yl)phenyl}-(1,1'-biphenyl-4-yl)amine | 18.2 g, |
| 4,4'-diiodobiphenyl | 7.5 g, |
| 2M aqueous solution of potassium carbonate | 46 mL, |
| toluene | 60 mL, |
| and | |
| ethanol | 15 mL, | and a nitrogen gas was passed therethrough for 1 h. Then, 1.1 g of tetrakis(triphenylphosphine)palladium was added, followed by heating, and stirring was performed for 10 h at 72° C. A total of 60 mL of methanol was added after cooling to room temperature. The precipitated solids were collected by filtration and washed with 100 mL of a mixed solution of methanol/water (5/1, v/v). Then, 100 mL of 1,2-dichlorobenzene was added and dissolution was performed under heating. The removal of insolubles by filtration was followed by gradual cooling and addition of 200 mL of methanol. The precipitated crude product was collected by filtration. The crude product was reflux washed using 100 mL of methanol. As a result, 11.8 g (yield 81%) of a light yellow powder of 4,4'''-bis{(biphenyl-4-yl)-phenylamino}-(1,1':4',1":4",1'''-quaterphenyl) (Compound 1-1) was obtained.

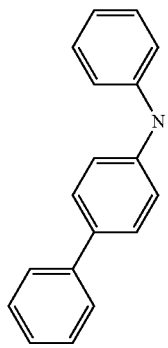
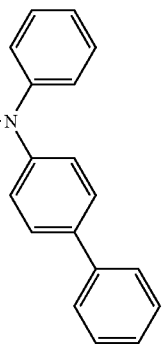

(1-1)

The structure of the resulting light yellow powder was identified using NMR. In $^1$H-NMR (CDCl$_3$), the following signals of 44 hydrogens were detected.

δ (ppm)=7.66-7.77 (8H)
7.50-7.64 (12H)
7.42-7.50 (4H)
7.28-7.38 (6H)
7.20-7.26 (12H)
7.08 (2H)

Synthesis Example 2: Compound 1-13

Synthesis of 4,4''''-bis{(biphenyl-4-yl)-phenylamino}-(1,1':4',1'':4'',1''':4''',1''''-kinkphenyl)

| | |
|---|---|
| a nitrogen-purged reaction vessel was charged with N-phenyl-N-{4-(4,4,5,5-tetramethyl-1,3,2-dioxaborolan-2-yl)phenyl}-(1,1'-biphenyl-4-yl)amine | 16.3 g, |
| 4,4'-diiodoterphenyl | 8.0 g, |
| 2M aqueous solution of potassium carbonate | 41 mL, |
| toluene | 64 mL, |
| and | |
| ethanol | 16 mL, | and a nitrogen gas was passed therethrough for 1 h. Then, 1.0 g of tetrakis(triphenylphosphine)palladium was added, followed by heating, and stirring was performed for 18 h at 72° C. A total of 60 mL of methanol was added after cooling to room temperature. The precipitated solids were collected by filtration and washed with 100 mL of a mixed solution of methanol/water (5/1, v/v). Then, 100 mL of 1,2-dichlorobenzene was added and dissolution was performed under heating. The removal of insolubles by filtration was followed by gradual cooling and addition of 200 mL of methanol. The precipitated crude product was collected by filtration. The crude product was reflux washed using 100 mL of methanol. As a result, 9.8 g (yield 66%) of a light yellow powder of 4,4''''-bis{(biphenyl-4-yl)-phenylamino}-(1,1':4',1'':4'',1''':4''',1''''-kinkphenyl) (Compound 1-13) was obtained.

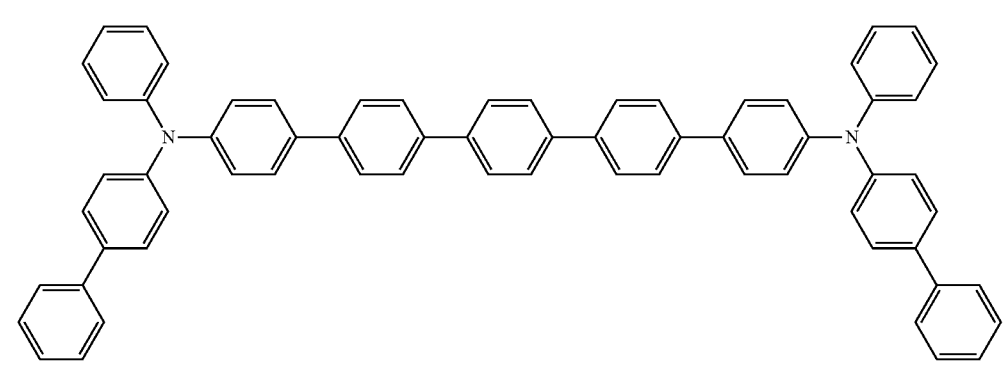

(1-13)

The structure of the resulting light yellow powder was identified using NMR. In $^1$H-NMR (CDCl$_3$), the following signals of 48 hydrogens were detected.

δ (ppm)=7.66-7.80 (12H)
7.50-7.64 (12H)
7.42-7.50 (4H)
7.28-7.38 (6H)
7.20-7.26 (12H)
7.08 (2H)

Synthesis Example 3: Compound 1-11

Synthesis of 4,4'''-bis{(biphenyl-4-yl)-phenylamino}-(1,1':3',1'':3'',1'''-quaterphenyl)

the reaction was performed under the same conditions as in Synthesis Example 1, except that
3,3'-dibromobiphenyl
was used instead of
4,4'-diiodobiphenyl.
As a result, 16.2 g (yield 91%) of a light yellow powder of 4,4'''-bis{(biphenyl-4-yl)-phenylamino}-(1,1':3',1'':3'',1'''-quaterphenyl) (Compound 1-11) was obtained.

(1-11)

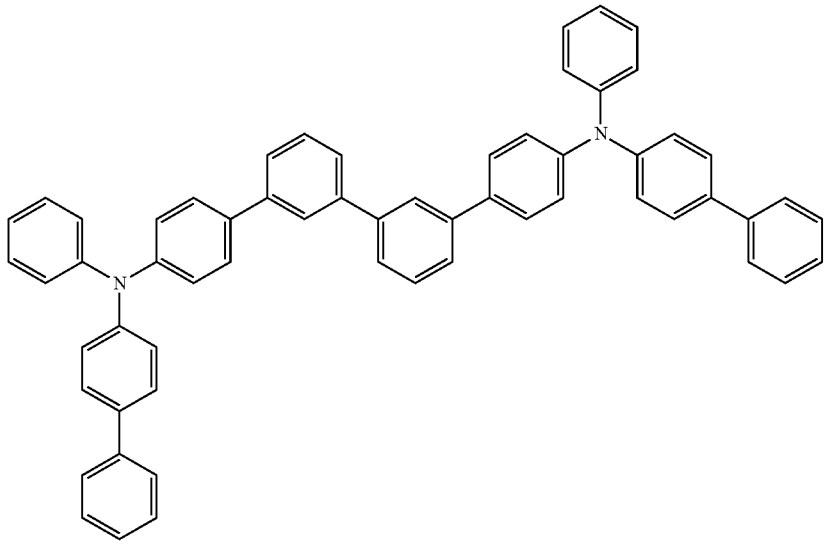

The structure of the resulting light yellow powder was identified using NMR. In ¹H-NMR (CDCl₃), the following signals of 44 hydrogens were detected.

δ (ppm)=7.87 (2H)
7.48-7.66 (18H)
7.39-7.48 (4H)
7.29-7.39 (6H)
7.18-7.26 (12H)
7.08 (2H)

Synthesis Example 4: Compound 1-15

Synthesis of 4,4''''-bis{(biphenyl-4-yl)-phenylamino}-(1,1':3',1'':2'',1''':3''',1''''-kinkphenyl)

the reaction was performed under the same conditions as in Synthesis Example 1, except that
3,3''-dibromo(1,1':2',1''-terphenyl)
was used instead of
4,4'-diiodobiphenyl.
As a result, 17.0 g (yield 92%) of a light yellow powder of 4,4''''-bis{(biphenyl-4-yl)-phenylamino}-(1,1':3',1'':2'',1''':3''',1''''-kinkphenyl) (Compound 1-15) was obtained.

The structure of the resulting light yellow powder was identified using NMR. In ¹H-NMR (CDCl₃), the following signals of 48 hydrogens were detected.

δ (ppm)=7.00-7.62 (48H)

Synthesis Example 5: Compound 1-17

Synthesis of 4,4''''-bis{(biphenyl-4-yl)-phenylamino}-(1,1':3',1'':3'',1''':3''',1''''-kinkphenyl)

the reaction was performed under the same conditions as in Synthesis Example 1, except that
3,3''-dibromo(1,1':3',1''-terphenyl)
was used instead of
4,4'-diiodobiphenyl.
As a result, 10.5 g (yield 57%) of a light yellow powder of 4,4''''-bis{(biphenyl-4-yl)-phenylamino}-(1,1':3',1'':3'',1''':3''',1''''-kinkphenyl) (Compound 1-17) was obtained.

(1-15)

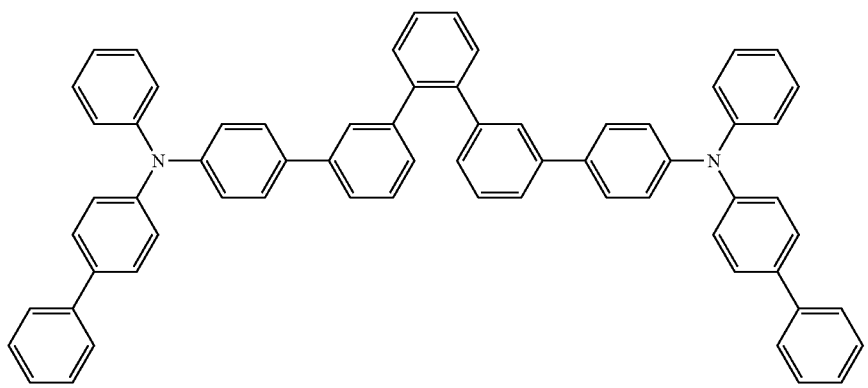

(1-17)

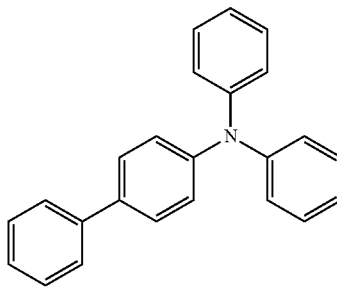  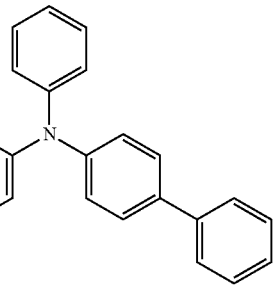

The structure of the resulting light yellow powder was identified using NMR. In ¹H-NMR (CDCl₃), the following signals of 48 hydrogens were detected.

δ (ppm)=7.93 (1H)
7.87 (2H)
7.40-7.72 (24H)
7.16-7.38 (18H)
7.09 (3H)

Synthesis Example 6: Compound 1-21

Synthesis of 4,4'''-bis{(biphenyl-4-yl)-phenylamino}-(1,1':2',1'':2'',1'''-quaterphenyl)

the reaction was performed under the same conditions as in Synthesis Example 1, except that
2,2'-dibromobiphenyl
was used instead of
4,4'-diiodobiphenyl.
As a result, 9.0 g (yield 83%) of a light yellow powder of 4,4''''-bis{(biphenyl-4-yl)-phenylamino}-(1,1':2',1'':2'',1'''-quaterphenyl) (Compound 1-21) was obtained.

(1-21)

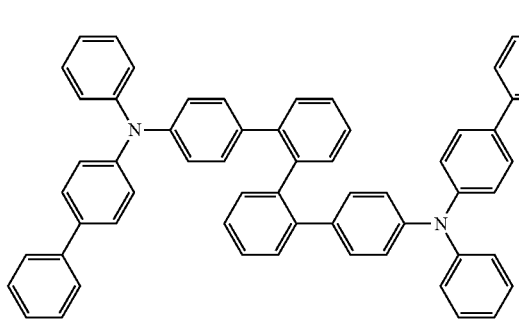

The structure of the resulting light yellow powder was identified using NMR. In ¹H-NMR (CDCl₃), the following signals of 44 hydrogens were detected.

δ (ppm)=7.45-7.54 (6H)
7.23-7.45 (16H)
7.13-7.22 (4H)
7.05-7.13 (8H)
6.94 (2H)
6.82 (4H)
6.62 (4H)

Synthesis Example 7: Compound 1-22

Synthesis of 4,4'''-bis{(naphthalen-1-yl)-phenylamino}-(1,1':3',1'':3'',1'''-quaterphenyl)

the reaction was performed under the same conditions as in Synthesis Example 1, except that
3,3'-dibromobiphenyl
was used instead of
4,4'-diiodobiphenyl,
and
N-phenyl-N-{4-(4,4,5,5-tetramethyl-1,3,2-dioxaborolan-2-yl)phenyl}-(naphthalen-1-yl)amine
was used instead of
N-phenyl-N-{4-(4,4,5,5-tetramethyl-1,3,2-dioxaborolan-2-yl)phenyl}-(1,1'-biphenyl-4-yl)amine.
As a result, 4.00 g (yield 26%) of a light yellow powder of 4,4'''-bis{(naphthalen-1-yl)-phenylamino}-(1,1':3',1'':3'',1'''-quaterphenyl) (Compound 1-22) was obtained.

(1-22)

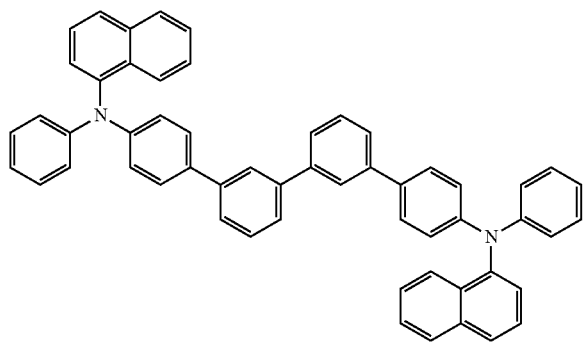

The structure of the resulting light yellow powder was identified using NMR. In ¹H-NMR (CDCl₃), the following signals of 40 hydrogens were detected.

δ (ppm)=7.99 (2H)
7.92 (2H)
7.78-7.85 (4H)
7.35-7.61 (18H)
7.19-7.28 (4H)
7.06-7.15 (8H)
6.98 (2H)

Synthesis Example 8: Compound 1-23

Synthesis of 4,4''''-bis{(biphenyl-4-yl)-phenylamino}-(1,1':4',1":2",1'":4'",1''''-kinkphenyl)

the reaction was performed under the same conditions as in Synthesis Example 1, except that
4,4"-dibromo(1,1':2',1"-terphenyl)
was used instead of
4,4'-diiodobiphenyl.
As a result, 13.8 g (yield 62%) of a light yellow powder of 4,4''''-bis{(biphenyl-4-yl)-phenylamino}-(1,1':4',1":2",1'": 4'",1''''-kinkphenyl) (Compound 1-23) was obtained.

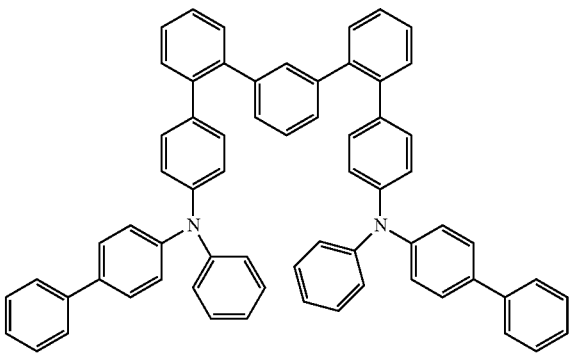

(1-24)

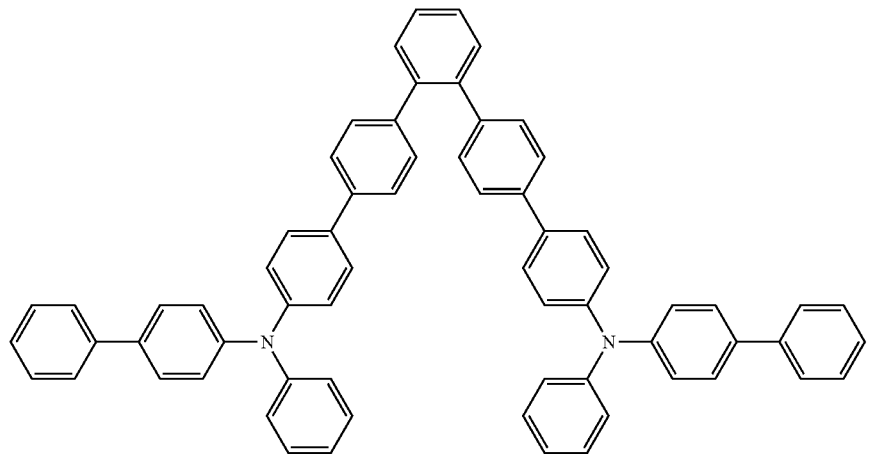

(1-23)

The structure of the resulting light yellow powder was identified using NMR. In $^1$H-NMR (CDCl$_3$), the following signals of 48 hydrogens were detected.

δ (ppm)=7.60 (4H)
7.03-7.56 (44H)

The structure of the resulting light yellow powder was identified using NMR. In $^1$H-NMR (CDCl$_3$), the following signals of 48 hydrogens were detected.

δ (ppm)=7.30-7.56 (20H)
6.91-7.24 (28H)

Synthesis Example 9: Compound 1-24

Synthesis of 4,4''''-bis{(biphenyl-4-yl)-phenylamino}-(1,1':2',1":3",1'":2'",1''''-kinkphenyl)

the reaction was performed under the same conditions as in Synthesis Example 1, except that
2,2"-dibromo(1,1':3',1"-terphenyl)
was used instead of
4,4'-diiodobiphenyl.
As a result, 9.7 g (yield 69%) of a light yellow powder of 4,4''''-bis{(biphenyl-4-yl)-phenylamino}-(1,1':2',1":3",1'": 2'",1''''-kinkphenyl) (Compound 1-24) was obtained.

Synthesis Example 10: Compound 1-25

Synthesis of 4,4''''-bis{(biphenyl-4-yl)-phenylamino}-(1,1':4',1":3",1'":4'",1''''-kinkphenyl)

the reaction was performed under the same conditions as in Synthesis Example 1, except that
4,4'-dibromo(1,1':3',1'-terphenyl)
was used instead of
4,4'-diiodobiphenyl.
As a result, 16.5 g (yield 74%) of a light yellow powder of 4,4''''-bis{(biphenyl-4-yl)-phenylamino}-(1,1':4',1":3",1'": 4'",1''''-kinkphenyl) (Compound 1-25) was obtained.

(1-25)

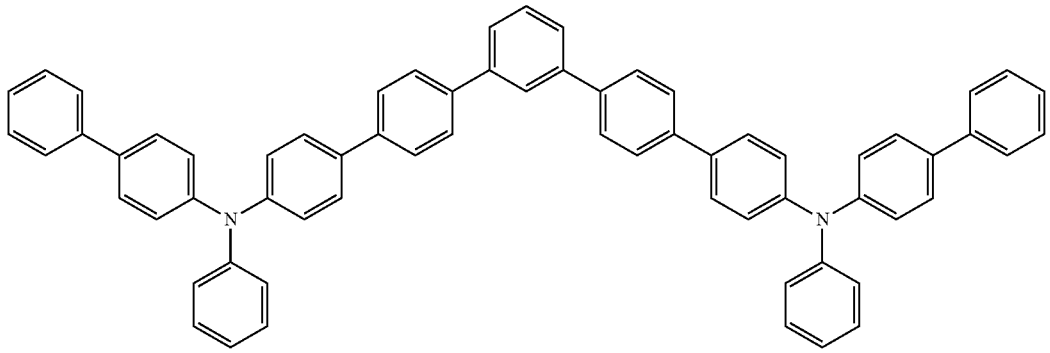

The structure of the resulting light yellow powder was identified using NMR. In ¹H-NMR (CDCl₃), the following signals of 48 hydrogens were detected.
δ (ppm)=7.93 (1H)
7.06-7.80 (47H)

Synthesis Example 11: Compound 1-26

Synthesis of 4,4''''-bis{(dibenzofuran-1-yl)-phenylamino}-(1,1':4',1'':2'',1''':4''',1''''-kinkphenyl)

the reaction was performed under the same conditions as in Synthesis Example 8, except that
N-phenyl-N-{4-(4,4,5,5-tetramethyl-1,3,2-dioxaborolan-2-yl)phenyl}-(dibenzofuran-1-yl)amine
was used instead of
N-phenyl-N-{4-(4,4,5,5-tetramethyl-1,3,2-dioxaborolan-2-yl)phenyl}-(1,1'-biphenyl-4-yl)amine.
As a result, 14.0 g (yield 61%) of a light yellow powder of 4,4''''-bis{(dibenzofuran-1-yl)-phenylamino}-(1,1':4',1'':2'', 1''':4''',1''''-kinkphenyl) (Compound 1-26) was obtained.

(1-26)

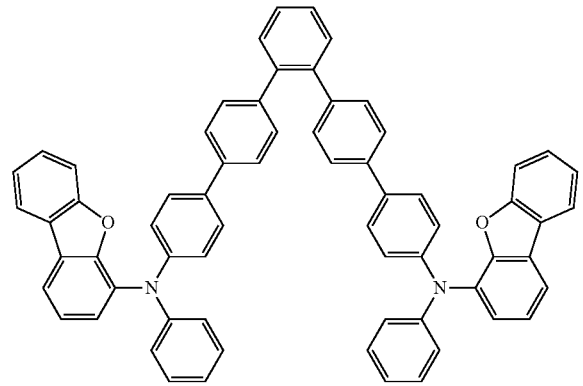

The structure of the resulting light yellow powder was identified using NMR. In ¹H-NMR (CDCl₃), the following signals of 44 hydrogens were detected.
δ (ppm)=7.97 (2H)
7.79 (2H)
7.02-7.55 (40H)

Synthesis Example 12: Compound 1-27

Synthesis of 4,4''''-bis{(biphenyl-4-yl)-phenylamino}-(1,1':2',1'':2'',1''':2''',1''''-kinkphenyl)

the reaction was performed under the same conditions as in Synthesis Example 1, except that 2,2'-dibromo(1,1':2',1''-terphenyl)

was used instead of
4,4'-diiodobiphenyl.

As a result, 8.5 g (yield 61%) of a light yellow powder of 4,4''''-bis{(biphenyl-4-yl)-phenylamino}-(1,1':2',1'':2'',1''': 2''',1''''-kinkphenyl) (Compound 1-27) was obtained.

(1-27)

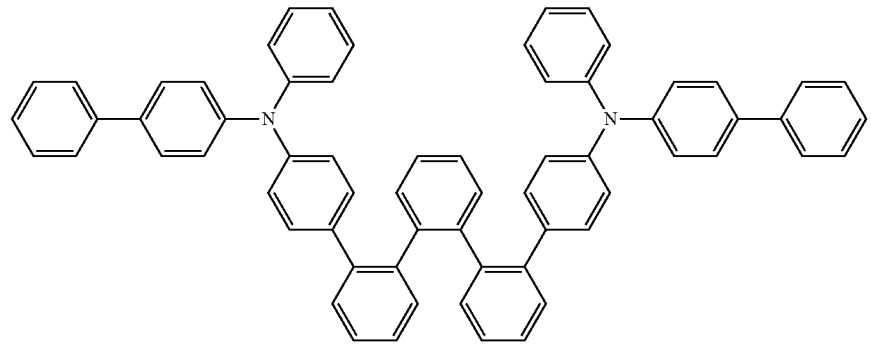

The structure of the resulting light yellow powder was identified using NMR. In $^1$H-NMR (CDCl$_3$), the following signals of 48 hydrogens were detected.
δ (ppm)=7.62 (4H)
6.78-7.57 (36H)
6.53 (4H)
6.46 (2H)
6.38 (2H)

Synthesis Example 13: Compound 1-28

Synthesis of 4,4'''-bis{(biphenyl-4-yl)-d5-phenylamino}-(1,1':3',1":3",1'''-quaterphenyl)

the reaction was performed under the same conditions as in Synthesis Example 1, except that
3,3'-dibromobiphenyl
was used instead of
4,4'-diiodobiphenyl,
and
N-(phenyl-d$_5$)-N-{4-(4,4,5,5-tetramethyl-1,3,2-dioxaborolan-2-yl)phenyl}-(1,1'-biphenyl-4-yl)amine
was used instead of
N-phenyl-N-{4-(4,4,5,5-tetramethyl-1,3,2-dioxaborolan-2-yl)phenyl}-(1,1'-biphenyl-4-yl)amine.
As a result, 8.7 g (yield 68%) of a light yellow powder of 4,4'''-bis{(biphenyl-4-yl)-d5-phenylamino}-(1,1':3',1":3",1'''-quaterphenyl) (Compound 1-28) was obtained.

δ (ppm)=7.87 (2H)
7.40-7.66 (20H)
7.30-7.38 (4H)
7.19-7.26 (8H)

Synthesis Example 14: Compound 1-38

Synthesis of 4,4'''-bis{(biphenyl-4-yl)-phenylamino}-(1,1':3',1":4",1'''-quaterphenyl)

the reaction was performed under the same conditions as in Synthesis Example 1, except that 3,4'-dibromobiphenyl was used instead of 4,4'-diiodobiphenyl.

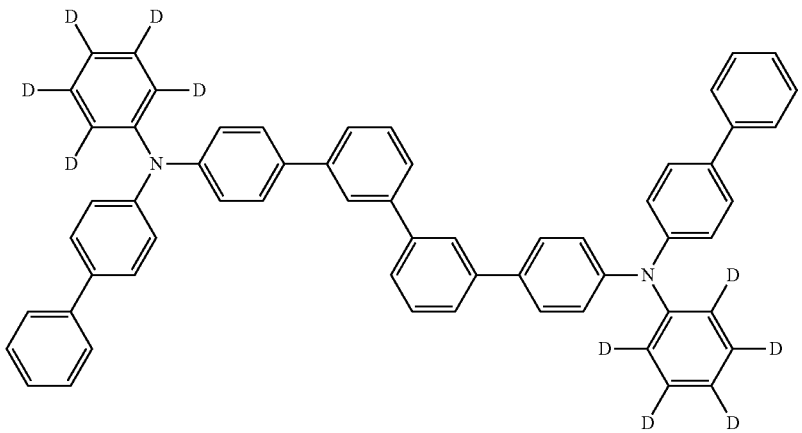

(1-28)

The structure of the resulting light yellow powder was identified using NMR. In $^1$H-NMR (CDCl$_3$), the following signals of 34 hydrogens were detected.

As a result, 14.0 g (yield 84%) of a light yellow powder of 4,4'''-bis{(biphenyl-4-yl)-phenylamino}-(1,1':3',1":4",1'''-quaterphenyl) (Compound 1-38) was obtained.

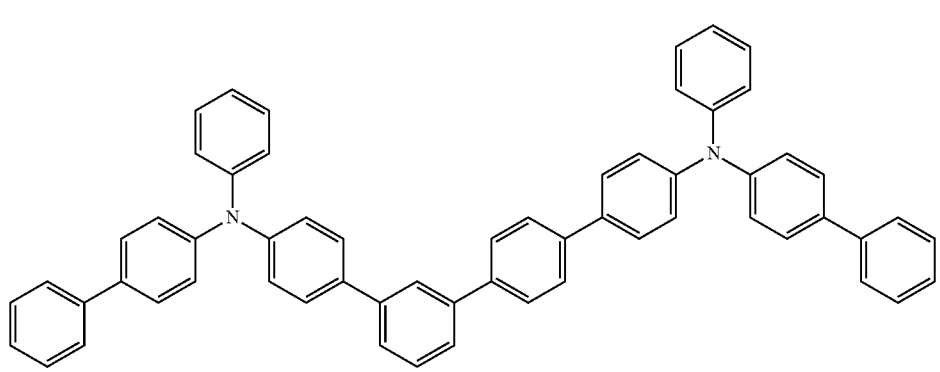

(1-38)

The structure of the resulting light yellow powder was identified using NMR. In $^1$H-NMR (CDCl$_3$), the following signals of 44 hydrogens were detected.

δ (ppm)=7.00-8.00 (44H)

<Measurement of Glass Transition Temperature>

The glass transition temperature of the arylamine compound represented by the general formula (1) was determined with a high-sensitivity differential scanning calorimeter (DSC3100S, manufactured by Bruker AXS K.K.).

|  | Glass transition temperature |
| --- | --- |
| Synthesis Example 1 (Compound 1-1) | 119° C. |
| Synthesis Example 2 (Compound 1-13) | 124° C. |
| Synthesis Example 3 (Compound 1-11) | 114° C. |
| Synthesis Example 4 (Compound 1-15) | 115° C. |
| Synthesis Example 5 (Compound 1-17) | 118° C. |
| Synthesis Example 6 (Compound 1-21) | 111° C. |
| Synthesis Example 7 (Compound 1-22) | 112° C. |
| Synthesis Example 8 (Compound 1-23) | 129° C. |
| Synthesis Example 9 (Compound 1-24) | 113° C. |
| Synthesis Example 10 (Compound 1-25) | 126° C. |
| Synthesis Example 11 (Compound 1-26) | 131° C. |
| Synthesis Example 12 (Compound 1-27) | 121° C. |
| Synthesis Example 13 (Compound 1-28) | 113° C. |
| Synthesis Example 14 (Compound 1-38) | 117° C. |

The arylamine compound represented by the general formula (1) had a glass transition temperature of 100° C. or higher, which indicates a stable thin-film state.

<Measurement of Work Function>

A vapor-deposited film with a thickness of 100 nm was produced on an ITO substrate by using the arylamine compound represented by the general formula (1), and the work function was measured with an ionization potential measuring device (PYS-202, manufactured by Sumitomo Heavy Industries, Ltd.).

|  | Work function |
| --- | --- |
| Synthesis Example 1 (Compound 1-1) | 5.68 eV |
| Synthesis Example 2 (Compound 1-13) | 5.69 eV |
| Synthesis Example 3 (Compound 1-11) | 5.73 eV |
| Synthesis Example 4 (Compound 1-15) | 5.74 eV |
| Synthesis Example 5 (Compound 1-17) | 5.77 eV |
| Synthesis Example 6 (Compound 1-21) | 5.73 eV |
| Synthesis Example 7 (Compound 1-22) | 5.81 eV |
| Synthesis Example 8 (Compound 1-23) | 5.71 eV |
| Synthesis Example 9 (Compound 1-24) | 5.74 eV |
| Synthesis Example 10 (Compound 1-25) | 5.72 eV |
| Synthesis Example 11 (Compound 1-26) | 5.74 eV |
| Synthesis Example 12 (Compound 1-27) | 5.73 eV |
| Synthesis Example 13 (Compound 1-28) | 5.76 eV |
| Synthesis Example 14 (Compound 1-38) | 5.74 eV |

The arylamine compound represented by the general formula (1) shows an advantageous energy level and has a satisfactory hole transport capacity when compared with the work function of 5.4 eV of the typical hole transport materials such as NPD and TPD.

Device Example 1

An organic EL device was produced by forming in advance an ITO electrode as the transparent anode 2 on the glass substrate 1, and then vapor depositing thereon the hole injection layer 3, the first hole transport layer 4, the second hole transport layer 5, the luminous layer 6, the electron transport layer 7, the electron injection layer 8, and the cathode (aluminum electrode) 9 in the order depicted in FIG. 1.

More specifically, the glass substrate 1 on which an ITO film with a thickness of 150 nm was grown was prepared. The glass substrate 1 was ultrasonically cleaned for 20 min in isopropyl alcohol and then dried for 10 min on a hot plate heated to 200° C. Then, UV/ozone treatment was performed for 15 min, the ITO-attached glass substrate was attached inside a vacuum vapor deposition device, and pressure was reduced to 0.001 Pa or less.

Then, a Compound 6 of the structural formula indicated below was formed as the hole injection layer 3 to a film thickness of 5 nm so as to cover the transparent electrode 2.

A Compound 5-1 of the structural formula indicated below was formed as the first hole transport layer 4 to a film thickness of 60 nm on the hole injection layer 3.

The Compound 1-11 of Synthesis Example 3 was formed as the second hole transport layer 5 to a film thickness of 5 nm on the first hole transport layer 4.

A Compound 7-A of the structural formula indicated below and a Compound 8-A of the structural formula indicated below were formed as the luminous layer 6 to a film thickness of 20 nm on the second hole transport layer 5 by binary vapor deposition at vapor deposition rates such that the vapor deposition rate ratio of the Compound 7-A to the Compound 8-A was 5:95.

A Compound 2-92 of the structural formula indicated below and a Compound 9 of the structural formula indicated below were formed as the electron transport layer 7 to a film thickness of 30 nm on the luminous layer 6 by binary vapor deposition at vapor deposition rates such that the vapor deposition rate ratio of the Compound 2-92 to the Compound 9 was 50:50.

Lithium fluoride was formed as the electron injection layer 8 to a film thickness of 1 nm on the electron transport layer 7.

Finally, the cathode 9 was formed by vapor depositing aluminum to 100 nm.

The fabricated organic EL device was measured for the light emission characteristics exhibited when a direct current voltage was applied at normal temperature in the atmosphere. The results are shown in Table 1.

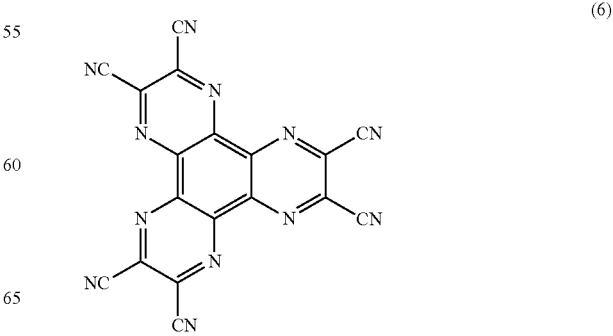

(6)

(5-1)

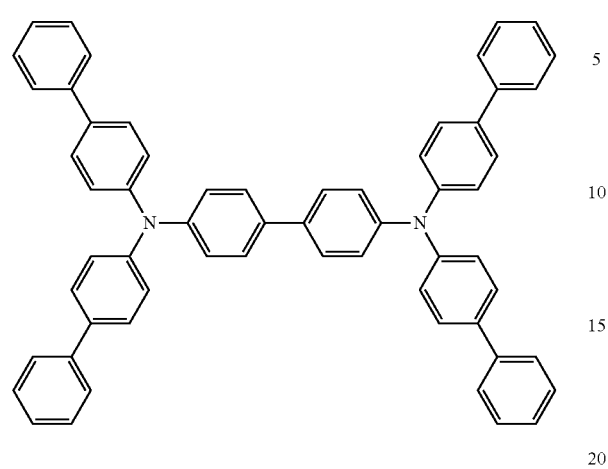

(8-A)

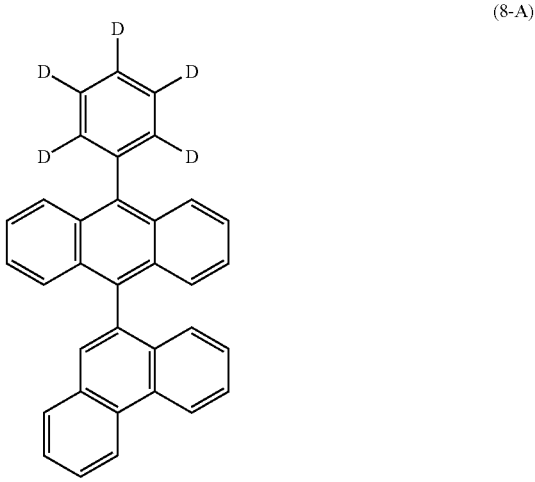

(1-11)

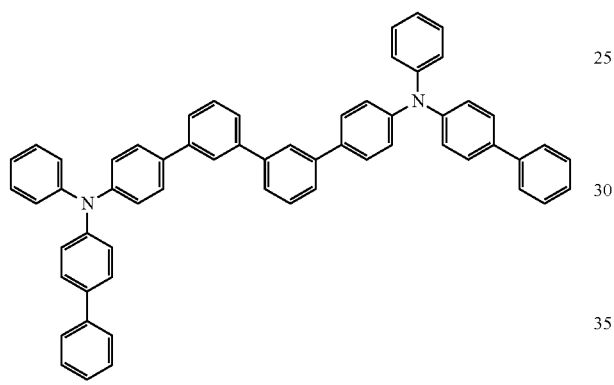

(2-92)

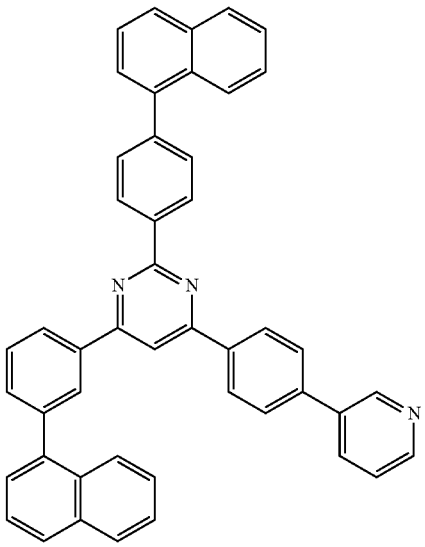

(7-A)

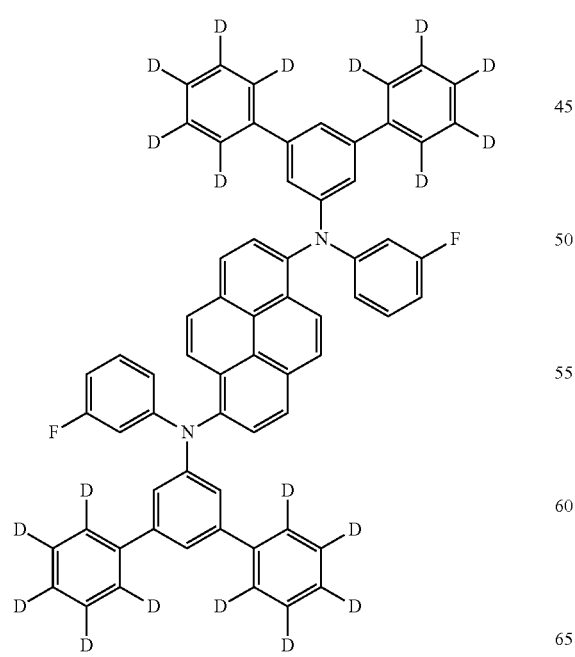

(9)

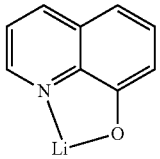

Device Example 2

An organic EL device was fabricated under the same conditions as in Device Example 1, except that the Compound 1-38 of Synthesis Example 14 was used instead of the Compound 1-11 of Synthesis Example 3 as the material of the second hole transport layer 5. The fabricated organic EL device was measured for the light emission characteristics exhibited when a direct current voltage was applied at normal temperature in the atmosphere. The results are shown in Table 1.

(1-38)

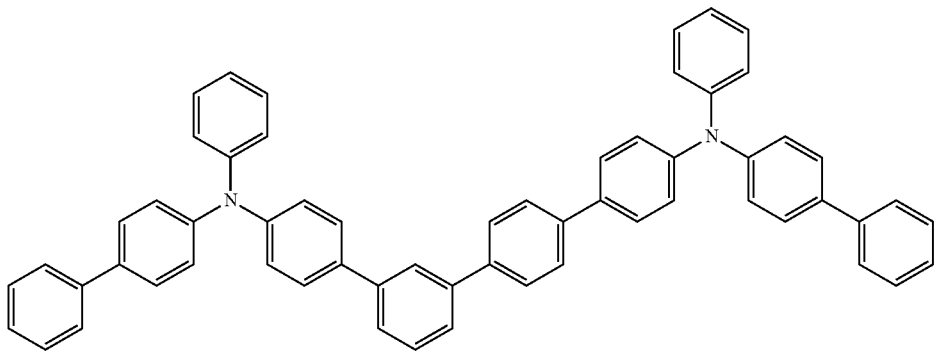

Device Example 3

An organic EL device was fabricated under the same conditions as in Device Example 1, except that a Compound 2-123 of the structural formula indicated below was used instead of the Compound 2-92 as the material of the electron transport layer 7. The fabricated organic EL device was measured for the light emission characteristics exhibited when a direct current voltage was applied at normal temperature in the atmosphere. The results are shown in Table 1.

(2-123)

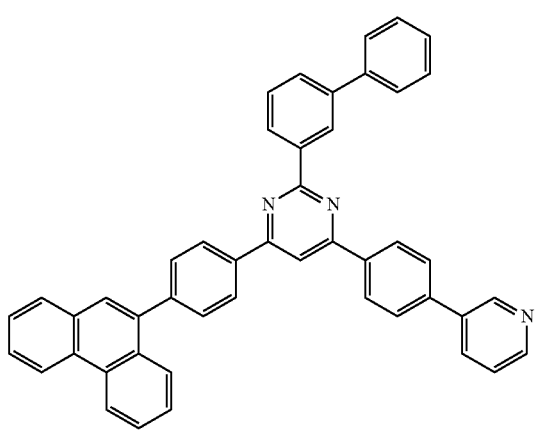

Device Example 4

An organic EL device was fabricated under the same conditions as in Device Example 3, except that the Compound 1-38 of Synthesis Example 14 was used instead of the Compound 1-11 of Synthesis Example 3 as the material of the second hole transport layer 5. The fabricated organic EL device was measured for the light emission characteristics exhibited when a direct current voltage was applied at normal temperature in the atmosphere. The results are shown in Table 1.

Device Example 5

An organic EL device was fabricated under the same conditions as in Device Example 1, except that a Compound 2-124 of the structural formula indicated below was used instead of the Compound 2-92 as the material of the electron transport layer 7. The fabricated organic EL device was measured for the light emission characteristics exhibited when a direct current voltage was applied at normal temperature in the atmosphere. The results are shown in Table 1.

(2-124)

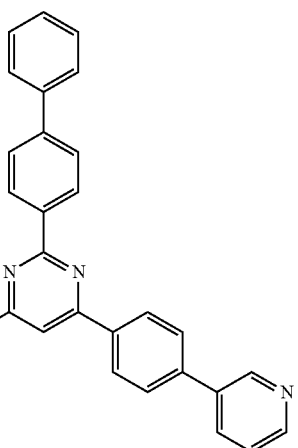

Device Example 6

An organic EL device was fabricated under the same conditions as in Device Example 5, except that the Compound 1-38 of Synthesis Example 14 was used instead of the Compound 1-11 of Synthesis Example 3 as the material of the second hole transport layer 5. The fabricated organic EL device was measured for the light emission characteristics exhibited when a direct current voltage was applied at normal temperature in the atmosphere. The results are shown in Table 1.

Comparative Device Example 1

An organic EL device was fabricated under the same conditions as in Device Example 1, except that the Compound 5-1 was used instead of the Compound 1-11 of Synthesis Example 3 as the material of the second hole transport layer 5. In this case, the first hole transport layer 4 and the second hole transport layer 5 function as an integrated hole transport layer (film thickness 65 nm). The fabricated organic EL device was measured for the light emission characteristics exhibited when a direct current voltage was applied at normal temperature in the atmosphere. The results are shown in Table 1.

Comparative Device Example 2

An organic EL device was fabricated under the same conditions as in Device Example 3, except that the Compound 5-1 was used instead of the Compound 1-11 of Synthesis Example 3 as the material of the second hole transport layer 5. In this case, the first hole transport layer 4 and the second hole transport layer 5 function as an integrated hole transport layer (film thickness 65 nm). The fabricated organic EL device was measured for the light emission characteristics exhibited when a direct current voltage was applied at normal temperature in the atmosphere. The results are shown in Table 1.

Comparative Device Example 3

An organic EL device was fabricated under the same conditions as in Device Example 5, except that the Compound 5-1 was used instead of the Compound 1-11 of Synthesis Example 3 as the material of the second hole transport layer 5. In this case, the first hole transport layer 4 and the second hole transport layer 5 function as an integrated hole transport layer (film thickness 65 nm). The fabricated organic EL device was measured for the light emission characteristics exhibited when a direct current voltage was applied at normal temperature in the atmosphere. The results are shown in Table 1.

Comparative Device Example 4

An organic EL device was fabricated under the same conditions as in Device Example 1, except that the Compound 5-1 was used instead of the Compound 1-11 of Synthesis Example 3 as the material of the second hole transport layer 5, and the compound ETM-1 (see WO 2003/060956) of the structural formula indicated below was used instead of the Compound 2-92 as the material of the electron transport layer 7. In this case, the first hole transport layer 4 and the second hole transport layer 5 function as an integrated hole transport layer (film thickness 65 nm). The fabricated organic EL device was measured for the light emission characteristics exhibited when a direct current voltage was applied at normal temperature in the atmosphere. The results are shown in Table 1.

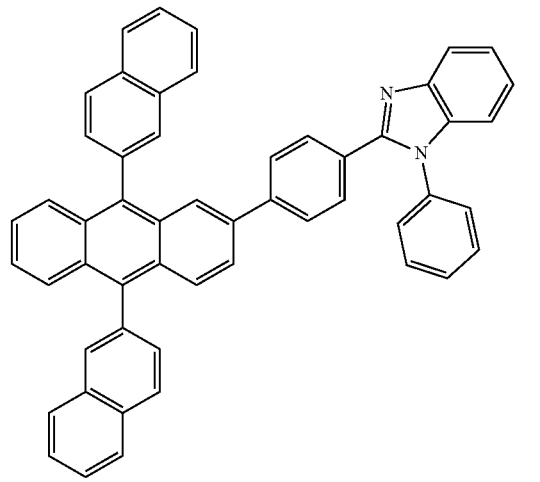

(ETM-1)

The device life was measured using the organic EL devices produced in Device Examples 1 to 6 and Comparative Device Examples 1 to 4. The results are shown in Table 1. The device life was measured as a time till the emission luminance attenuated to 1900 cd/m$^2$ (corresponds to 95% when the initial luminance is 100%; 95% attenuation) when a constant-current drive was performed at an emission luminance at the emission start time (initial luminance) of 2000 cd/m$^2$.

TABLE 1

| Organic EL device No. | First hole transport layer | Second hole transport layer | Electron transport layer | *1 [V] | *2 [cd/m$^2$] | *3 [cd/A] | *4 [lm/W] | Device life (95% attenuation) (h) |
|---|---|---|---|---|---|---|---|---|
| Ex. 1 | Cpd. 5-1 | Cpd. 1-11 | Cpd. 2-92/ Cpd. 9 | 3.86 | 848 | 8.49 | 6.94 | 161 |
| Ex. 2 | | Cpd. 1-38 | Cpd. 9 | 3.85 | 893 | 8.94 | 7.30 | 201 |
| Ex. 3 | | Cpd. 1-11 | Cpd. 2-123/ Cpd. 9 | 3.80 | 838 | 8.38 | 6.92 | 140 |
| Ex. 4 | | Cpd. 1-38 | Cpd. 9 | 3.81 | 882 | 8.82 | 7.28 | 143 |
| Ex. 5 | | Cpd. 1-11 | Cpd. 2-124/ Cpd. 9 | 3.80 | 826 | 8.26 | 6.84 | 148 |
| Ex. 6 | | Cpd. 1-38 | Cpd. 9 | 3.79 | 860 | 8.60 | 7.13 | 185 |
| Comp. Ex. 1 | Cpd. 5-1 | Cpd. 5-1 | Cpd. 2-92/ Cpd. 9 | 3.76 | 793 | 7.95 | 6.65 | 83 |
| Comp. Ex. 2 | | | Cpd. 2-123/ Cpd. 9 | 3.69 | 793 | 7.96 | 6.78 | 87 |
| Comp. Ex. 3 | | | Cpd. 2-124/ Cpd. 9 | 3.72 | 770 | 7.73 | 6.54 | 88 |
| Comp. Ex. 4 | | | ETM-1/ Cpd. 9 | 3.84 | 635 | 6.35 | 5.20 | 55 |

*1: Voltage (@10 mA/cm$^2$)

*2: Luminance (@10 mA/cm$^2$)

*3: Luminous efficiency (@10 mA/cm$^2$)

*4: Power efficiency (@10 mA/cm$^2$)

Cpd.: Compound

As indicated in Table 1, comparing Device Examples 1 and 2 and Comparative Device Example 1, which had the same electron transport material, in Device Examples 1 and 2, the luminous efficiency was 8.49 to 8.94 cd/A which was higher than 7.95 cd/A in Comparative Device Example 1. The power efficiency in Device Examples 1 and 2 was 6.94 to 7.30 lm/W which was also higher than 6.65 lm/W in Comparative Device Example 1. The device life in Device Examples 1 and 2 was 161 to 201 h which was much longer than 83 h in Comparative Device Example 1.

Comparing Device Examples 3 and 4 and Comparative Device Example 2, which had the same electron transport material, in Device Examples 3 and 4, the luminous efficiency was 8.38 to 8.82 cd/A which was higher than 7.96 cd/A in Comparative Device Example 2. The power efficiency in Device Examples 3 and 4 was 6.92 to 7.28 lm/W which was also higher than 6.78 lm/W in Comparative Device Example 2. The device life in Device Examples 3 and 4 was 140 to 143 h which was much longer than 87 h in Comparative Device Example 2.

Comparing Device Examples 5 and 6 and Comparative Device Example 3, which had the same electron transport material, in Examples 5 and 6 of the organic EL device, the luminous efficiency was 8.26 to 8.60 cd/A which was higher than 7.73 cd/A in Comparative Device Example 3. The power efficiency in Device Examples 5 and 6 was 6.84 to 7.13 lm/W which was also higher than 6.54 lm/W in Comparative Device Example 3. The device life in Device Examples 5 and 6 was 148 to 185 h which was much longer than 88 h in Comparative Device Example 3.

Comparing Device Examples 1 to 6, which used the pyrimidine derivative represented by the general formula (2) as the electron transport material, and Comparative Example 4 which used the compound ETM-1 of the structural formula indicated above as the electron transport material, this compound being the publicly known electron transport material, in Device Examples 1 to 6, the luminous efficiency was 8.26 to 8.94 cd/A which was higher than 6.35 cd/A in Comparative Example 4 of the organic EL device. The power efficiency in Examples 1 to 6 of the organic EL device was 6.84 to 7.30 lm/W which was also higher than 5.20 lm/W in Comparative Device Example 4. The device life in Device Examples 1 to 6 was 140 to 201 h which was much longer than 55 h in Comparative Device Example 4.

The present invention makes it possible to realize an organic EL device with a high luminous efficiency and long life by combining an arylamine compound having a specific structure with a pyrimidine derivative having a specific structure so that holes and electrons could be injected and transported in the luminous layer with satisfactory efficiency. Furthermore, by combining a triarylamine compound having a specific structure as the material of the first hole transport layer with the abovementioned combination, it is possible to obtain a combination of materials with further refined carrier balance and realize an organic EL device in which holes could be injected and transported in the luminous layer with more satisfactory efficiency. Thus, with the present invention, it is possible to realize an organic EL device which has a luminous efficiency higher a device life longer than those of the conventional organic EL devices.

INDUSTRIAL APPLICABILITY

The organic EL device of the present invention has increased luminous efficiency and improved durability, and therefore can be put to uses such as domestic electrical appliances and illumination.

DESCRIPTION OF REFERENCE NUMERALS

1 Glass substrate
2 Transparent anode
3 Hole injection layer
4 First hole transport layer
5 Second hole transport layer
6 Luminous layer
7 Electron transport layer
8 Electron injection layer
9 Cathode

The invention claimed is:

1. An organic electroluminescence device having at least an anode, a hole injection layer, a first hole transport layer, a second hole transport layer, a luminous layer, an electron transport layer, and a cathode in order of description, wherein
the second hole transport layer includes an arylamine compound represented by the following formula (1):

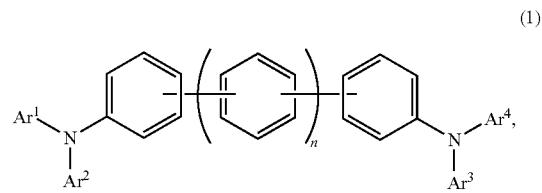

(1)

and
the electron transport layer includes a pyrimidine derivative represented by the following formula (2a):

(2a)

wherein
$Ar^1$ and $Ar^3$ each represents an aromatic hydrocarbon group, and $Ar^2$ and $Ar^4$ each represents an aromatic hydrocarbon group or an aromatic heterocyclic group; and
n represents an integer of 2 or 3,
$Ar^5$ represents an aromatic hydrocarbon group;
$Ar^6$ represents a phenyl group substituted with a condensed polycyclic aromatic group, and $Ar^7$ represents a hydrogen atom; and
A represents a monovalent group represented by the following structural formula (3b):

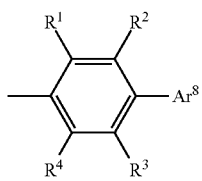

(3b)

wherein
Ar⁸ represents an aromatic heterocyclic group; and
$R^1$ to $R^4$ each represents a hydrogen atom.

2. The organic electroluminescence device according to claim 1, wherein the first hole transport layer includes a triarylamine compound having 3 to 6 triarylamine structures in a molecule, the triarylamine structures being linked to each other via a single bond or a divalent group having no heteroatom.

3. The organic electroluminescence device according to claim 2, wherein the triarylamine compound having 3 to 6 triarylamine structures is a triarylamine compound which has 4 triarylamine structures in a molecule and is represented by the following formula (4):

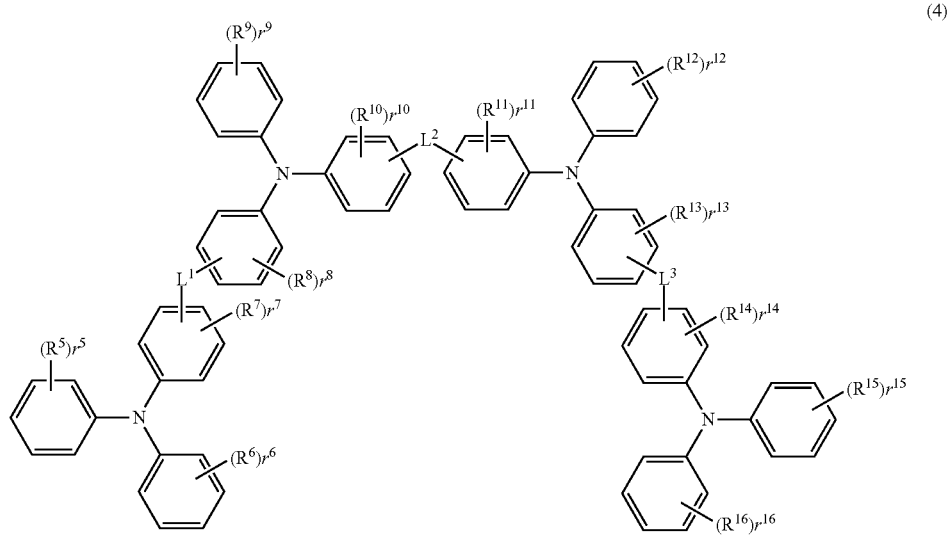

(4)

wherein
$r^5$, $r^6$, $r^9$, $r^{12}$, $r^{15}$, and $r^{16}$ each represents an integer of 0 to 5;
$r^7$, $r^8$, $r^{10}$, $r^{11}$, $r^{13}$, and $r^{14}$ each represents an integer of 0 to 4;
$R^5$ to $R^{16}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group; when a plurality of these groups is present in the same benzene ring, the plurality of groups may be bonded to each other via a single bond, a substituted or unsubstituted methylene group, an oxygen atom, or a sulfur atom to form a ring; and $L^1$ to $L^3$ each represents a single bond or a divalent group represented by any of the following structural formulas (B) to (G):

(B)

wherein n1 represents an integer of 1 to 3,

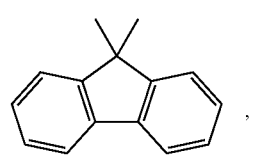

(C)

-continued

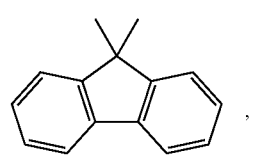

(D)

—CH₂—  , (E)

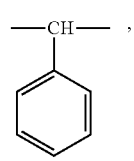

(F)

-continued

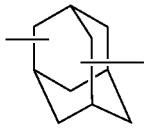
(G)

4. The organic electroluminescence device according to claim 1, wherein the first hole transport layer includes a triarylamine compound having 2 triarylamine structures in a molecule, the triarylamine structures being linked to each other via a single bond or a divalent group having no heteroatom.

5. The organic electroluminescence device according to claim 4, wherein the triarylamine compound having 2 triarylamine structures is represented by the following formula (5):

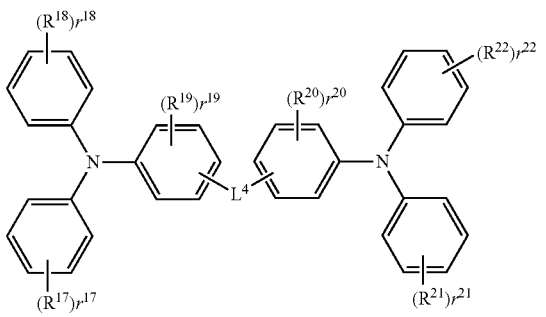
(5)

wherein
$r^{17}$, $r^{18}$, $r^{21}$, and $r^{22}$ each represents an integer of 0 to 5; $r^{19}$ and $r^{20}$ each represents an integer of 0 to 4;
$R^{17}$ to $R^{22}$ each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxy group; when a plurality of these groups is bonded to the same benzene ring, the plurality of bonded groups may be bonded to each other via a single bond, a substituted or unsubstituted methylene group, an oxygen atom, or a sulfur atom to form a ring; and $L^4$ represents a single bond or a divalent group represented by any of the following structural formulas (C) to (G):

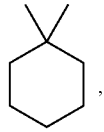
(C)

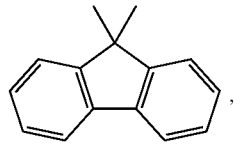
(D)

—CH$_2$—, (E)

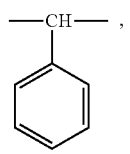
(F)

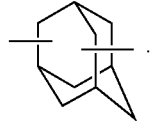
(G)

6. The organic electroluminescence device according to claim 1, wherein the luminous layer includes a blue luminous dopant.

7. The organic electroluminescence device according to claim 6, wherein the blue luminous dopant is a pyrene derivative.

8. The organic electroluminescence device according to claim 1, wherein the luminous layer includes an anthracene derivative.

9. The organic electroluminescence device according to claim 8, wherein the luminous layer includes the anthracene derivative as a host material.

* * * * *